US006596758B1

(12) United States Patent
Brunet et al.

(10) Patent No.: US 6,596,758 B1
(45) Date of Patent: Jul. 22, 2003

(54) BENZOPYRANS AND BENZOXEPINES, PHARMACEUTICAL COMPOSITIONS COMPRISING THEM AND PREPARATION PROCESS

(75) Inventors: Michel Brunet, Toussieu (FR); Jean-Jaques Zeiller, Lyons (FR); Jean-Jaques Berthelon, Lyons (FR); Francis Contard, Lyons (FR); Guy Augert, Chanoz-Chatenay (FR); Daniel Guerrier, Saint Genis Laval (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/869,518

(22) PCT Filed: Dec. 20, 1999

(86) PCT No.: PCT/EP99/10114

§ 371 (c)(1), (2), (4) Date: Jun. 29, 2001

(87) PCT Pub. No.: WO00/39113

PCT Pub. Date: Jul. 6, 2000

(30) Foreign Application Priority Data

Dec. 29, 1998 (FR) .............................. 98 16574

(51) Int. Cl.[7] .................. A61K 31/382; A61K 31/353; C07D 313/08; C07D 311/04; C07D 335/06
(52) U.S. Cl. .................. 514/450; 514/432; 514/456; 549/23; 549/355; 549/405; 549/408
(58) Field of Search ................. 514/432, 450, 514/456; 549/23, 355, 405, 408

(56) References Cited

U.S. PATENT DOCUMENTS 4,946,860 A  8/1990  Morris et al. ............. 549/23

FOREIGN PATENT DOCUMENTS

| EP | 0591046 | 4/1994 |
| HU | 209559 | 7/1994 |
| WO | 9620913 | 7/1996 |

OTHER PUBLICATIONS

Chemical Abstracts, vol. 110 No. 26, 1989; abstract No. 94776x; Phillip E Brown; "Studies on Chromenes.Part 6", p. 661, abstract; J.Chem.Res.,Synop., vol. 7, p. 208, 1988.
Guy Fontaine: "Rech. Dans La Serie De L'Homochromanne.1." Annales De Chimie–Science Des Materiaux., vol. 3 No. 3, 1968, p. 179–184, Masson Et Cie.Paris, FR ISSN: 0223–5234, table 1.
Loic Rene R.Royer: "Sur La Synthese De Delta–3 Chromenes" European Journal of Medicinal Chemistry. Chimica Therapeutica., vol. 10, No. 1, Jan. 1997, p. 72–78; Editions Scientifique Elsevier, Paris.
Y.Satoh et al.: "Substituted chromenes" Journal of Medicinal Chemistry., vol. 36, 1993, p. 3580–3594.

Primary Examiner—Ba K. Trinh
(74) Attorney, Agent, or Firm—Millen, White, Zelano & Branigan, P.C.

(57) ABSTRACT

The present invention relates to benzopyrans and benzoxepines of formula (I), wherein X, A, $R_1$, $R_2$ and $(R)_p$ have the meanings as given in claim 1, which can be used in the treatment of dislipidaemias, atherosclerosis and diabetes, to pharmaceutical compositions comprising them and to processes allowing the preparation of these compounds.

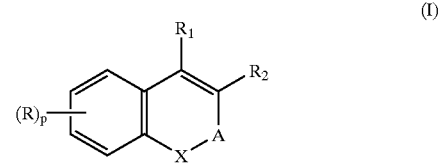

36 Claims, No Drawings

BENZOPYRANS AND BENZOXEPINES, PHARMACEUTICAL COMPOSITIONS COMPRISING THEM AND PREPARATION PROCESS

This application is a 371 of PCT/EP99/10114 dated Dec. 20, 1999.

The present invention relates to benzopyrans and benzoxepines which can be used in the treatment of dyslipidaemias, atherosclerosis and diabetes, to pharmaceutical compositions comprising them and to processes allowing the preparation of these compounds. compounds in the preparation of medicaments intended for the treatment of dyslipidaemias, atherosclerosis and diabetes.

Cardiovascular disease remains, in most countries, one of the main diseases and the main cause of mortality. Approximately a third of men develop a major cardiovascular disease before the age of 60, women exhibiting a lower risk (ratio of 1 to 10). This disease becomes more prevalent with age (after the age of 65, women become just as vulnerable to cardiovascular diseases as men). Vascular diseases, such as coronary disease, strokes, restenosis and peripheral vascular disease, remain the main cause of mortality and handicap across the world.

While diet and lifestyle can accelerate the development of cardiovascular diseases, a genetic predisposition leading to dyslipidaemias is a significant factor in strokes and deaths.

The development of atherosclerosis seems to be related mainly to dyslipidaemia, which means abnormal levels of lipoproteins in the blood plasma. This dysfunction is particularly evident in coronary disease, diabetes and obesity.

The concept intended to explain the development of atherosclerosis was mainly focused on the metabolism of cholesterol and on the metabolism of triglycerides.

However, since the studies by Randle et al. (lancet, 1963, 785–789), a novel concept has been proposed: a glucose-fatty acid cycle or Randle cycle, which describes the regulation of the equilibrium between the metabolism of lipids, in terms of triglycerides and cholesterol, and the oxidation of glucose. According to this concept, the Inventors have developed a novel programme having the aim of finding new compounds which act simultaneously on the metabolism of lipids and the metabolism of glucose.

Fibrates are well-known therapeutic agents with a mechanism of action via the "Peroxisome Proliferator Activated Receptors". These receptors are the main regulators of the metabolism of lipids in the liver (PPARα isoform). In the last ten years, thiazolidinediones have been described as powerful hypoglycaemic agents in animals and man. It has been reported that thiazolidinediones are powerful selective activators of another isoform of PPARs: the various PPARγ (Lehmann et al., J. Biol. Chem. 1995, 270, 12953–12956).

The Inventors have discovered a new class of compounds which are powerful activators of the PPARα and PPARγ isoforms. Due to this activity, these compounds exhibit a significant hypolipidaemic and hypoglycaemic effect.

The compounds of the invention correspond to the formula (I) below:

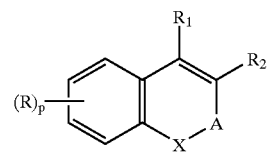

(I)

in which:
X represents O or S;
A represents either the divalent radical —(CH$_2$)$_s$—CO—(CH$_2$)$_t$— or the divalent radical —(CH$_2$)$_s$—CR$_3$R$_4$—(CH$_2$)$_t$—
in which radicals s=t=0 or else one of s and t has the value 0 and the other has the value 1;
R$_4$ represents a hydrogen atom or a (C$_1$-C$_{15}$)alkyl group;
R$_1$ and R$_2$ independently represent the Z chain defined below; a hydrogen atom; a (C$_1$-C$_{18}$)alkyl group; a (C$_2$-C$_{18}$)alkenyl group; a (C$_2$-C$_{18}$)alkynyl group; a (C$_6$-C$_{10}$)aryl group optionally substituted by a halogen atom, by an optionally halogenated (C$_1$-C$_5$)alkyl group or by an optionally halogenated (C$_1$-C$_5$)alkoxy group; or a mono- or bicyclic (C$_4$-C$_{12}$)heteroaryl group comprising one or more heteroatoms chosen from O, N and S which is optionally substituted by a halogen atom, by an optionally, halogenated (C$_1$-C$_5$)alkyl group or by an optionally halogenated (C$_1$-C$_5$)alkoxy group;
R$_3$ takes any one of meanings given above for R$_1$ and R$_2$, with the exception of the Z chain; or else
R$_3$ and R$_4$ together form a (C$_2$-C$_6$)alkylene chain optionally substituted by a halogen atom or by optionally halogenated (C$_1$-C$_5$)alkoxy;
R is chosen from a halogen atom; a cyano group; a nitro group; a carboxy group; an optionally halogenated (C$_1$-C$_{18}$)alkoxycarbonyl group; an R$_a$—CO—NH— or R$_a$R$_b$N—CO— group [in which R$_a$ and R$_b$ independently represent optionally halogenated (C$_1$-C$_{18}$)alkyl; a hydrogen atom; (C$_6$-C$_{10}$)aryl or (C$_6$-C$_{10}$)aryl (C$_1$-C$_5$)alkyl (where the aryl parts are optionally substituted by a halogen atom, by an optionally halogenated (C$_1$-C$_5$)alkyl group or by an optionally halogenated (C$_1$-C$_5$)alkoxy group); (C$_3$-C$_{12}$) cycloalkyl optionally substituted by a halogen atom, by an optionally halogenated (C$_1$-C$_5$)alkyl group or by an optionally halogenated (C$_1$-C$_5$)alkoxy group]; an optionally halogenated (C$_1$-C$_{18}$)alkyl group; optionally halogenated (C$_1$-C$_{18}$)alkoxy; and (C$_6$-C$_{10}$)aryl, (C$_6$-C$_{10}$)aryl(C$_1$-C$_5$)alkyl, (C$_6$-C$_{10}$)aryloxy, (C$_3$-C$_{12}$) cycloalkyl, (C$_3$-C$_{12}$)cycloalkenyl, (C$_3$-C$_{12}$) cycloalkyloxy, (C$_3$-C$_{12}$)cycloalkenyloxy or (C$_6$-C$_{10}$) aryloxycarbonyl in which the aryl, cycloalkyl and cycloalkenyl parts are optionally substituted by a halogen atom, by optionally halogenated (C$_1$-C$_5$)alkyl or by optionally halogenated (C$_1$-C$_5$)alkoxy;
p represents 0, 1, 2, 3 or 4;
Z represents the radical:

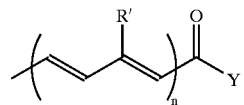

where n is 1 or 2;

the R' groups independently represent a hydrogen atom; a $(C_1-C_5)$alkyl group; a $(C_6-C_{10})$aryl group optionally substituted by a halogen atom, by an optionally halogenated $(C_1-C_5)$alkyl group or by optionally halogenated $(C_1-C_5)$alkoxy; or a mono- or bicyclic $(C_4-C_{12})$ heteroaryl group comprising one or more heteroatoms chosen from O, N and S which is optionally substituted by a halogen atom, by an optionally halogenated $(C_1-C_5)$alkyl group or by an optionally halogenated $(C_1-C_5)$alkoxy group;

Y represents —OH; $(C_1-C_5)$alkoxy; or the —NR$_c$R$_d$ group (in which R$_c$ and R$_d$ independently represent a hydrogen atom; $(C_1-C_5)$alkyl; $(C_3-C_8)$cycloalkyl optionally substituted by a halogen atom, by optionally halogenated $(C_1-C_5)$alkyl or by optionally halogenated $(C_1-C_5)$alkoxy; $(C_6-C_{10})$aryl optionally substituted by a halogen atom, by optionally halogenated $(C_1-C_5)$ alkyl or by optionally halogenated $(C_1-C_5)$alkoxy; it being understood that one and one alone from R$_1$ and R$_2$ represents the Z chain.

The invention is also targeted, depending on the functional groups present in the molecule, at the salts of these compounds with pharmaceutically acceptable acids or bases.

When the compound of formula (I) comprises an acidic functional group, for example a carboxyl functional group, the latter can form a salt with an inorganic or organic base.

Mention may be made, as example [sic] of salts with organic or inorganic bases, of the salts formed with metals and in particular alkali, alkaline earth and transition metals (such as sodium, potassium calcium, magnesium or aluminium) or with bases, such as ammonia or secondary or tertiary amines (such as diethylamine, triethylamine, piperidine, piperazine or morpholine), or with basic amino acids or with osamines (such as meglumine) or with aminoalcohols (such as 3-aminobutanol and 2-aminoethanol).

When the compound of formula (I) comprises a basic functional group, for example a nitrogen atom, the latter can form a salt with an organic or inorganic acid.

The salts with organic or inorganic acids are, for example, the hydrochloride, hydrobromide, sulphate, hydrogensulphase, dihydrogenphosphate, maleate, fumarate, 2-naphthalenesulphonate and para-toluene-sulphonate salts.

The invention also covers the salts which make possible a suitable separation or a suitable crystallization of the compounds of formula (I), such as picric acid, oxalic acid or an optically active acid, for example tartaric acid, dibenzoyltartaric acid, mandelic acid or camphorsulphonic acid.

The formula (I) encompasses all the types of geometric isomers and stereoisomers of the compounds of formula (I).

According to the invention, the term "alkyl" denotes a linear or branched hydrocarbon-comprising radical, such as methyl, ethyl, propyl, isopropyl, butyl, tert-butyl, isobutyl, pentyl, hexyl, heptyl, octyl, nonyl, decyl, undecyl, dodecyl, tridecyl, tetradecyl, pentadecyl, hexadecyl, heptadecyl or octadecyl.

When the alkyl group is substituted by one or more halogen atoms, it is preferable for it to represent perfluoroalkyl and in particular penafluoroethyl or trifluoromethyl.

The term "alkoxy" denotes an alkyl group as defined above bonded to an oxygen atom. Examples thereof are the methoxy, ethoxy, isopropyloxy, butoxy and hexyloxy radicals.

The term "alkylene group" is understood to mean linear or branched alkylene groups, that is to say bivalent radicals which are linear or branched bivalent alkyl chains.

The term "cycloalkyl" denotes saturated hydrocarbon-comprising groups which can be mono- or polycyclic and comprise from 3 to 12 carbon atoms, preferably from 3 to 8. Preference is more particularly given to monocyclic cycloalkyl groups, such as cyclopropyl, cyclobutyl, cyclopentyl, cyclohexyl, cycloheptyl, cyclooctyl, cyclononyl, cyclodecyl, cycloundecyl and cyclododecyl.

The term "cycloalkenyl" is understood to mean, according to the invention, a cycloalkyl group exhibiting one or more double bonds.

The term "halogen" is understood to mean a fluorine, chlorine, bromine or iodine atom.

The term "aryl" represents a mono- or bicyclic aromatic hydrocarbon-comprising group comprising 6 to 10 carbon atoms, such as phenyl or naphthyl.

The term "mono- or bicyclic heteroaryl" denotes monocyclic or bicyclic aromatic groups comprising one or more endocyclic heteratoms. Examples thereof are the furyl, thienyl, pyrrolyl, oxazolyl, isoxazolyl, thiazolyl, isothiazolyl, imidazolyl, pyrazolyl, oxadiazolyl, triazolyl, thiadiazolyl, pyridinyl, pyridazinyl, pyrazinyl, triazinyl, indolizinyl, indolyl, isoindolyl, benzofuryl, benzothienyl, indazolyl, benzimidazolyl, benzothiazolyl, purinyl, quinolyl, quinolizinyl, iqoquinolyl [sic], cinnolinyl, phthalazinyl, quinazolinyl, quinoxalinyl, pteridinyl and benzoxepinyl groups.

Preferred heteroaryls comprise from 4 to 10 carbon atoms and from 1 to 2 heteroatoms.

The alkenyl and alkynyl groups can comprise more than one unsaturation.

The alkenyl groups comprise unsaturations of ethylenic type and the alkynyl groups comprise unsaturations of acetylenic type.

The $(C_6-C_{10})$aryl, $(C_3-C_8)$cycloalkyl, heteroaryl and cycloalkenyl groups are optionally substituted. The expression "optionally substituted by a halogen atom, by an optionally halogenated $(C_1-C_{15})$alkyl group or by an optionally halogenated $(C_1-C_5)$alkoxy group" indicates that the said aryl, cycloalkyl, heteroaryl and cycloalkenyl groups are optionally substituted by one or more substituents chosen from:

halogen atoms;

alkyl groups optionally substituted by one or more halogen atoms; and alkoxy groups optionally substituted by one or more halogen atoms.

In the same way, the alkylene chain, when it is substituted, can comprise one or more identical or different substituents chosen from halogen atoms and optionally halogenated alkoxy groups.

The expression "optionally halogenated" means, in the context of the invention, optionally substituted by one or more halogen atoms.

In the context of the present invention, the term "benzoxepine" has been used to denote the benzo[b]oxepine structure of formula:

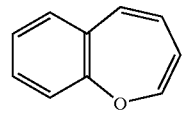

According to the invention, preference is given to the compounds in which A represents the radical:

where s, t, $R_3$ and $R_4$ are as defined above for the formula (I).

Another preferred group of compounds of formula (I) is composed:
• of the compounds in which:

X represents O;

A represents —$CR_3R_4$— or —$CH_2$—$CR_3R_4$— in which the unsubstituted methylene group is bonded to X;

$R_1$ and $R_2$ independently represent Z; H; ($C_1$–$C_{15}$)alkyl; ($C_1$–$C_{15}$)alkenyl [six]; or phenyl optionally substituted by ($C_1$–$C_5$)alkyl, ($C_1$–$C_5$)alkoxy, a halogen atom or —$CF_3$;

$R_3$ takes any one of the meanings given above for $R_1$ and $R_2$, with the exception of Z;

R is chosen from ($C_1$–$C_9$)alkyl; ($C_1$–$C_5$)alkoxy; phenyl or phenylcarbonyl optionally substituted by a halogen atom, ($C_1$–$C_5$)alkyl, ($C_1$–$C_5$)alkoxy, —$CF_3$ or —$OCF_3$; a halogen atom; —$CF_3$ and —$OCF_3$;

Z represents the radical:

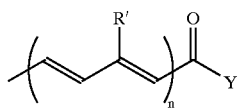

where n represents 1;

R' represents ($C_1$–$C_5$)alkyl.

Preference is given, among these compounds, to those in which:

X represents O;

A represents —$CR_3R_4$—;

Z represents

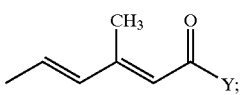

• or alternatively those in which:

X represents O;

A represents —$CH_2$—$CR_3R_4$— in which the unsubstituted methylene group is bonded to X;

$R_1$ and $R_2$ independently represent Z, a hydrogen atom or ($C_1$–$C_5$)alkyl;

$R_3$ takes any one of the meanings given above for $R_1$ and $R_2$, with the exception of Z;

Z represents

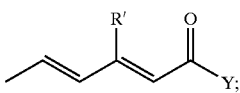

R' represents methyl or phenyl.
Preferred meanings of Y are:
—OH
—($C_1$–$C_5$)alkoxy; and
—$NR_cR_d$ where $R_c$ and $R_d$ are as defined above for the formula (I).

Very preferably, Y represents —OH or —($C_1$–$C_5$)alkoxy. Likewise, it is preferable for p to have the value 0, 1 or 2.

According to a particularly advantageous embodiment of the invention, the compounds of the groups which are preferred defined above are such that p and Y take one of these meanings.

Mention may be made, as example [sic] of preferred compounds, of the following compounds:

—(2E, 4E)-5-(2-pentyl-2H-1-benzopyran-3-yl)-3-methylpenta-2,4-dienoic acid;
—(2Z, 4E)-5-(2-pentyl-2H-1-benzopyran-3-yl)-3-methylpenta-2,4-dienoic acid;
—(2E, 4E)-5-(2,2-dimethyl-6-methoxy-2H-1-benzopyran-3-yl)-3-methylpenta-2,4-dienoic acid;
—(2E, 4E)-5-(2H-1-benzopyran-3-yl)-3-methylpenta-2,4-dienoic acid;
—(2E, 4E)-5-(2,2-dimethyl-2H-1-benzopyran-3-yl)-3-methylpenta-2,4-dienoic acid;
—(2Z, 4E)-5-(2,2-dimethyl-2H-1-benzopyran-3-yl)-3-methylpenta-2,4-dienoic acid;
—(2E, 4E)-5-[2-(non-6-enyl)-2H-1-benzopyran-3-yl]-3-methylpenta-2,4-dienoic acid;
—(2E, 4E)-5-(4-phenyl-2H-1-benzopyran-3-yl)-3-methylpenta-2,4-dienoic acid;
—(2E, 4E)-5-(6-nonyl-2H-1-benzopyran-3-yl)-3-methylpenta-2,4-dienoic acid;
—(2E, 4E)-5-(6-phenyl-2H-1-benzopyran-3-yl)-3-methylpenta-2,4-dienoic acid;
—(2E, 4E)-5-(2-nonyl-2H-1-benzopyran-3-yl)-3-methylpenta-2,4-dienoic acid;
—(2E, 4E)-5-(4-methyl-2H-1-benzoypyran-3-yl)-3-methylpenta-2,4-dienoic acid;
—(2Z, 4E)-5-(2H-1-benzopyran-3-yl)-3-methylpenta-2,4-dienoic acid;
—(2E, 4E)-5-(2-undecanyl-2H-1-benzopyran-3-yl)-3-methylpenta-2,4-dienoic acid;
—(2E, 4E)-5-(2-phenyl-2H-1-benzopyran-3-yl)-3-methylpenta-2,4-dienoic acid;
—(2E, 4E)-5-(5-methyl-2,3-dihydrobenzoxepin-4-yl)-3-methylpenta-2,4-dienoic acid;
—(2E, 4E)-5-(3,3-dimethyl-7-methoxy-2,3-dihydrobenzoxepin-5-yl)-3-methylpenta-2,4-dienoic acid; and [sic]
—(2E, 4E)-5-(2,3-dihydrobenzoxepin-4-yl)-3-methylpenta-2,4-dienoic acid;
—(2E, 4E)-5-(3,3-dimethyl-7-methoxy-2,3-dihydrobenzoxepin-5-yl)-3-phenylpenta-2,4-dienoic acid;
—(2Z, 4E)-5-(3,3-dimethyl-7-methoxy-2,3-dihydrobenzoxepin-5-yl)-3-phenylpenta-2,4-dienoic acid;
—(2Z, 4E)-5-(3,3-dimethyl-7-methoxy-2,3-dihydrobenzoxepin-5-yl)-3-methylpenta-2,4-dienoic acid;
—(2E, 4E)-5-(3,3-dimethyl-7,8-dimethoxy-2,3-dihydrobenzoxepin-5-yl)-3-methylpenta-2,4-dienoic acid;
—(2E, 4E)-5-(3,3-dimethyl-2,3-dihydrobenzoxepin-5-yl)-3-methylpenta-2,4-dienoic acid;
—(2E, 4E)-5-(3,3-dimethyl-2,3-dihydro-7-(para-chlorobenzoyl)benzoxepin-5-yl)-3-methylpenta-2,4-dienoic acid;
—(2E, 4E)-5-(3,3-dimethyl-7-chloro-2,3-dihydrobenzoxepin-5-yl)-3-methylpenta-2,4-dienoic acid;
—(2E, 4E)-5-(3,3-dimethyl-7,8-dichloro-2,3-dihydrobenzoxepin-5-yl)-3-methylpenta-2,4-dienoic acid;
—(2E, 4E)-5-(3,3-dimethyl-7-bromo-2,3-dihydrobenzoxepin-5-yl)-3-methylpenta-2,4-dienoic acid;

—(2E, 4E)-5-(3,3-dimethyl-7-fluoro-8-chloro-2,3-dihydrobenzoxepin-5-yl)-3-methylpenta-2,4-dienoic acid;
—(2E, 4E)-5-(3,3-dimethyl-7-fluoro-2,3-dihydrobenzoxepin-5-yl)-3-methylpenta-2,4-dienoic acid;
—(2E, 4E)-5-(3,3-dimethyl-7-trifluoromethyl-2,3-dihydrobenzoxepin-5-yl)-3-methylpenta-2,4-dienoic acid;
—(2E, 4E)-5-(3,3-dimethyl-7-phenyl-2,3-dihydrobenzoxepin-5-yl)-3-methylpenta-2,4-dienoic acid;
—(2E, 4E)-5-(3,3,7-trimethyl-2,3-dihydrobenzoxepin-5-yl)-3-methylpenta-2,4-dienoic acid;
—(2E, 4E)-5-(3,3-dimethyl-2,3-dihydrobenzoxepin-5-yl)-3-methylpenta-2,4-dienoic acid;
—(2E, 4E)-5-(9-methoxy-3,3-dimethyl-2,3-dihydrobenzoxepin-5-yl)-3-methylpenta-2,4-dienoic acid;

and their pharmaceutically acceptable esters, such as their ethyl esters.

FR 2,698,873 discloses compounds of formula:

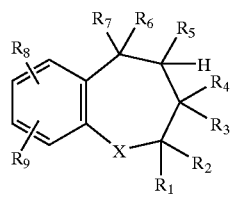

which are powerful activators of the potassium channels of the cell membrane.

According to this document, none of the $R_1$ to $R_7$ substituents represents the Z chain as defined in the invention.

U.S. Pat. No. 5,391,569 relates to benzopyrans of formula:

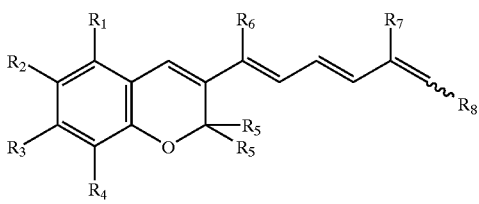

of use in the treatment of osteoporosis and inflammations. These compounds differ from the compounds of the invention in that the alkenyl chain comprises three double bonds, whereas, according to the invention, the Z chain comprises either two or four double bonds.

It should be noted that the hypolipidaemic and hypoglycaemic activity of the compounds of the invention is unrelated to the activity of the compounds disclosed in the documents U.S. Pat. No. 5,391,569 and FR 2,698,273.

The compounds of formula (I) can be prepared by using one of the following Processes A or B, which processes form another subject-matter of the invention.

Process A makes possible the preparation of the compounds of formula (I) in which n represents 1.

This process comprises the stages composed of:
(a1) preparing an ylide
  • either by reaction of a base with a phosphonate of formula:

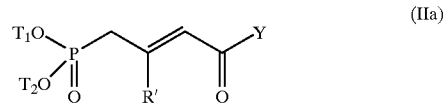

in which
R' is as defined in Claim 1 [sic];
$T_1$ and $T_2$ independently represent $(C_1-C_5)$alkyl; and
Y represents $(C_1-C_5)$alkoxy,
  • or by reaction of a base with a phosphonium salt of formula (IIb);

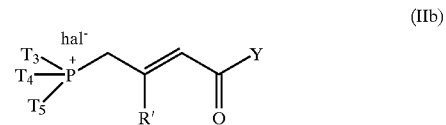

in which
R' is as defined in Claim 1 [sic];
$T_3$, $T_4$ and $T_5$ independently represent $(C_1-C_5)$alkyl or $(C_6-C_{10})$aryl optionally substituted by $(C_1-C_5)$alkyl;
Y represents $(C_1-C_5)$alkoxy; and
hal represents a halogen atom;
(b1) reacting the ylide obtained in Stage (a1) with an aldehyde of formula:

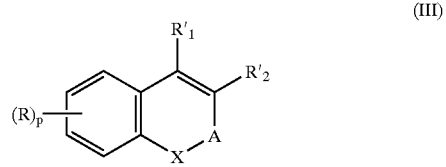

in which
R, p, X and A are as defined in Claim 1 [sic];
one and one alone of $R'_1$ and $R'_2$ represents —CHO and the other takes one of the meanings given in Claim 1 [sic] for $R_1$ and $R_2$, with the exception of the Z chain, so as to obtain a compound of formula (I) in which n represents 1 and Y represents $(C_1-C_5)$alkoxy;
(c1) if appropriate, converting the ester obtained in Stage (b1) above in acidic or basic medium into the corresponding carboxylic acid of formula (I) in which Y represents OH;
(d1) if appropriate, reacting the carboxylic acid functional group of the compound of formula (I) resulting from Stage (c1) with an amine of formula $HNR_cR_d$ in which $R_c$ and $R_d$ are as defined in Claim 1 [sic], optionally after activation of the carboxyl functional group, so as to prepare the corresponding compound of formula (I) in which Y represents —$NR_cR_d$.

The reaction employed in Stage (b1) is either a Wittig reaction or a Horner-Emmons or Wadsworth-Emmons reaction.

It results in the preparation of a reactive ylide.

When the ylide is prepared from a phosphonium salt (compound IIb), the reaction employed is a Wittig reaction.

When the ylide is prepared from a phosphonate (compound IIa), the reaction employed is a Horner-Emmons or Wadsworth-Emmons reaction.

In Stage a1 [sic], the ylide is prepared by reaction of a base either with a compound IIa [sic] or with a compound IIb [sic]. The base used must be sufficiently strong to detach the proton at the position α to the phosphorus.

The base is generally chosen from an alkali metal hydride, an alkali metal carbonate, an alkali metal amide, a ($C_1$–$C_{10}$) alkyllithium and an alkali metal alkoxide.

Mention may be made, by way of example [sic], of sodium hydride, potassium carbonate, n-butyllithium, potassium tert-butoxide, a [sic] lithium amide or a [sic] sodium amide.

In the context of the invention, sodium hydride and potassium tert-butoxide are preferred as base.

The reaction of the base with the compound (IIa) OR (IIb) is carried out in solution, preferably in an aprotic solvent and more particularly in a solvent capable of dissolving the phosphonate (IIa) or the phosphonium salt (IIb) respectively.

Appropriate solvents are aprotic solvents, such as, for example and non-limitingly, aromatic hydrocarbons (such as benzene and toluene), ethers (such as diethyl ether, dioxane or tetrahydrofuran) and their mixtures.

The choice of the solvent depends in particular on the type of ylide (compounds IIa or IIb).

According to a preferred embodiment of the invention, stage (b2) [sic] of reaction of the aldehyde with the ylide is carried out by addition of the aldehyde (III) to the crude reaction mixture resulting from Stage (a1), that is to say without isolation of the intermediate ylide.

Thus, it is desirable for the solvent of Stage (a1) also to be capable of dissolving the aldehyde (III). However, another embodiment of the invention comprises the addition of a solution of the aldehyde (III) in a solvent to the crude reaction mixture resulting from Stage (a1). Under these conditions, it is not necessary to select, in Stage (a1), a solvent capable of dissolving the compound (III).

The temperature at which Stage (a1) is carried out depends on the acidity of the compound (IIa) or (IIb) respectively, that is to say on the ease with which the proton at the position α to the phosphorus can be detached. It goes without saying that the type of base used directly influences the choice of the reaction temperature. Thus, the stronger the base, the lower the reaction temperature. When the base used is n-butyllithium, a temperature of between –80° C. and –40° C., preferably between –80° C. and –70° C., is generally desirable. In this case, the solvent is chosen so as to make possible such severe reaction conditions; ethers are very particularly well suited.

When the base is an alkali metal alkoxide, a temperature of between 10 and 100° C. is generally suitable. If, furthermore, this base is reacted with a phosphonate (IIa), a temperature of between 15 and 70° C. is generally sufficient.

When the base used is an alkali metal hydride, the temperature is generally between –10° C. and 50° C. If, furthermore, this base is reacted with a phosphonate (IIa), a temperature of between –5° C. and 30° C. is generally sufficient.

A stoichiometric amount of the base is needed in Stage (a1) to detach the proton at the position α to the phosphorus on the compound (IIa) or (IIb) respectively. Nevertheless, it is possible to use a very slight excess of base, so that the reaction for the formation of the ylide is complete. Thus, the molar ratio of the base to the compound (IIa) or (IIb) respectively is maintained between 1 and 1.2, preferably between 1 and 1.1, better still between 1 and 1.05.

The concentration of the compound (IIa) or (IIb) respectively in the reaction mixture is not critical according to the invention. The concentration generally varies between 0.01 mol/l and 10 mol/l, preferably between 0.1 and/ 1 mol/l.

In Stage (b1), the aldehyde (III) is reacted with the ylide resulting from Stage (a1).

The aldehyde (III) is advantageously added to the crude reaction mixture resulting from Stage (a1).

The aldehyde (III) can be added as is to the reaction mixture or else in solution in a solvent, preferably an aprotic solvent.

Mention may be made, as preferred solvents, of solvents of aromatic hydrocarbon, ether, N-dimethylformamide [sic], dimethyl sulphoxide, N-methylpyrrolidone or P[N($CH_3$)$_2$]$_3$ type and their mixtures which were cited above.

Whatever the operating procedure, it is preferable for the concentration of aldehyde (III) in the reacting mixture to vary between $6 \times 10^{-3}$ and 0.6 mol/l, preferably between 0.01 and 0.7 mol/l.

The temperature at which the ylide reacts with the aldehyde (III) depends on the respective reactivity of the two reactants.

It should be noted that the ylide prepared from the phosphonate (IIa) is more reactive than the ylide prepared from the compound (IIb). Thus, Process A, involving the implementation of a reaction of Horner-Emmons type with the use of the phosphonate (IIa), is particularly advantageous.

Generally, a temperature of between –10° C. and 50° C. is appropriate for the reaction of the ylide with the aldehyde (III), a temperature of between –5° C. and 30° C. being more particularly well suited.

In may be necessary to bring the crude reaction mixture resulting from Stage (a1) to this temperature before carrying out Stage (b1), in so far as the temperature conditions involved in Stages (a1) and (b1) differ.

More generally, a person skilled in the art may draw inspiration from the operating conditions described in the literature for the Wittig and Horner-Emmons reactions for the purpose of preparing the compound of formula (I) in which n is 1 and Y represents ($C_1$–$C_5$)alkoxy obtained on conclusion of Stages (a1) and (b1).

Stage (c1) makes possible the hydrolysis of the ester of formula (I) resulting from Stage (b1). This stage is advantageously carried out in basic medium. The bases generally used for the saponification of esters can be used for the implementation of Stage (c1). These bases preferably inorganic bases of the alkali metal hydroxide type (NaOH, KOH) or of the alkali metal carbonate type ($K_2CO_3$, $Na_2CO_3$).

The hydrolysis of the ester functional group is generally carried out in a solvent, such as a protic solvent. ($C_1$–$C_5$) alkanol [sic], water and their mixtures are particularly well suited.

The hydrolysis is advantageously carried out at a temperature of 0 to 100° C., for example 20 to 80° C., in a mixture of methanol and water, by reaction with sodium hydroxide.

The amount of base needed is usually between 1 to 5 equivalents with respect to the ester of formula (I), preferably between 1 and 2 equivalents.

Although this does not correspond to a preferred embodiment of the invention, the hydrolysis of the ester functional group can be carried out in acidic medium.

In order to determine the ideal conditions for hydrolysis of the ester functional group, a person skilled in the art should refer, for example, to Protective Groups in Organic Synthesis, Greene T. W. and Wuts P. G. M., published by John Wiley & Sons, 1991, and to Protecting Groups, Kocienski P. J., 1994, Georg Thieme Verlag.

Stage (d1) is carried out for the preparation of compounds of formula (I) in which Y represents —$NR_cR_d$.

In comprises a conventional reaction of the carboxylic acid obtained in Stage (c1) with an amine of formula $NHR_cR_d$. It is more particularly advantageous to react an activated form of the carboxylic acid of formula (I) with the amine $NHR_cR_d$. Such an activated form is, for example, a carboxylic acid anhydride, an acid chloride or a mixed anhydride. The amidation of the carboxyl functional group will be carried out in a way known per se by a person skilled in the art.

Process B makes possible the preparation of the compounds of formula (I) in which n=2. This process comprises the stages composed of:

(a2) preparing an ylide
• either by reaction of a base with a phosphonate of formula (IVa):

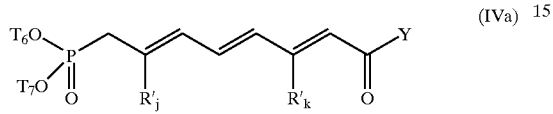

in which
$R'_j$ and $R'_k$ independently represent an R' group as defined in Claim 1 [sic];
$T_6$ and $T_7$ independently represent $(C_1-C_5)$alkyl; and
Y represents $(C_1-C_5)$ alkoxy;
• or by reaction of a base with a phosphonium salt of formula (IVb):

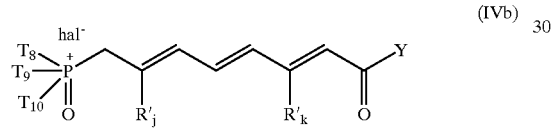

in which
$R'_j$ and $R'_k$ independently represent and R' group as defined in Claim 1 [sic];
$T_8$, $T_9$ and $T_{10}$ independently represent $(C_1-C_5)$alkyl or $(C_6-C_{10})$aryl optionally substituted by $(C_1-C_5)$alkyl;
Y represents $(C_1-C_5)$alkoxy; and
hal represents a halogen atom;

(b2) reacting the ylide prepared in Stage (a2) with an aldehyde of formula:

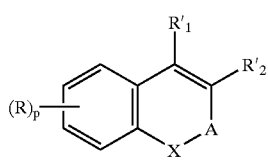

in which
R, p, X and A are as defined in Claim 1 [sic];
one and one alone of $R'_1$ and $R'_2$ represents —CHO and the other takes one of the meanings given in Claim 1 [sic] for $R_1$ and $R_2$, with the exception of the Z chain, so as to obtain a compound of formula I [sic] in which n represents 2 and Y represents $(C_1-C_5)$alkoxy;

(c2) if appropriate, converting the ester obtained in Stage (b2) above in acidic or basic medium into the corresponding carboxylic acid of formula (I) in which Y represents OH;

(d2) if appropriate, reacting the carboxylic acid functional group of the compound of formula (I) resulting from Stage (c2) with an amine of formula $HNR_cRin$ which $R_c$ and $R_d$ are as defined in Claim 1 [sic], optionally after activation of the carboxyl functional group, so as to prepare the corresponding compound of formula (I) in which Y represents —$NR_cR$.

The general conditions for carrying out Stages (a1) to (d1) also apply in carrying out the above Stages (a2) to (d2).

The phosphonate (IIa) is prepared conventionally, for example by carrying out the Arbuzov reaction. More specifically, when $T_1$ and $T_2$ are identical, a phosphite (IX):

$$P(OT_1)_3 \qquad (IX)$$

in which $T_1$ has the meaning given above for the formula (IIa), is reacted with a halide (X):

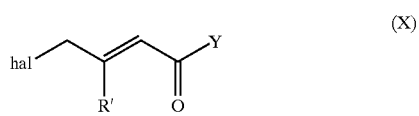

in which R' and Y are as defined above for the formula (IIa) and hal represents a halogen atom.

The same type of reaction results in the preparation of the phosphonate (IVa).

The phosphonium salts of formula (IIb) are easily prepared in a way known per se by the reaction of a phosphine (V):

in which $T_3$, $T_4$ and $T_5$ are as defined for the formula (IIb), with a halide (VI):

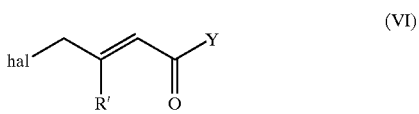

in which R', Y and hal are as defined above for the formula (IIb).

Likewise, the phosphonium salt of formula (IVb) is easily prepared by the reaction of the phosphine (VII)

in which $T_8$, $T_9$ and $T_{10}$ are as defined above for the formula (IVb), with the halide (VIII):

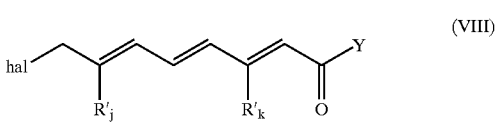

in which hal, $R'_j$, $R'_k$ and Y are as defined above for the formula (IVb). Reference may be made to the experimental conditions described by A. Zumbrunn et al. in Helv. Chim. Acta, 1985, 68, 1519.

The aldehydes of formula (III) are commercially available or are easily prepared from commercial products by employing one of the following processes.

Process C for the preparation of the aldehydes of formula (III):

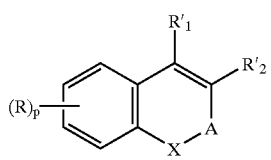

in which $R'_1$ represents —CHO.

The reaction sequence of Process C is illustrated in Scheme 1.

Stage (i) makes possible the reductive alkylation of the ketone (XI). This reaction comprises the reaction of the ketone (XI) with an organometallic compound $$CH_3-M$$

in which M is —MG-hal (where hal is a halogen atom) or else M is Li.

Scheme 1

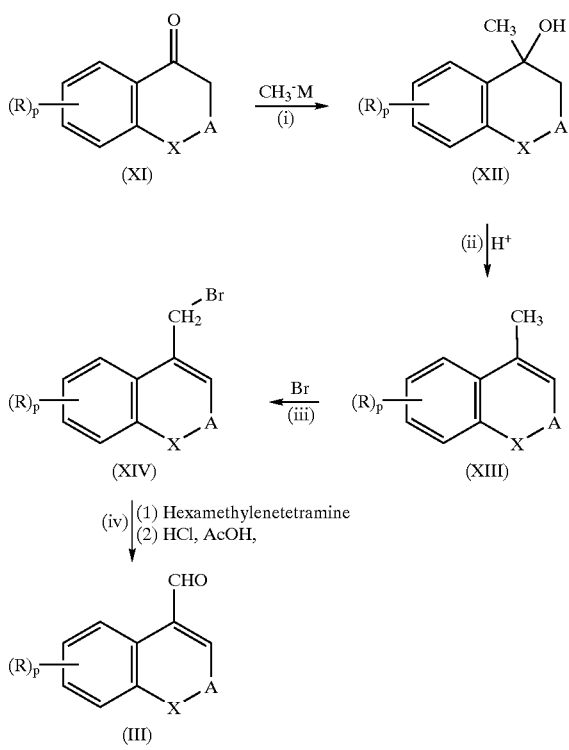

In Stage (i), the nature of the organometallic compound determines the operating conditions.

When the organometallic [sic] is a Grignard reagent, use is advantageously made of a solvent which can be diethyl ether, tetrahydrofuran, dioxane, benzene, toluene or the like. The reaction temperature is from −78° C. to 100° C., preferably −10° C. to 70° C.

Stage (ii) makes possible the dehydration of the compound of formula (XII). This dehydration can be obtained by the action of an organic or inorganic acid on the compound (XII).

Mention may be made, as example [sic] of acids, of hydrochloric acid, sulphuric acid, nitric acid, trifluoromethanesulphonic acid, acetic acid, trifluoroacetic acid, para-toluenesulphonic acid or p-nitrobenzoic acid.

The appropriate solvents for this reaction are those conventionally used in the art which are furthermore capable of dissolving the compounds of formula (XII). Preferred solvents are aromatic hydrocarbons, such as benzene and toluene.

In Stage (iii), the radical bromination of the compound of formula (XIII) is carried out. This reaction can be carried out conventionally by the action of a brominating agent, either by irradiation or under the action of heat, optionally in the presence of an initiator, such as a peroxide or an azo compound.

Brominating agents are, for example, bromine or N-bromosuccinimide.

Radical initiator examples are α,α'-azobisisobutyronitrile and tert-butyl peroxide. A particularly appropriate solvent is carbon tetrachloride.

Stage (iv) involves the reaction of hexamethylenetetramine with the compound (XIV) in a first stage and treatment with a mixture of acetic acid and hydrochloric acid in a second stage.

The molar ratio of hexamethylenetetramine to the compound (XIV) is preferably between 1 and 3, preferably between 1 and 2.

The temperature for reaction of hexamethylenetetramine with the compound (XIV) preferably varies between 20 and 120° C., better still between 30 and 80° C. The reaction is advantageously carried out in a solvent. Mention may be made, as appropriate solvent, of optionally halogenated aliphatic, aromatic or cycloaliphatic hydrocarbons, for example chloroform, carbon tetrachloride, tetrachloroethylene and chlorobenzene.

The following acidic treatment comprises the treatment, in a first step, of the resulting reaction mixture with an acetic acid solution at a temperature of 20 to 120° C. preferably of 30 to 80° C. In a second step, concentrated hydrochloric acid is added to the reaction mixture, which is maintained at a temperature of between 20 and 120° C. preferably between 30 and 80° C.

Process D for the preparation of the compounds of formula (III):

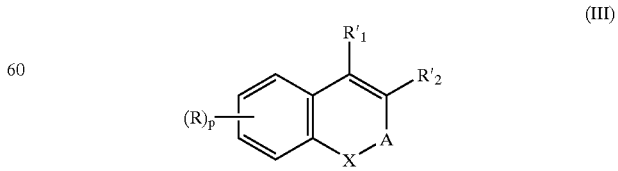

in which $R'_2$ is —CHO, A represents —$CR_3R_4$— as defined above and X represents O.

According to this process, an aldehyde of formula (XV):

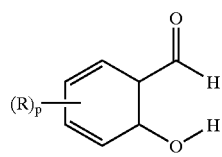

(XV)

in which R and p are as defined above for the formula (III), is reacted with a compound of formula (XVI):

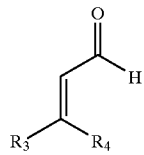

(XVI)

in which $R_3$ and $R_4$ are as defined above for the formula (II), in the presence of a strong base.

This reaction is stoichiometric. Nevertheless, it is preferable to carry out the reaction in the presence of a slight excess of the compound (XV), so that the molar ratio of the compound (XV) to the compound (XVI) generally varies from 1 to 1.5, better still from 1 to 1.3.

The base which can be used in this reaction is advantageously an inorganic base, such as, for example, NaOH, KOH, $NaHCO_3$, $Na_2CO_3$, $KHCO_3$ or $K_2CO_3$. According to a preferred embodiment of the invention, the base is $K_2CO_3$.

The amount of base which has to be used corresponds to the amount of compound (XV) involved. Thus, the molar ratio of the base to the compound (XV) is preferably between 1 and 1.2.

This reaction can be carried out in a solvent. The nature of the solvent depends on the base used and on the reactants present. When the base is $K_2CO_3$, ethers are preferred solvents and in particular dioxane, tetrahydrofuran or diethyl ether. When the reaction is carried out in the presence of a solvent, the concentration of the reactants in the reaction mixture is preferably maintained between 0.05 mol/l and 5 mol/l, better still between 0.08 mol/l and 1.2 mol/l. The reaction temperature is advantageously between 30 and 150° C., better still between 50 and 120° C., for example between 90 and 100° C.

Process E for the preparation of an aldehyde (III) of formula:

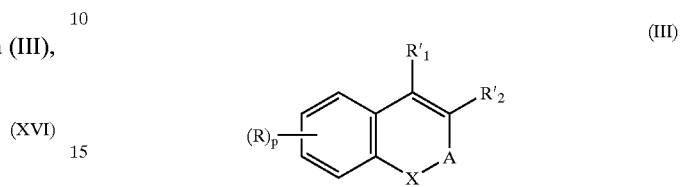

(III)

in which $R'_2$ represents the —COH [sic] group.

The reaction sequence of Process E is illustrated in Scheme 2.

Scheme 2

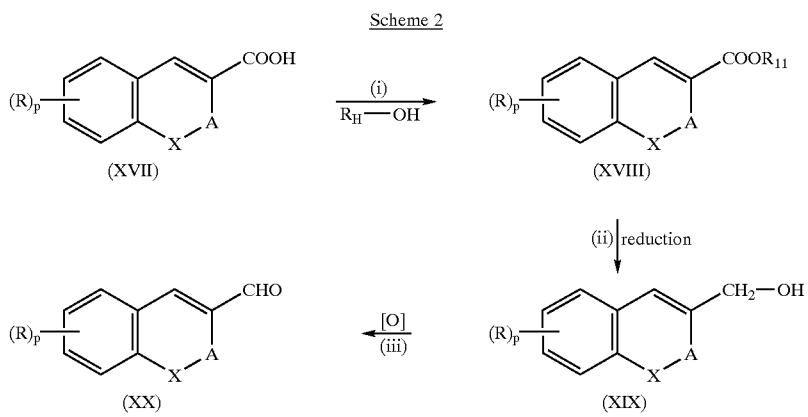

Process E comprises the use of conventional reactions of organic chemistry. In Stage (i), the carboxylic acid (XVII) is esterified by an alcohol of formula $R_H$OH in which $R_H$ is a $(C_1-C_6)$alkyl group.

The esterification is generally carried out in acidic medium. Catalytic amounts of acids of the paratoluenesulphonic acid type or sulphuric acid type are particularly appropriate. However, the reaction can be carried out in the presence of an excess of acid.

It is desirable to use a large excess of the alcohol $R_H$—OH. Likewise, it is advantageous to introduce a dehydrating agent, such as molecular sieve, into the reaction mixture. A reaction temperature of between 20 and 120° C., preferably between 50 and 100° C., is ideal.

It is possible in many cases to use the alcohol $R_H$—OH as solvent.

According to the invention, the nature of the $R_H$ group introduced in Stage (i) is not of any importance.

In the following stage, the ester (XVIII) is reduced to an alcohol (XIX). The reduction can be carried out according to any one of the methods known in the art.

Use may be made, as reducing agent, of, for example, lithium aluminium hydride, lithium borohydride, diisobutylaluminium hydride, lithium triethylborohydride, $BH_3$-$SMe_2$ at reflux in tetrahydrofuran, $HSi(OEt)_3$ or even sodium borohydride.

In Stage (iii), the alcohol (XIX) is oxidized to an aldehyde, so as to obtain the expected aldehyde (XX). The oxidation is carried out in a way known per se. It is advisable to avoid the subsequent oxidation of the aldehyde to an acid. For this reason, the oxidizing agent will be suitably selected from $MnO_2$, dimethyl sulphoxide, Collins's reagent, Corey's reagent, pyridinium dichromate, $Ag_2CO_3$ on celite, hot $HNO_3$ in aqueous glyme, $Pb(OAc)_4$-pyridine, ceric ammonium nitrate or N-methylmorpholine N-oxide.

Process F for the preparation of compounds of formula III [sic]:

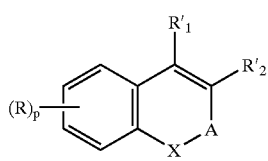

(III)

in which $R'_2$ represents the —CHO group.

According to this process, the compounds of formula (III) are prepared by the reaction of a mixture of phosphorus oxychloride and dimethylformamide with a compound of formula (XXI):

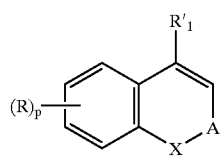

(XXI)

in which R, p, X, A and $R'_1$ are as defined above for the formula (III).

Use is preferably made of a molar ratio of phosphorus oxychloride to the compound (XXI) and of a molar ratio of dimethylformamide to the compound of formula (XXI) varying between 1 and 3, better still between 1 and 2, for example between 1 and 1.5.

The dimethylformamide and the phosphorus oxychloride are advantageously used in equal amounts.

One way of carrying out the reaction comprises preparing a solution of the reactants, phosphorus oxychloride and dimethylformamide, in a solvent and then running a solution of the compound (XXI) into this solution.

The solution of the reactants is generally prepared by addition of phosphorus oxychloride to a solution of dimethylformamide in a solvent. A halogenated aliphatic hydrocarbon (such as dichloromethane) or acetonitrile can be chosen as appropriate solvent.

The addition of $POCl_3$ to the DMF solution is preferably carried out under cold conditions, namely at a temperature of between −40 and 15° C., advantageously between −10 and 10° C., better still between −5 and +5° C.

The compound of formula (XXI) is added, preferably in solution in a solvent, to this solution. According to a preferred embodiment of the invention, the solvent is the same as that used to prepare the solution of the reactants.

The reaction of the compound (XXI) with the system of reactants $DMF/POCl_3$ is carried out at a temperature of between 15 and 100° C., preferably between 18 and 70° C.

The compound of formula (XXI) is easily prepared from the corresponding ketone of formula (XI):

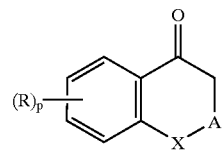

(XI)

in which R, p, X and A are as defined above for the formula (XXI). It is possible, for example, to prepare this compound by carrying out reactions analogous to those described above in the context of Process C (Scheme 1: Stages (i) and (ii)). Briefly, the above ketone (XI) can be reacted with an organometallic compound of formula: $R'_1$-M, where M is a lithium atom or represents —MG-hal, hal being a halogen atom. The resulting compound of formula:

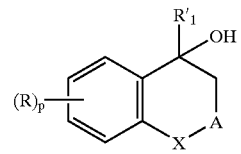

in which R, p, X and A are as defined above, is then treated in acidic medium.

The ketones of formula (XL), the aldehydes of formula (XV) and the acids of formula (XVII) are commercial compounds or are easily prepared from commercially available products by employing conventional processes of the state of the art.

Another subject-matter of the invention is the new compounds of formula:

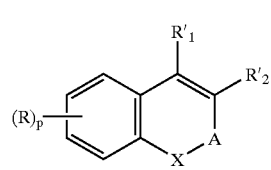

(IIIa)

in which:

A represents the bivalent radical —$(CH_2)_s$—$CR_3R_4$—$(CH_2)_t$— where one of s and t represents 0 and the other 1;

$R_3$, $R_4$, R, p and X are as defined above for the formula (I); and one alone of $R'_1$ and $R'_2$ represents —CHO, the other taking one of the meanings given above for $R_1$ and $R_2$ for the formula (I), with the exception of the Z chain.

Preference is given, among these compounds, to those in which $R'_1$ represents —CHO.

Another group of preferred compounds is composed of the compounds of above formula (IIIa) in which X represents O;

A represents —$CH_2$—$CR_3R_4$— in which the unsubstituted methylene group is bonded to X;

$R'_1$ or $R'_2$ represents H; $(C_1-C_{15})$alkyl; $(C_1-C_{15})$ alkenyl [sic]; or phenyl optionally substituted by $(C_1-C_5)$alkyl, $(C_1-C_5)$alkoxy, a halogen atom or —$CF_3$;

$R_3$ takes any one of the meanings given above for $R'_1$ or $R'_2$ but does not represent —CHO;

$R_4$ represents a hydrogen atom or $(C_1-C_{15})$alkyl;

R is chosen from $(C_1-C_9)$alkoxy; phenyl; [sic] or phenylcarbonyl optionally substituted by a halogen atom, ($C_1$–$C_5$)alkyl, ($C_1$–$C_5$)alkoxy; [sic] —$CF_3$ or —$OCF_3$; a halogen atom; —$CF_3$; and —$OCF_3$; and p is 0, 1 or 2.

Better still, preference is given to the compounds in which:

X represent O;

A represents —$CH_2$—$CR_3R_4$— in which the unsubstituted methylene group is bonded to X;

$R'_1$ or $R'_2$ represents a hydrogen atom;

$R_3$ represents a hydrogen atom or a ($C_1$–$C_5$)alkyl group, such as methyl;

$R_4$ represents ($C_1$–$C_{15}$)alkyl, preferably ($C_1$–$C_5$)alkyl, such as methyl;

R is chosen from a halogen atom, $CF_3$, ($C_1$–$C_5$)alkoxy, phenyl and para-chlorobenzoyl;

p is 0, 1 or 2.

Mention may be made, as examples of such compounds, of:

3,3-dimethyl-5-formyl-7-bromo-2,3-dihydrobenzoxepine,
3,3-dimethyl-5-formyl-9-methoxy-2,3-dihydrobenzoxepine,
3,3-dimethyl-5-formyl-7,8-dichloro-2,3-dihydrobenzoxepine,
3,3-dimethyl-5-formyl-7-fluoro-8-chloro-2,3-dihydrobenzoxepine,
3,3-dimethyl-5-formyl-7-(para-chlorobenzoyl-2,3-dihydrobenzoxepine,
3,3-dimethyl-5-formyl-7-trifluoromethyl-2,3-dihydrobenzoxepine,
3,3-dimethyl-5-formyl-7-fluoro-2,3-dihydrobenzoxepine,
3,3-dimethyl-5-formyl-7-chloro-2,3-dihydro-benzoxepine,
3,3-dimethyl-5-formyl-7,8-dimethoxy-2,3-dihydrobenzoxepine,
3,3-dimethyl-5-formyl-7-phenyl-2,3-dihydrobenzoxepine,
3,3-dimethyl-5-formyl-2,3-dihydrobenzoxepine,
3,3-dimethyl-5-formyl-7-methoxy-2,3-dihydrobenzoxepine.

According to another of its aspects, the invention relates to the intermediate compounds of formula:

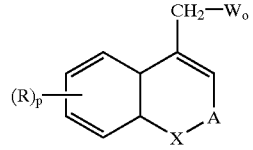

in which:

A represents the bivalent radical —$(CH_2)_s$—$CR_3R_4$—$(CH_2)_t$— where one of s and t represents 0 and the other 1;

$R_3$, $R_4$, R, p and X are as defined above for the formula (I); and $W_o$ represents —$CH_3$ or —$CH_2Br$.

Preference is given, among these compounds, to those in which:

$R_3$ represents H, ($C_1$–$C_{15}$)alkyl, ($C_1$–$C_{15}$)alkenyl [sic] or phenyl optionally substituted by ($C_1$–$C_5$)alkyl, ($C_1$–$C_5$) alkoxy, a halogen atom or —$CF_3$;

$R_4$ represents a hydrogen atom or ($C_1$–$C_{15}$) alkyl;

R is chosen from ($C_1$–$C_9$)alkyl; ($C_1$–$C_5$)alkoxy; phenyl; [sic] or phenylcarbonyl optionally substituted by a halogen atom, ($C_1$–$C_5$)alkyl, ($C_1$–$C_5$)alkoxy, —$CF_3$ or —$OCF_3$; a halogen atom; —$CF_3$; and —$OCF_3$; and p is 0, 1 or 2.

Better still, the meanings of $R_3$, $R_4$, R and p will be chosen from the following groups:

$R_3$ represents a hydrogen atom or a ($C_1$–$C_5$)alkyl group, such as methyl;

$R_4$ represents ($C_1$–$C_{15}$)alkyl, preferably ($C_1$–$C_5$)alkyl, such as methyl;

R is chosen from a halogen atom, $CF_3$, ($C_1$–$C_5$)alkoxy, phenyl and para-chlorobenzoyl;

p is 0, 1 or 2.

Examples of compounds in which $W_o$—$CH_3$ are represented in Table 4, which appears after the examples.

Mention may also be made of 3,3,5-trimethyl-7-methoxy-2,3-dihydrobenzoxepine.

Examples of compounds in which $W_o$=–$CH_2Br$ are represented in Table 5, which appears after the examples.

Mention may also be made of 3,3-dimethyl-5-bromomethyl-7methoxy-2,3-dihydrobenzoxepine.

The invention additionally relates to the intermediate compounds of formula (IIIb):

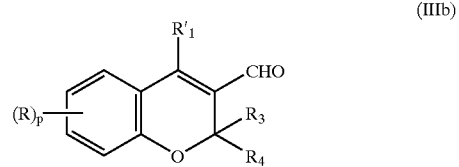

in which:

$R'_1$ represents a hydrogen atom, a ($C_1$–$C_5$)alkyl group or phenyl;

$R_3$ and $R_4$ are chosen independently from a hydrogen atom, a ($C_1$–$C_{18}$)alkyl group or a ($C_2$–$C_{18}$)alkenyl group.

Preference is given, among these compounds, to those in which $R'_1$ represents a hydrogen atom.

Mention may be made, as examples of:

-2,2-dimethyl-3-formyl-2H-1-benzopyran;
-2-[non-3-enyl]-3-formyl-2H-1-benzopyran;
-2-undecyl-3-formyl-2H-1-benzopyran;
-2-pentyl-3-formyl-2H-1-benzopyran;
-2-nonyl-3-formyl-2H-1-benzopyran;
-4-methyl-3-formyl-2H-1-benzopyran; and
-4-phenyl-3-formyl-2H-1-benzopyran.

The invention additionally relates to pharmaceutical compositions comprising a pharmaceutically effective amount of a compound of formula (I) as defined above in combination with one or more pharmaceutically acceptable vehicles.

These compositions can be administered orally in the form of immediate-release or controlled-release granules, hard gelatin capsules or tablets, intravenously in the form of an injectable solution, transdermally in the form of an adhesive transdermal device, or locally in the form of a solution, cream or gel.

A solid composition for oral administration is prepared by addition of a filler and, if appropriate, a binder, a disintegration agent, a lubricant, a colorant or a flavour enhancer to the active principle and by shaping or mixing as a tablet, a coated tablet, a granule, a powder or a capsule.

Examples of filters encompass lactose, maize starch, sucrose glucose, sorbitol, crystalline cellulose and silicon dioxide, and examples of binders encompass poly(vinyl alcohol), poly(vinyl ether), ethylcellulose, methycellulose [sic], acacia [sic], gum tragacanth, gelatin, shellac, hydroxypropylcellulose, hydroxypropylmethylcellulose [sic], calcium citrate, dextrin and pectin. Examples of lubricants encompass magnesium stearate, talc, polyethylene glycol, silica and hardened vegetable oils. The colorant can be any of those authorized for use in medicaments. Examples of flavour enhancers encompass cocoa powder, mint in herbal form, aromatic powder, mint in oil form, borneol and cinnamon powder. Of course, the table or the granule can be suitably coated with sugar, gelatin or the like.

An injectable form comprising the compound of the present invention as active principle is prepared, if appropriate, by mixing the said compound with a pH regulator, a buffer, a suspending agent, a solubilizing agent, a stabilizer, a tonicity agent and/or a preservative and by converting the mixture into a form for intravenous, subcutaneous or intramuscular injection, according to a conventional process. If appropriate, the injectable form obtained can be lyophilized by a conventional process.

Examples of suspending agents encompass methycellulose [sic], polysorbate 80, hydroxyethyl-cellulose, acacia [sic], gum tragacanth powder, sodium carboxymethylcellulose and polyethoxylated sorbitan monolaurate.

Examples of solubilizing agent [sic] encompass castor oil solidified with polyoxyethylene, polysorbate 80, nicotinamide, polyethoxylated sorbitan monolaurate and the ethyl ester of castor oil fatty acid.

In addition, the stabilizer encompasses sodium sulphite, sodium metasulphite and ether, while the preservative encompasses methyl p-hydroxybenzoate, ethyl p-hydroxybenzoate, sorbic acid, phenyl [sic], cresol and chlorocresol.

The invention is additionally targeted at the use of an active principle chosen from a compound of formula (I) as defined above in the preparation of a medicament intended to prevent or treat dyslipidaemias, atherosclerosis or diabetes.

The hypolipidaemic and hypoglycaemic activity of the compounds of the invention was demonstrated in vitro and in vivo by employing the following tests:

1) Demonstration of the in vitro activity.

The hypolipidaemic and hypoglycaemic effect of the compounds of the invention results from their ability to activate the PPARα and PPARγ isoforms.

Analysis of the activation of PPARα and PPARγ is based on the transfection of a DNA allowing the expression of a reporter gene (the gene of luciferase) under the control of the PPARs, either endogenous in the case of PPARγ of exogenous in the case of PPARα. The reporter plasmid J3TkLuc comprises three copies of the response element for PPARs of the human apo A-II gene (Staels, B et al. (1995), J. Clin. Invest., 95, 705–712) which are cloned upstream of the promoter of the thymidine kinase gene of the herpes simplex virus in the plasmid pGL3. This reporter gene was obtained by subcloning, in the plasmid pGL3, the plasmid J3TkCAT described above (Fajas, L et al. (1997), J. Biol. Chem., 272, 18779–18789). The cells used are green monkey CV1 cells transformed by the SV40 virus, which express PPARγ (Forman, B. et al. (1995), Cell, 83, 803–812), and human SK-Hep1 cells, which do not express PPARs. These cells were inoculated at the rate of 20,000 cells per well (96-well plates) and transfected with 150 ng of reporter DNA complexed with a mixture of lipids. In the case of the SK-Hep1 cells, an expression vector for PPARα, described by Sher, T. et al. (1993), Biochemistry, 32, 5598–5604, is cotransfected. After 5, hours, the cells are washed twice and incubated for 36 hours in the presence of the test compound in a fresh culture medium comprising 10% foetal calf serum. At the end of incubation, the cells are lysed and the luciferase activity is measured. This activity is expressed relative to the control value.

By way of example, the compound of Example 16b described below ((2E, 4E)-5-(3,3-dimethyl-7-methoxy-2,3-dihydrobenzoxepin-5-yl)-3-methylpenta-2,4-dienoic acid) increases, under these conditions, the luciferase signal by 300% in the CV1 cells and by 250% in the SK-Hep1 cells. In the presence of a pGL3 reporter vector devoid of a PPAR response element, the compound of Example 16b is inactive in both cell types.

2) Demonstration of the in vivo activity

The antidiabetic and hypolipidaemic activity of the compounds of formula I [sic] was determined by the oral route in db/db mice.

Two-month-old db/db mice are treated per os for 15 days with the compound of Example 16 (100 mg/kg/day). Each study group comprises seven animals. After treating for three days (D3) and fifteen days (D15), retro-orbital samples are taken after light anaesthesia and fasting for 4 hours.

The following measurements were taken:
quantitative determination of glycaemia (glucose oxidase) at D3 and D15 and of the lipid parameters with regard to the sera at D15 (COBAS): triglycerides, total cholesterol (CHOL), HDL cholesterol (HDL-C) and free fatty acids (FFA) (BioMérieux and Wako Chemicals quantitative determination kit).

The results obtained have been reported in the following table. The measurements which appear in this table are mean values±standard error.

|  | Control | Example 16 | % variation with respect to the control |
|---|---|---|---|
| Glycaemia D3 (mM) | 23.3 ± 4.4 | 15.4 ± 3.8* | −28 |
| Glycaemia D15 (mM) | 28.1 ± 4.2 | 16.7 ± 4.4* | −40 |
| Triglycerides D15 (mM) | 2.11 ± 0.62 | 0.69 ± 0.09* | −68 |
| CHOL D15 (mM) | 3.71 ± 0.37 | 4.44 ± 0.39* | +19 |
| HDL-C D15 (mM) | 2.96 ± 0.25 | 3.50 ± 0.37* | +18 |
| FFA (mM) | 1.01 ± 0.12 | 0.82 ± 0.23 (ns) | −20 |

Mann-Whitney test:
*p < 0.05 relative to the control;
ns: not significant.

These results unambiguously demonstrate the hypolipidaemic and antidiabetic activity of the compounds of the invention.

The following examples illustrate the invention without implied limitation.

The following abreviations have been used in the proton nuclear magnetic resonance (NMR) data: s for singlet, d for doubtlet, t for triplet, q for quartet, o for octet and m for mutiplet. The chemical shifts δ are expressed in ppm; M.p. represents the melting point and B.p. the boiling point.

EXAMPLE 1

(2E, 4E)-5-(2-Pentyl-2H-1-benzopyran-3-yl)-3-methylpenta-2,4-dienoic acid and ethyl ester (I: p=0; $R_1$=H; X=O; A=—$CR_3R_4$—; $R_3$=H; $R_4$ =$_n$—$C_5H_{11}$; $R_2$=Z; n=1; R'=—$CH_3$; and compound 1a [sic]:Y=—$OCH_2CH_3$;

compound 1b [sic]:Y=—OH).

a) 2-n-Pentyl-3-formyl-2H-1-benzopyran

A mixture of 22.0 g (0.18 mol) of salicylaldehyde, 25.0 g (0.198 mol) of 2-octenal and 24.8 g (0.18 mol) of potassium carbonate in 200 ml of dioxane, maintained under an inert atmosphere, is heated at reflux for 2.5 h. The reaction mixture is subsequently brought to room temperature (20–25° C.) and then diluted by addition of 1.5 litres of water. The formation of an oil is observed, which oil is extracted with methylene chloride. The organic phase is dried over anhydrous sodium sulphate and then concentrated under reduced pressure. The title compound is thus obtained in a form of an orange oil, which oil is distilled under reduced pressure (B.p. (0.44 mm Hg): 132–140° C.). 20 g of the title product are obtained by distillation (48% yield).

b) Ethyl ester of (2E, 4E)-5-(2-pentyl-2H-1-benzopyran-3-yl)-3-methylpenta-2,4-dienoic acid (compound 1a)

3 g (75.5 mmol) of sodium hydride, as a 60% suspension in oil, are added at 0° C. to a solution, maintained under an inert atmosphere, of 19.9 g (75.5 mmol) of the ethyl of diethyl (2-methyl-3-carboxypropyl-2-enyl)phosphonate in 200 ml of tetra-hydrofuran.

The combined mixture is allowed to react for 20 minutes at 0° C. and then for 15 minutes at room temperature (from 20 to 25° C.). 2 ml of DMPU (1,3-dimethyl-3,4,5,6-tetrahydro-2(1H)-pyrimidinone) are subsequently added to the reaction mixture. The reaction mixture is then cooled to 0° C. and a solution of 14.5 g (62.9 mmol) of 2-n-pentyl-3-formyl-2H-1-benzopyran in 145 ml of tetrahydrofuran is added at this temperature.

The combined mixture is allowed to react for 1 hour at 0° C. and then the excess sodium hydride is destroyed by addition of cold water (approximately 0° C.). Extraction is then carried out with ethyl acetate. The organic phase is washed with water and dried over sodium sulphate and then concentrated under reduced pressure. The title compound is obtained in the form of an oil, which oil is purified by flash chromatography using a 98/2 cyclohexane/ethyl actate mixture as elutent. 2.4 g of the 2Z isomer of the acid 1a [sic] and 7.5 g of the 2E isomer of the acid 1a [sic]are thus obtained.

Compound 2Z:

$^1$H NMR (CDCl$_3$, 300 MHz) δ (ppm): 0.8 (3H, m), 1.2–1.8 (11H, m), 2.0 (3H, s), 4.1 (2H, q, J=7 Hz), 5.2 (1H, m), 5.6 (1H, s), 6.4 (1H, s), 6.5 (1H, d, J=16 Hz), 6.8–7.1 (4H, m), 7.7 (1H, d, J=16 Hz).

Compound 2E:

$^1$H NMR (CDCl$_3$, 300 MHz) δ (ppm): 0.8 (3H, t, J=7 Hz), 1.2–1.8 (11H, m), 2.3 (3H, s), 4.1 (2H, q, J=7 Hz), 5.0 (1H, m), 5.8 (1H, s), 6.1 (1H, d, J=16 Hz), 6.4 (1H, s), 6.8–7.1 (4H, m).

c) (2E, 4E)-5-(2-Pentyl-2H-1-benzopyran-3-yl)-3-methylpenta-2,4-dienoic acid (compound 1b).

5.0 g (30.8 mmol) of sodium hydroxide, in solution in 100 ml of water, are added to a solution of 10.5 g (30.8 mmol) of the ethyl ester obtained in the preceding Stage b) in solution [sic] in 105 ml of methanol.

The reaction mixture is brought to reflux for 3 hours. It becomes clear.

The reaction mixture is then allowed to return to room temperature (20–25° C.) and the methanol is evaporated under reduced pressure. The residue is taken up in 600 of water and then the mixture is washed twice with diethyl ether. The aqueous phase is then acidified with a 5N aqueous hydrochloride acid solution. A pasty precipitate is formed and is extracted with methylene chloride. The organic phase is then dried over anhydrous sodium sulphate and then concentrated under reduced pressure. A pasty solid is thus obtained, which solid is recrystallized from 50 ml of methanol. The title compound is isolated in the form of a white solid (86% yield).

Compound 2E:

M.p.: 118–120° C.

$^1$H NMR (DMSO [sic], 300 MHz) δ (ppm): 0.88 (3H, t, J=7 Hz), 1.7–1.3 (8H, m), 2.3 (3H, s), 5.3 (1H, d, J=2.3 Hz), 6.0 (1H, s), 6.6 (1H, d, J=16 Hz), 7.2–6.8 (6H, m).

Compound 2Z:

M.p.: 161–163° C.

$^1$H NMR (d6-DMSO, 300 MHz) δ (ppm): 0.8 (3H, t, J=3 Hz), 1.8–1.2 (8H, m), 2.0 (3H, s), 5.1 (1H, d, J=10 Hz), 5.7 (1H, s), 6.5 (1H, s), 6.6 (1H, d, J=16 Hz), 7.1–6.8 (4H, m), 7.7 (1H, d, J=16 Hz).

EXAMPLE 2

(2E, 4E)-5-(2,2-Dimethyl-6-methoxy-2H-1-benzo-pyran-3-yl)-3-methylpenta-2,4-dienoic acid and ethyl ester (I: p=1; R=6—OCH$_3$; X=O; A=—CR$_3$R$_4$—; R$_3$=R$_4$ =—CH$_3$; R$_1$=Z; R$_2$ =H; n=1; R'=—CH$_3$; and compound 2a [sic]: Y=OCH$_2$CH$_3$;

compound 2b [sic]: Y=—OH).

a) 6-Methoxy-2,2-dimethylchroman-4-one 19.8 ml (1.6 equivalents) of pyrrolidine are added dropwise to a solution, cooled below 25° C., of 25 g (0.15 mol) of 2'-hydroxy-5'-methoxyacetophenone, 12.1 ml (1.1 equivalents) of acetone and 140 ml of toluene. The reaction mixture is left stirring for 16 hours at 25° C.

290 ml of acetone are then added and the reaction mixture is heated at reflux for 4 hours. It is subsequently concentrated under reduced pressure and then extracted with ethyl acetate. The organic phase is washed with a saturated aqueous sodium chloride solution, then a 1N sodium hydroxide solution and then with a 1N hydrochloride acid solution, and finally washed with water. The organic phase is then dried over anhydrous sodium sulphate and then concentrated under reduced pressure. The residue (an orange compound) is dissolved in diisopropyl ether. The insoluble material is filtered off and the organic phase is concentrated under reduced pressure. A brown paste is obtained, which paste is purified by flash chromatography using dichloromethane as eluent. 9.4 g of yellow oil are obtained.

$^1$H NMR (CDCl$_3$, 300 MHz) δ (ppm): 7.2 (1H, d, J=3.15 Hz), 7 (1H, d, J=3.17 Hz), 6.75 (1H, d, J=8.99 Hz), 3.7 (3H, s), 2.6 (2H, s), 1.35 (6H, s).

IR (cm$^{-1}$) 1638.4 b) 6-Methoxy-2,2,4-trimethylchroman-4-ol.

9.4 g (45.6 mmol) of 6-methoxy-2,2-dimethylchroman-4-one, dissolved in 150 ml of tetrahydrofuran, are added dropwise to a solution [sic], maintained under an inert atmosphere and brought to 50° C., of 33.5 ml (0.1 mol) of 3M methylmagnesium chloride in solution in tetrahydrofuran. The combined mixture is heated at reflux for 4 hours. The reaction mixture is subsequently cooled with an ice bath and hydrolysed by running in water dropwise. The reaction mixture is subsequently poured onto an ammonium chloride solution. After extracting with ethyl acetate, the organic phase is dried over anhydrous sodium sulphate and concentrated under reduced pressure. 10 g of the title compound are obtained.

IR (cm$^{-1}$) 3400–3500.

c) 6-Methoxy-2,2,4-trimethyl-2H-1-benzopyran.

A mixture of 10 g (0.045 mol) of 6-methoxy-2,2,4-trimethylchroman-4-ol, 0.25 g (1.45 mmol) of para-toluenesulphonic acid and 150 ml of toluene is heated at reflux for 4 hours in a 500 ml four-necked flask equipped with a Dean and Stark apparatus.

Once the solution has returned to room temperature (25° C.), the organic phase is washed with a sodium bicarbonate solution and then with water. The organic phase is dried over anhydrous sodium sulphate and then concentrated under reduced pressure. A dark oil is thus obtained: 9.4 g.

d) 4-Bromomethyl-6-methoxy-2,2-dimethyl-2H-1-benzopyran.

A solution of 9.1 g (0.045 mol) of 6-methoxy-2,2,4-trimethyl-2H-1-benzopyran, 8 g (0.045 mol) of N-bromosuccinimide and 0.25 g of α,α'-azobisisobutyronitrile in 100 ml of carbon tetrachloride is heated at reflux for 4 hours. The insoluble material is filtered off and then the organic solution is washed with tepid water (30° C.), then dried over anhydrous sodium sulphate and concentrated under reduced pressure. 13 g of a dark oil are thus obtained.

$^1$H NMR (CDCl$_3$, 300 MHz) δ (ppm): 6.6 to 6.85 (3H, m), 5.75 (1H, s), 4.15 (2H, s), 3.7 (3H, s), 1.3 (6H, s).

e) 6-Methoxy-4-formyl-2,2-dimethyl-2H-1-benzopyran.

A mixture of 12.7 g (0.045 mol) of 4-bromomethyl-6-methoxy-2,2-dimethyl-2H-1-benzopyran, 125 ml of chloroform and 8.8 g (0.059 mol) of hexamethylenetetramine is heated at reflux for 2 hours. The reaction mixture is subsequently concentrated under reduced pressure. An orange precipitate is obtained, which precipitate is taken up in a 75% aqueous acetic acid solution (133 ml). This solution is heated at reflux for 90 minutes, then 20 ml of concentrated hydrochloric acid are added to the solution and it is again heated at reflux for 30 minutes. 80 ml of water are added to this hot solution. The combined mixture is left standing at 25° C. for 30 minutes with stirring, it is then extracted with diethyl ether and the ethereal phase is dried over anhydrous sodium sulphate. The organic phase is then concentrated under reduced pressure. 8.6 g of the dark oil are thus obtained, which oil is purified by flash chromatography using dichloromethane as eluent. 2.7 g of a yellow oil are isolated.

IR (cm$^{-1}$) 1696.3, 1487, 1261.

$^1$H NMR (CDCl$_3$, 300 MHz) δ (ppm): 9.6 (1H, s), 7.75 (1H, s), 6.7 (2H, s), 6.4 (1H, s), 3.75 (3H, s), 1.4 (6H, s).

f) Ethyl ester of (2E, 4E)-5-(2,2-dimethyl-6-methoxy-2H-1-benzopyran-3-yl)-3-methylpenta-2,4-dienoic acid (compound 2a).

A solution of 3 ml (12.3 mmol) of the ethyl ester of diethyl (2-methyl-3-carboxyprop-2-enyl)-phosphonate (41% trans) in 20 ml of tetrahydrofuran is added to a solution, maintained under an inert atmospher, of 1.38 g (12.3 mmol) of potassium tert-butoxide and 20 ml of tetrahydrofuran (exothermic reaction). The reaction mixture is left stirring for 1 hour and is then cooled to 10° C. 2.7 g (12.3 mmol) of 6-methoxy-4-formyl-2,2-dimethyl-2H-1-benzopyran in 20 ml of tetrahydrofuran are added to the solution. The combined mixture is left stirring for 16 hours at 25° C. and is then cooled, and water is added thereto. The reaction mixture is extracted with diethyl ether. The organic phase is then dried over anhydrous sodium sulphate and then concentrated under reduced pressure. 4 g of an orange oil are obtained, which oil is purified by flash chromatography using a mixture of cyclohexane and diisopropyl ether as eluent. 1.9 g of a yellow oil are obtained.

$^1$H NMR (CDCl$_3$, 300 MHz) δ (ppm): 6.8–6.5 (5H, m), 5.8 (2H, s), 4.1 (2H, q), 3.7 (3H, s), 2.3 (3H, s), 1.3 (6H, s), 1.2 (3H, m).

g) (2E, 4E)-5-(2,2-Dimethyl-6-methoxy-2H-1-benzopyran-3-yl)-3-methylpenta-2,4-dienoic acid (compound 2b)

A solution of 1.9 g (5.7 mmol) of the ethyl ester obtained in the preceding Stage f), 30 ml of methanol, 0.3 g (1.3 equivalents) of sodium hydroxide and 10 ml of water is heated at reflux for 2 h. The reaction mixture is then concentrated under reduced pressure and the residue is taken up in water. The combined mixture is acidified with a 1N aqueous hydrochloric acid solution. The precipitate formed (yellow) is firstly filtered off, then washed with water and dried under reduced pressure. 1.3 g of the title compound are isolated in the solid form. M.p=140° C.

IR (cm$^{-1}$) 1685, 1602, 1487, 1266

$^1$H NMR (CDCl$_3$, 300 MHz) δ (ppm): 6.55 to 6.8 (5H, m), 5.8 (2H, 2s), 3.7 (3H, s), 2.35 (3H, s), 1.4 (6H, s)

Microanalysis:

Theoretical: C=72%, H=6.66%, O=21.33%

Calculated: C=71.74%, H=6.81%, O=20.76%

EXAMPLES 3 TO 14

By using the processes illustrated in the preceding Examples 1 and 2, The compounds of Examples 3 to 14 which follow (where Et denotes ethyl, Ph denotes phenyl and TFA denotes trifluoracetic acid) are synthesized.

TABLE 1

| Example | Chemical formula | Characterization physicochemical data |
|---|---|---|
| 3a | | M.p. = 110–112° C. |
| 3b | | M.p. = 226–228° C.<br>$^1$H NMR (d6-DMSO, 300 MHz) δ (ppm):<br>2.4(3H, s), 5.2(2H, s), 6.0(1H, s), 6.6(1H, d, J=16Hz),<br>7.1–6.9(4H, m), 7.3–7.2(2H, m). |

TABLE 1-continued

| Example | Chemical formula | Characterization physicochemical data |
|---|---|---|
| 4a | | $^1$H NMR (CDCl$_3$, 300 MHz) δ (ppm): 1.52(3H, t, J=7.1Hz), 1.74(6H, s), 2.56(3H, d, J=1.1Hz), 4.41(2H, q, J=7.1Hz), 6.09(1H, s), from 6.66 to 7.36(7H, m). |
| 4b | | M.p. = 164–166° C.<br>$^1$H NMR (CDCl$_3$, 300 MHz) δ ppm:<br>1.38(6H, s), 2.5(3H, s), 6.03(1H, s), 6.68–7.26(7H, m). |
| 5a | | $^1$H NMR (CDCl$_3$, 300 MHz) δ (ppm):<br>1.41(3H, t, J=7.14Hz), 1.68(6H, s), 2.16(3H, d, J=1.2Hz),<br>4.3(2H, q, J=7.13Hz), 5.82(1H, s), 6.58(1H, d, J=16.35 Hz),<br>from 6.79 to 7.24(5H, m), 8.3(1H, d, J=16.2Hz). |
| 5b | | M.p. = 176° C.<br>$^1$H NMR (CDCl$_3$, 300 MHz) δ (ppm):<br>1.81(6H, s), 2.35(3H, s), 6(1H, s), 6.77(1H, d, J=16.2Hz),<br>6.93(1H, s), from 7.02 to 7.4(4H, m), 8.37(1H, d, J=16.2Hz). |
| 6a | | $^1$H NMR (CDCl$_3$, 300 MHz) δ (ppm):<br>0.8(3H, t, J=7Hz), 1.2–2.3(15H, m), 2.3(3H, s),<br>4.1(2H, q, J=7Hz), 5.0(1H, d, J=14Hz), 5.3–5.4(2H, m),<br>5.8(1H, s), 6.1(1H, d, J=16Hz), 6.4(1H, s),<br>6.5(1H, d, J=16Hz), 6.8–7.1(4H, m). |
| 6b | | M.p. = 120–122° C.<br>$^1$H NMR (CDCl$_3$, 300 MHz) δ (ppm):<br>0.8(3H, t, J=6.5Hz), 2.3–0.8(12H, m), 2.3(3H, s),<br>5.1(1H, d, J=10Hz), 5.4–5.3(2H, m), 5.8(1H, s),<br>6.2(1H, d, J=16Hz), 6.5(1H, s), 6.6(1H, d, J=16Hz),<br>7.1–6.8(4H, m). |
| 7a | | $^1$H NMR (CDCl$_3$, 300 MHz) δ (ppm):<br>1.2(3H, m), 2(3H, s), from 4.04 to 4.14(2H, m),<br>5(2H, s), 5.7(1H, s), 6.1(1H, d, J=16.3Hz),<br>from 6.47 to 7.39(10H, m). |
| 7b | | M.p. = 258–260° C.<br>$^1$H NMR (d6-DMSO, 300 MHz) δ (ppm):<br>1.73(3H, s), 3.125(1H, TFA exchangeable), 4.89(2H, s),<br>5.67(1H, s), from 6.26 to 6.49(3H, m),<br>from 6.63 to 6.73(2H, m), from 6.97 to 7.03(3H, m),<br>from 7.25 to 7.31(3H, m). |
| 8a | | $^1$H NMR (CDCl$_3$, 300 MHz) δ (ppm):<br>0.6–1.6(22H, m), 2.3(3H, s), 4.1(2H, q, J=7Hz),<br>4.9(2H, s), 5.8(1H, s), 6.1(1H, d, J=16Hz),<br>6.5(1H, s), 6.6(1H, d, J=16Hz), 6.7–7.0(4H, m). |

TABLE 1-continued

| Example | Chemical formula | Characterization physicochemical data |
|---|---|---|
| 8b | nC₉H₁₉-chromene-CH=CH-C(CH₃)=CH-COOH | M.p. = 161–164° C.<br>¹H NMR (CDCl₃, 300 MHz) δ (ppm):<br>0.5–1.6(19H, m), 2.3(3H, s), 4.9(2H, s), 5.9(1H, s),<br>6.1(1H, d, J=16Hz), 6.6(1H, s), 6.7–6.6(2H, m),<br>7.1–6.8(2H, m). |
| 9a | Ph-chromene-CH=CH-C(CH₃)=CH-COOEt | ¹H NMR (CDCl₃, 300 MHz) δ (ppm):<br>0.8(3H, m), 2.3(3H, s), 4.1(2H, m), 5.0(2H, s),<br>5.8(1H, s), 6.1(1H, d, J=16Hz), 6.5–6.7(2H, m),<br>6.8–6.9(1H, m), 7.1–7.5(7H, m). |
| 9b | Ph-chromene-CH=CH-C(CH₃)=CH-COOH | ¹H NMR (d6-DMSO, 300 MHz) δ (ppm):<br>2.1(3H, s), 4.9(2H, s), 5.8(1H, s),<br>6.34(1H, d, J=16Hz), 6.8–6.6(3H, m), 7.5–7.2(7H, m). |
| 10a | chromene(2-N-C₉H₁₉)-CH=CH-C(CH₃)=CH-COOEt | ¹H NMR (CDCl₃, 300 MHz) δ (ppm):<br>0.8(3H, t, J=7Hz), 1.2–1.7(19H, m),<br>2.3(3H, s), 4.1(2H, q, J=7Hz), 5.0(1H, d, J=10Hz),<br>5.8(1H, s), 6.1(1H, d, J=16Hz), 6.4(1H, s),<br>6.6(1H, d, J=16Hz), 6.8–7.2(4H, m). |
| 10b | chromene(2-N-C₉H₁₉)-CH=CH-C(CH₃)=CH-COOH | M.p. = 104–106° C.<br>¹H NMR (CDCl₃, 300 MHz) δ (ppm):<br>0.8(3H, m), 1.8–1.2(16H, m), 5.0(1H, d, J=8Hz),<br>5.8(1H, s), 6.2(1H, d, J=16Hz), 6.5(1H, s),<br>6.6(1H, d, J=16Hz), 6.9–6.8(2H, m), 7.1–7.0(2H, m). |
| 11a | 4-methylchromene-CH=CH-C(CH₃)=CH-COOEt | ¹H NMR (CDCl₃, 300 MHz) δ (ppm):<br>1.2(3H, t, J=7Hz), 2.0(3H, s), 2.3(3H, s),<br>4.1(2H, q, J=7Hz), 4.8(2H, s), 5.8(1H, s),<br>6.1(1H, d, J=16Hz), 6.8–7.2(5H, m). |
| 11b | 4-methylchromene-CH=CH-C(CH₃)=CH-COOH | M.p. = 216–218° C.<br>¹H NMR (CDCl₃, 300 MHz) δ (ppm):<br>2.15(3H, s), 2.3(3H, s), 4.8(2H, s), 5.8(1H, s),<br>6.2(1H, d, J=16Hz), 6.9–6.8(2H, m), 7.3–7.0(3H, m). |
| 12a | chromene-CH=CH-C(CH₃)=CH-COOEt (Z) | ¹H NMR (CDCl₃, 300 MHz) δ (ppm):<br>1.2(3H, t, J=7Hz), 2.0(3H, s), 4.1(2H, q, J=7Hz),<br>5.0(2H, s), 5.7(1H, s), 6.5(1H, s), 6.6(1H, d, J=16Hz),<br>6.7–7.2(4H, m), 7.7(1H, d, J=16Hz). |
| 12b | chromene-CH=CH-C(CH₃)=CH-COOH (Z) | M.p. = 224–226° C.<br>¹H NMR (d6-DMSO, 300 MHz) δ (ppm):<br>2.1(3H, s), 5.0(2H, s), 5.8(1H, s), 7.0–6.8(4H, m),<br>7.2–7.18(2H, m), 7.7(1H, d, J=16Hz). |

TABLE 1-continued

| Example | Chemical formula | Characterization physicochemical data |
|---|---|---|
| 13a | [structure with n-C₁₁H₂₃, OEt] | ¹H NMR (CDCl₃, 300 MHz) δ (ppm):<br>0.8(3H, t, J=7Hz), 1.2–1.8(23H, m), 2.3(3H, s),<br>4.1(2H, q, J=7Hz), 5.0(1H, d, J=10Hz), 5.8(1H, s),<br>6.1(1H, d, J=16Hz), 6.4(1H, s), 6.6(1H, d, J=16Hz),<br>6.8–7.1(4H, m). |
| 13b | [structure with n-C₁₁H₂₃, OH] | M.p. = 115–117° C.<br>¹H NMR (CDCl₃, 300 MHz) δ (ppm):<br>0.8(3H, t, J=6.5Hz), 1.8–1.2(20H, m), 2.3(3H, s),<br>5.0(1H, d, J=10Hz), 5.8(1H, s), 6.2(1H, d, J=16Hz),<br>6.5(1H, s), 6.6(1H, d, J=16Hz), 6.8(2H, m),<br>7.0(1H, d, J=8Hz), 7.1(1H, t, J=8Hz). |
| 14a | [structure with Ph, OEt] | ¹H NMR (CDCl₃, 300 MHz) δ (ppm):<br>1.2(3H, t, J=7Hz), 2.2(3H, s), 4.1(2H, q, J=7Hz),<br>5.6(1H, s), 6.0(1H, d, J=6Hz), 6.1(1H, s),<br>6.7(1H, d, J=6Hz), 6.8(1H, s), 6.8–7(9H, m). |
| 14b | [structure with Ph, OH] | M.p. = 200–202° C.<br>¹H NMR (d6-DMSO, 300 MHz) δ (ppm):<br>2.2(3H, s), 5.8(1H, s), 6.36(1H, s), 6.4(1H, d, J=16Hz),<br>6.8(1H, d, J=8Hz), 7.4–6.9(10H, m). |

EXAMPLE 15

(2E, 4E)-5-(5-Methyl-2,3-dihydrobenzoxepin-4-yl)-3-methylpenta-2,4-dienoic acid (I: p=0; $R_1$=—$CH_3$; X=O; A=—$CH_2$—$CH_2$—; $R_2$=Z; n=1; R' [lacuna]—$CH_3$; and compound 15a [sic]: Y=—O—$CH_2$—$CH_3$;
compound 15b [sic]: Y=—OH).

a) 5-Methyl-2,3,4,5-tetrahydrobenzoxepin-5-ol

A solution [sic], maintained under an inert atmosphere, of 33.5 ml (0.1 mol) of 3M methylmagnesium chloride in solution in tetrahydrofuran is heated to 50° C. 11.3 g (0.069 mol) of 3,4-dihydro-2H-benzoxepin-5-one, dissolved in 150 ml of tetrahydrofuran, are added fairly quickly. This solution is brought to reflux for 4 hours and is then left stirring overnight at room temperature. The reaction mixture is subsequently gently hydrolysed with water under cold conditions. An ammonium chloride solution (120 g per litre) is then poured into the reaction mixture. The latter is extracted with ethyl acetate and then the organic phase is dried over anhydrous sodium sulphate and concentrated under reduced pressure. 14.7 g of a yellow oil are obtained, which oil is purified by crystallization from isooctane. 11.9 g of the title compound are thus obtained, the melting point of which is 92° C.

¹H NMR (CDCl₃, 300 MHz) δ (ppm): 7.5 (1H, d, J=1.73 Hz), 7.2 to 7 (3H, m), 4.15–3.9 (2H, m), 2.5 (1H, s), 2.1 (2H, m), 1.95 (2H, m), 1.6 (3H, s).

b) 5-Methyl-2,3-dihydrobenzoxepine 14.9 g (0.1 mol) of 5-methyl-2,3,4,5-tetrahydrobenzoxepin-5-ol, 300 ml of toluene and a spatula tip of para-toluenesulphonic acid are charged to a 1 litre reactor equipped with a Denan and Stark apparatus. The combined solution is brought to reflux for 2 hours, the water being removed as it is formed. The reaction mixture is then neutralized with a 5% aqueous sodium bicarbonate solution and the organic solution is washed with water. The organic phase is subsequently dried over anhydrous sodium sulphate and concentrated under reduced pressure. 16 g of the title compound are obtained, which compound is purified by distillation, B.p. (2.5 mm Hg)=80–90° C. 10 g of a colourless liquid are obtained.

¹H NMR (CDCl₃, 300 MHz) δ (ppm): 7.3–6.9 (4H, m), 5.9 (1H, m), 4.15 (2H, t), 2.4 (2H, m), 2.05 (3H, s).

c) 5-Methyl-4-formyl-2,3-dihydrobenzoxepine.

24 ml of dimethylformamide are run onto 150 ml of acetonitrile under an inert atmosphere in a 500 ml four-necked flask. The solution is cooled to 0° C. and then 28.8 ml of phosphorus oxychloride are added to the solution. The reaction mixture is subsequently left stirring at 5° C. for 20 minutes. A solution of 8.2 g (0.051 mol) of 5-methyl-2,3-dihydrobenzoxepine in 24 ml of dimethylformamide and 20 ml of acetonitrile is subsequently added to the reaction mixture. The temperature is allowed to gently rise to room temperature and then the reaction mixture is heated to 60° C. It is subsequently left stirring for 16 hours after heating has been halted. The reaction mixture is then brought to reflux and treated with ice-cold water. The combined mixture is neutralized with sodium hydroxide and then extracted with ethyl acetate. The organic phase is washed three times with an aqueous solution [lacuna] and then dried over anhydrous sodium sulphate and concentrated under reduced pressure. The product obtained is purified by flash chromatography using dichloromethane as eluent. 4 g of the title compound are obtained.

¹H NMR [CDCl₃, 300 MHz) δ (ppm): 10:45 (1H, s), 7.25–7.5 (4H, m), 4.6 (2H, m), 2.7 (5H, s+m).

d) Ethyl ester of (2E, 4E)-5-(5-methyl-2,3-dihydrobenzoxepin-4-yl)-3-methylpenta-2,4-dienoic acid (compound 15a).

A solution of 2.3 g (0.02 mol) of potassium tert-butoxide in 40 ml of tetrahydrofuran in a 250 ml four-necked flask is brought to 50° C. under an inert atmosphere. A solution of 6.1 ml (0.02 mol) of the ethyl ester of diethyl (2-methyl-3-carboxyprop-2-enyl)phosphonate in 20 ml of tetrahydrofuran is subsequently added to the solution, which solution is maintained under an inert atmosphere. The reaction mixture is left stirring at 50° C. for 20 minutes. The combined mixture is then cooled to 0° C. and a solution of 4 g (0.02 mol) of 5-methyl-4-formyl-2,3-dihydrobenzoxepine in 20 ml of tetrahydrofuran is added dropwise to the reaction mixture. The reaction is left stirring at room temperature (20–25° C.) for 16 hours. After cooling, water is run into the reaction mixture, which mixture is extracted with ethyl acetate. The organic phase is dried over anhydrous sodium sulphate and concentrated under reduced pressure. 7.2 g of an orange oil are obtained, which oil is purified by flash chromatography using an 80/20 cyclohexane/diisopropyl ether mixture as eluent. 3.4 g of the title compound are thus obtained.

$^1$H NMR (CDCl$_3$, 300 MHz) δ (ppm): 7.25–7 (5H, m), 6.3 (1H, d, J=15.78 Hz), 5.8 (1H, s), 4.4 (2H, m), 4.1 (2H, m), 2.35 (5H, m+s), 2.2 (3H, s), 1.2 (3H, t).

e) (2E, 4E-5-(5-Methyl-2,3-dihydrobenzoxepin-4-yl)-3-methylpenta-2,4-dienoic acid (compound 15b).

0.7 g (0.0175 mol) of sodium hydroxide, dissolved in 60 ml of water, is added to a solution of 3.4 g (0.011 mol) of the ethyl ester obtained in the preceding Stage d) in 60 ml of methanol. The reaction mixture is brought to reflux for 2 hours. The reaction mixture is then concentrated under reduced pressure. The residue is taken up in water (insoluble). The combined mixture is acidified with a 5N hydrochloric acid solution. The precipitate formed is then filtered off and washed with water and then dried. Recrystallization from ethanol results in 1.5 g of the title compound, the melting point of which is 199–202° C.

IR (cm$^{-1}$): acidic peak at 2500–3000, 1674.

$^1$H NMR (DMSO [sic], 300 MHz): 7.3 to 6.9 (5H, m), 6.5–6.6 (1J [sic], d, J=15.81 Hz), (1H, s), 4.3 (2H, t), 2.4 (2H, t), 2.25 (3H, s), 2.1 (3H, s).

EXAMPLE 16

(2E, 4E)-5-(3,3-Dimethyl-7-methoxy-2,3-dihydrobenzoxepin-5-yl)-3-methylpenta-2,4-dienoic acid (I: p=1; R=7—O—CH$_3$; X=O; A=—CH$_2$—CR$_3$R$_4$—; R$_3$=R$_4$=—CH$_3$; R$_2$=H; R$_1$=Z; n=1; R'=—CH$_3$; and compound 16a [sic]: Y=—O—CH$_2$CH$_2$;

compound 16b [sic]: Y=—OH].

a) 3-(4-para-Methoxyphenoxy)-2,2-dimethyl-propan-1-ol.

A solution of 391 g (1.19 mol) of potassium [3-(4-para-methoxyphenoxy)-2,2-dimethylpropane]sulphonate in 1.69 litres of water is heated at 50° C. for 15 minutes in order to obtain complete dissolution of the sulphonate.

156 ml of concentrated hydrochloric acid (1.5 equivalents) are added dropwise to this solution, which is then brought to reflux for 2.5 hours. A precipitate is formed by cooling the reaction mixture in an ice bath, which precipitate is dissolved by addition of diethyl ether. The organic phase is washed with water and then dried over anhydrous sodium sulphate. After filtering, the organic phase is concentrated under reduced pressure, 241.2 g of the title compound are thus obtained (yield=96%), the melting point of which is 68° C.

$^1$H NMR (CDCl$_3$, 300 MHz) δ (ppm): 7.05 (4H, s), 4 (3H, s), 3.97 (2H, s), 3.8 (2H, s), 2.35 (1H, s), 1.25 (6H, s).

IR (cm$^{-1}$): 3350–3250, 2995, 1520, 1470.

b) 3-(4-para-Methoxyphenoxy)-2,2-dimethylpropyl methanesulphonate.

191.5 ml (1.38 mol) of triethylamine are added to a solution, maintained between −10° C. and 0° C., of 241 g (1.15 mol) of the alcohol prepared in the above Stage a) in 700 ml of toluene. 100 ml (1.265 mol) of methanesulphonyl chloride are added to this solution, the temperature being maintained below 10° C.

After reacting for 2 hours, 550 ml of normal hydrochloric acid are added and extraction is carried out with ethyl acetate. The organic phase is washed with a saturated aqueous sodium chloride solution and then dried over anhydrous sodium sulphate. The organic phase is subsequently filtered and concentrated under reduced pressure. 321 g of an orange oil are obtained, which oil crystallizes at room temperature and has a melting point of 78° C. (96% yield).

$^1$H NMR (CDCl$_3$, 300 MHz) δ (ppm): 6.75 (4H, s), 4.1 (2H, s), 3.7 (3H, s), 3.6 (2H, s), 2.85 (3H, s), 1.05 (6H, s).

c) 4-(4-para-Methoxyphenoxy)-3,3-dimethylbutyronitrile.

40 g (1.5 equivalents) of sodium cyanide are added to a solution of 160.8 g (0.557 mol) of the methanesulphonate prepared in the above Stage b) dissolved in 600 ml of dimethyl sulphoxide. The solution is brought to 150° C. and maintained at this temperature for 3 hours and then the reaction mixture is allowed to return to room temperature over 16 hours. The reaction mixture is then cooled in an ice bath and then water is added. A precipitate appears and is extracted with ethyl acetate. The organic phase is washed twice with 400 ml of an aqueous sodium hydroxide solution (5 g per litre) and dried over anhydrous sodium sulphate. The organic phase is subsequently concentrated under reduced pressure and results in 122 g of an orange oil, which oil crystallizes (100% yield) and has a melting point of 64° C.

$^1$H NMR (CDCl$_3$, 300 MHz) δ (ppm): 6.75 (4H, s), 3.7 (3H, s), 3.6 (2H, s), 2.4 (2H, s), 1.15 (6H, s).

d) 4-(4-para-Methoxyphenoxy)-3,3-dimethylbutyric acid.

A solution of 47 g (0.215 mol) of the compound obtained in the preceding Stage c), 41.3 g (4 equivalents) of potassium hydroxide and 280 ml of ethylene glycol is brought to 150° C. for 3.75 hours. After cooling, water is run into the reaction mixture and extraction is carried out with diethyl ether. The aqueous phase is acidified with 5N hydrochloric acid to pH 1 with stirring. The precipitate is filtered off and washed with H$_2$O and then extracted with methylene chloride. The organic phase is dried over anhydrous sodium sulphate and then concentrated under reduced pressure. 37 g of an orange oil are obtained, which oil crystallizes at room temperature and has a melting point of 66° C. (73% yield).

IR (cm$^{-1}$): acidic peak at 1695.

$^1$H NMR (CDCl$_3$, 300 MHz) δ (ppm): 6.7 (4H, s), 3.6 (3H, s), 3.55 (2H, s), 2.3 (2H, s), 1 (6H, s).

e) 7-Methoxy-3,3-dimethyl-3,4-dihydro-2H-benzoxepin-5-one.

A solution of 900 g of polyphosphoric acid in 1.1 litres of toluene is brought to 90° C. 200 g (0.839 mol) of 4-(4-para-methoxyphenoxy)-3,3-dimethylbutyric acid, dissolved in 550 ml of toluene, are added to this solution. The combined mixture is kept stirring at 90° C. for 4 hours. The reaction mixture is then cooled to room temperature (20–25° C.). The thick oil is separated from the toluene. After cooling, the oil is taken up in 500 ml of ice-cold water and extracted with ethyl acetate. The organic phase is washed with 500 ml of a (1N) aqueous sodium hydroxide solution and then with 500 ml of water. The organic phase is dried over anhydrous sodium sulphate. The ethyl acetate and the toluene are evaporated under reduced pressure. 165 g of a yellow oil are obtained, overall yield: 89%.

IR (cm$^{-1}$) 2960, 1680, 1489, 1462, 1419.

$^1$H NMR (CDCl$_3$, 300 MHz) δ (ppm): 7.1 (1H, m), 6.95 (2H, s), 3.7 (2H, s), 3.65 (3H, s), 2.6 (2H, s), 1.05 (6H, s).

f) 7-Methoxy-3,3,5-trimethyl-2,3,4,5-tetrahydrobenzoxepin-5-ol.

190 ml (0.57 mol) of 3M methylmagnesium chloride in solution in tetrahydrofuran are charged to a 2 litre reactor maintained under an inert atmosphere. The solution is brought to 50° C. and then 82 g (0.372 mol) of the ketone prepared in the preceding Stage e), dissolved in 1.1 litres of tetrahydrofuran, are rapidly added thereto. The solution obtained is heated at reflux for 4 hours. The reaction mixture is subsequently cooled in an ice bath and then water is added thereto. The combined mixture is then poured onto a saturated aqueous ammonium chloride solution. Extraction is carried out with ethyl acetate and the organic phase is separated by settling and then dried over anhydrous sodium sulphate. This organic phase is concentrated under reduced pressure and results in 85 g of an orange oil, which oil crystallizes at room temperature (96% yield).

$^1$H NMR (CDCl$_3$, 300 MHz) [lacuna] 7.05–6.6 (3H, m), 3.7 (5H, s), 2.15 (1H, s), 1.8 (2H, d), 1.55 (3H, s), 1.05 (3H, s), 1 (3H, s).

g) 7-Methoxy-3,3,5-trimethyl-2,3-dihydrobenzoxepine.

169 g 0.716 mol) of the compound prepared in the preceding Stage f) in 2.25 litres of toluene and 5 g of para-toluenesulphonic acid are introduced into a 4 litre reactor equipped with a Dean and Stark apparatus. The combined mixture is brought to reflux for 4 hours. The water formed is removed as it is formed. 11.5 ml of water are thus removed. The reaction mixture is allowed to return to room temperature. The reaction mixture is poured into a 5% aqueous sodium bicarbonate solution. Separation by settling is allowed to take place and then the organic phase is washed with water and dried over anhydrous sodium sulphate. The organic phase is subsequently concentrated under reduced pressure. 155 g of a dark oil are obtained. Yield: 99%.

$^1$H NMR (CDCl$_3$, 300 MHz) δ (ppm): 6.9–6.6 (3H, m), 5.6 (1H, s), 3.7 (5H, 2s), 2.05 (3H, s), 1.05 (6H, s).

h) 5-Bromomethyl-7-methoxy-3,3-dimethyl-2,3-dihydrobenzoxepine.

155 g (0.71 mol) of the compound prepared in the preceding stage, 130 g (0.73 mol) of N-bromosuccinimide and 4 g of α,α'-azobisisobutyronitrile are introduced into 1.6 litres of carbon tetrachloride. The solution is brought to reflux for 4 hours and is then cooled to 25° C. The solid formed is filtered off and the organic phase is washed several times with tepid water (30–40° C.). Separation is carried out by settling and then the organic phase is dried over anhydrous sodium sulphate and concentrated under reduced pressure. 210 g of a brown oil are thus obtained, which oil corresponds to the title product.

$^1$H NMR (CDCl$_3$, 300 MHz) δ (ppm): 7.1–6.7 (3H, m), 6 (1H, s), 4.3 (2H, s), 3.75 (5H, s), 1.1 (6H, s).

i) 7-Methoxy-5-formyl-3,3-dimethyl-2,3-dihydrobenzoxepine.

210 g (0.71 mol) of the compound prepared in the preceding Stage (h) and 150 g (1.5 equivalents) of hexamethylenetetramine are introduced into 2 litres of chloroform. The solution is brought to reflux for 2 hours. The reaction mixture is subsequently concentrated under reduced pressure. The brown residue obtained is then taken up in 2.55 litre [sic] of a 75% aqueous acetic acid solution. The combined mixture is heated at reflux for 90 minutes, 385 ml of concentrated hydrochloric acid are then added thereto and the combined mixture is again heated at reflux for 30 minutes. Water is added under warm conditions to the reaction mixture. The combined mixture is again [sic] left for 30 minutes at room temperature (20–25° C.) and then extraction is carried out with ethyl acetate. The organic phase is separated by settling, then washed with an aqueous sodium bicarbonate solution, then dried over anhydrous sodium sulphate and concentrated under reduced pressure. 140 g of a dark-brown oil are thus obtained, which oil is purified by flash chromatography using dichloromethane as eluent. After purification, 98 g of the title compound are isolated. Yield: 60%

$^1$H NMR (CDCl$_3$, 300 MHz) δ (ppm): 9.5 (1H, s), 7.6 (1H, s), 6.9 (1H, d), 6.7 (1H, d, J=8.85 Hz), 6.48 (1H, s), 3.82 (2H, s), 3.37 (3H, s), 1.18 (6H, s).

j) Ethyl ester of (2E, 4E)-5-(3,3-dimethyl-7-methoxy-2,3-dihydrobenzoxepin-5-yl)-3-methylpenta-2,4-dienoic acid (compound 16a).

64.5 ml (0.263 mol) of the ethyl ester of diethyl (2-methyl-3-carboxyprop-2-enyl)phosphonate (41% trans) in 250 ml of tetrahydrofuran are added dropwise to a solution of 29.6 g (0.263 mol) of potassium tert-butoxide in 500 ml of tetrahydrofuran. The reaction mixture is left stirring for 1 hour, is then cooled in an ice bath and 43 g (0.185 mol) of the compound prepared in the preceding Stage i), dissolved in 250 ml of tetrahydrofuan, are added thereto dropwise. The reaction mixture is again left stirring at 25° C. for 16 hours, following which the reaction mixture is cooled in an ice bath and then hydrolysed by addition of water. Extraction is subsequently carried out with ethyl acetate and then the organic phase is dried over anhydrous sodium sulphate and concentrated under reduced pressure. 88 g of a dark-orange oil are thus obtained, which oil is purified by flash chromatography using a cyclohexane/diisopropyl ether mixture as eluent. 46.8 g of a yellow oil are thus isolated.

$^1$H NMR (CDCl$_3$, 300 MHz) δ (ppm): 6.9 (1H, d, J=2.95 Hz), 6.7–6.6 (3H, m), 6.35 (1H, d, J=15.42 Hz), 6 (1H, s), 5.8 (1H, s), 4.1 (2H, m), 3.8 (2H, s), 3.7 (3H, s), 2.3 (3H, s), 1.25 (3H, m), 1.08 (6H, s).

k) (2E, 4E)-5-(3,3-Dimethyl-7-methoxy-2,3-dihydrobenzoxepin-5-yl)-3-methylpenta-2,4-dienoic acid (compound 16b).

7.2 g (0.18 mol) of sodium hydroxide, dissolved in 500 ml of water, are added to a solution of 46 g (0.134 mol) of the compound prepared in the preceding Stage j) in 500 ml of methanol. This mixture is brought to reflux for 4 hours and then the reaction mixture is concentrated under reduced pressure. The paste obtained as residue is dissolved in diethyl ether and then washed with water. The aqueous phase is then acidified with 5N hydrochloric acid to pH 1. A yellow residue is obtained, which residue is dissolved in methylene chloride. The organic phase is dried over anhydrous sodium sulphate and concentrated under reduced pressure. 44 g of an oil are obtained, which oil is recrystallized from ethanol. 18 g of the title compound are thus isolated.

IR (cm$^{-1}$): 3000, 2900, 1680, 1599, 1271, acidic peak between 2400 and 2800.

$^1$H NMR (CDCl$_3$, 300 MHz) δ (ppm): 7.1 (1H, d, J=8.64 Hz), 7 to 6.85 (3H, m), 6.65 (1H, d, J=15.36 Hz), 6.2 (1H, s), 6 (1H, s), 4.05 (2H, s), 3.95 (3H, s), 2.55 (3H, s), 1.3 (6H, s).

EXAMPLE 17

(2E, 4E)-5-(2,3-Dihydrobenzoxepin-4-yl)-3-methylpenta-2,4-dienoic acid (I: p=0; R$_1$=H; X=O; A=—CH$_2$—CH$_2$—; R$_2$=Z; n=1; R'=CH$_3$; and compound 17a [sic]: Y=O—CH$_2$CH$_3$;

compound 17b [sic]: Y=—OH).

a) 2,3-Dihydro-4-(ethoxycarbonyl)-benzoxepine

A mixture of 8.2 g (0.043 mol) of 2,3-dihydro-4-carboxybenzoxepine in 150 ml of ethanol and 5 ml of concentrated sulphuric acid is brought to reflux for 6 hours. The reaction mixture is subsequently concentrated under reduced pressure and the residue is taken up in water. The combined mixture is extracted with ethyl acetate. The organic phase is then washed with sodium bicarbonate and then with water and dried over anhydrous sodium sulphate before being concentrated under reduced pressure. 8.5 g of an orange oil are thus obtained.

$^1$H NMR (CDCl$_3$, 300 MHz) δ (ppm): 7.6 (1H, s), 7.35–7 (4H, m), 4.2 (4H, m), 3 (2H, m), 1.3 (3H, m).

IR (cm$^{-1}$): 1705.

b) 2,3-Dihydro-4-(hydroxymethyl-benzoxepine.

A solution of 1.4 g (0.036 mol) of lithium aluminium hydride in 80 ml of diethyl ether is prepared and is maintained under an inert atmosphere. This solution is cooled in an ice and salt bath to 0° C. and then 8 g (0.036 mol) of the compound prepared in the preceding Stage a), dissolved in 80 ml of diethyl ether, are added to this solution. The reaction mixture is left at 0° C. for 1 hour and then water is added thereto while maintaining the temperature of the reaction mixture between 0 and 10° C. Extraction is subsequently carried out with diethyl ether and the aqueous mother liquours are saturated with sodium chloride. The organic phases are subsequently dried over anhydrous sodium sulphate and concentrated under reduced pressure to result in 7 g of a colourless oil. The presence of an OH alcohol peak is confirmed by infrared spectroscopy.

$^1$H NMR (CDCl$_3$, 300 MHz) δ (ppm): 7.15 to 6.9 (4H, m), 6.3 (1H, s), 4.2 (4H, m), 2.6 (2H, m), 1.8 (1H, s).

c) 2,3-Dihydro-4-formylbenzoxepine.

A mixture of 6.3 g (0.036 mol) of the compound prepared in the preceding Stage b), 250 ml of chloroform and 50 g (0.575 mol) of manganese dioxide is kept stirring for 16 hours at room temperature (25° C.).

After filtering through silica, the reaction mixture is concentrated under reduced pressure and 5 g of a yellow oil are obtained.

$^1$H NMR (CDCl$_3$, 300 MHz) δ (ppm): 9.5 (1H, s), 7.3 to 7 (5H, m), 4.2 (2H, m), 2.8 (2H, m).

d) Ethyl ester of (2E, 4E)-5-(2,3-dihydrobenzoxepin-4-yl)-3-methylpenta-2,4-dienoic acid (compound 17a).

0.72 g (0.03 mol) of sodium hydride and 20 ml of tetrahydrofuran are charged to a 250 mol four-necked flask maintained under an inert atmosphere. A solution of 7.5 ml (0.03 mol) of the ethyl ester of diethyl (2-methyl-3-carboxyprop-2-enyl)phosphonate acid [sic] in 20 ml of tetrahydrofuran is added to this solution. The combined mixture is left stirring for 1 hour at room temperature (25° C.) and then 5 g (0.0287 mol) of the compound prepared in the preceding Stage c), in 40 ml of tetrahydrofuran, are added to the reaction mixture. The combined mixture is again left stirring for 16 hours at 25° C. The reaction mixture is subsequently hydrolysed with water and poured onto a saturated aqueous sodium chloride solution. Extraction is subsequently carried out with ethyl acetate and the organic phase is dried over anhydrous sodium sulphate. The organic phase is subsequently concentrated under reduced pressure. 9.3 g of an oil are thus obtained, which oil is purified by flash chromatography using a mixture of cyclohexane and ethyl acetate as eluant. 5.8 g of an oil are thus isolated, which oil crystallizes at room temperature. This product is recrystallized from diisopropyl ether and 2.7 g of the title compound are obtained, which compound has a melting point of 100° C.

IR (cm$^{-1}$): peak at 1700.

$^1$H NMR (CDCl$_3$, 300 MHz) [lacuna] 7.4 to 7 (4H, m), 6.9 (1H, d, J=15.82 Hz), 6.65 (1H, s), 6.3 (1H, d, J=15.8 Hz), 5.95 (1H, s), 4.4 (2H, m), 4.3 (2H, m), 2.95 (2H, m), 2.5 (3H, s), 1.4 (3H, m).

e) (2E, 4E)-5-(2,3-Dihydrobenzoxepin-4-yl)-3-methylpenta-2,4-dienoic acid (compound 17b).

A solution of 0.4 g (0.01 mol) of sodium hydroxide in 40 ml of water is added to a solution of 2.7 g of the compound prepared in the preceding Stage d) in 40 ml of methanol. This solution is brought to reflux for 3 hours. 50 ml of methanol are again added to this mixture and reflux is continued for 3 hours. The reaction mixture is subsequently concentrated under reduced pressure and then the residue is taken up in water. The resulting solution is then acidified to pH 1 using 1N hydrochloric acid. The precipitate formed is filtered off, washed with water and then dried. 2.3 g of the title compound are obtained, which compound is recrystallized from methanol. 1.1 of purified product are isolated with a melting point of 220–222° C.

IR (cm$^{-1}$): 1669, 1588, 1262, 2400–3200.

$^1$H NMR (CDCl$_3$, 300 MHz) δ (ppm): 7.3–6.9 (5H, m), 6.7 (1H, s), 6.5–6.4 (1H, d, J=15.87 Hz), 5.8 (1H, s), 4.2 (2H, m), 2.8 (2H, m), 2.3 (3H, s).

EXAMPLES 18 TO 30

Examples 18 to 30 in the following Table 2 are prepared by using one of the methods illustrated in the preceding examples.

TABLE 2

| Example | Chemical formula | Characterization physico-chemical data |
|---|---|---|
| 18 | 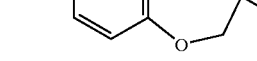 | M.p. 182–184° C.<br>¹H NMR (CDCl₃, 300 MHz) of the corresponding ethyl ester<br>δ (ppm): 7.4–7.1 (5H, m), 6.85–6.8 (1H, d, J = 8.73), 6.7 to 6.45 (3H, m), 6.2 to 6.15 (1H, d, J = 15.35 Hz), 5.95 (1H, s), 5.9 (1H, s), 3.95 (2H, q), 3.75 (2H, s), 3.65 (3H, s), 1.1 (6H, s), 1 (3H, t) |
| 19 | 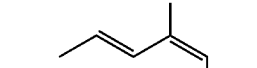 | ¹H NMR (CDCl₃, 300 MHz)<br>δ (ppm): 8 (1H, d, J = 15.69 Hz), 7.3 (5H, s), 6.85–6.8 (1H, d, J = 8.48 Hz), 6.6 (2H, m), 6.4–6.35 (1H, d, J = 15.65 Hz), 6.1 (1H, s), 5.7 (1H, s), 4.15 (2H, q), 3.8 (2H, s), 3.65 (3H, s), 1.25 (3H, t), 1.1 (6H, s) |
| 20a |  | ¹H NMR (CDCl₃, 300 MHz) δ (ppm):<br>7.92 (1H, d, J = 15.79), 6.7–6.95 (4H, m), 6.08 (1H, s), 5.7 (1H, s), 4.16 (2H, q), 3.84 (2H, s), 3.75 (3H, s), 2.07 (3H, s), 1.28 (3H, t), 1.15 (6H, s) |
| 20b | 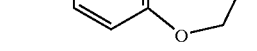 | IR (cm⁻¹) = 2975, 1683, 1493, 1244<br>¹H NMR (CDCl₃, 300 MHz) δ (ppm):<br>7.8–7.9 (1H, d, J = 15.66 Hz), 6.9 (1H, d), 6.8–6.6 (3H, m), 6 (1H, s), 5.65 (1H, s), 3.8 (2H, s), 3.7 (3H, s), 2.05 (3H, s), 1.1 (6H, s). |
| 21a |  | ¹H NMR (CDCl₃, 300 MHz) δ (ppm):<br>6.73–6.62 (2H, m), 6.52 (1H, s), 6.40–6.37 (1H, d, J = 15.4 Hz), 5.80 (1H, s), 5.77 (1H, s), 4.15–4.07 (2H, m), 3.82 (2H, s), 3.75 (3H, s), 3.74 (3H, s), 2.3 (3H, s), 1.25–1.19 (3H, m), 1.08 (6H, s) |

TABLE 2-continued
| | | |
|---|---|---|
| 21b | 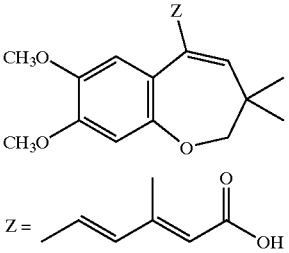 | M.p. = 181–183° C. |
| 22a | 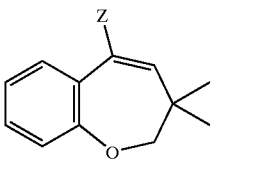 | ¹H NMR (CDCl₃, 300 MHz) δ (ppm):<br>7.18–6.94 (4H, m), 6.84 (1H, d, J = 15.4 Hz),<br>6.36 (1H, d, J = 15.4 Hz), 5.90 (1H, s), 5.77 (1H, s),<br>4.15–4.07 (2H, m), 3.83 (2H, s), 2.30 (3H, s),<br>1.24–1.16 (3H, m), 1.09 (6H, s) |
| 22b | 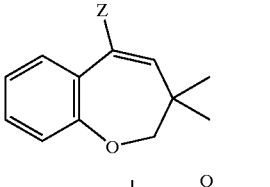 | M.p. = 178–180° C. |
| 23a | 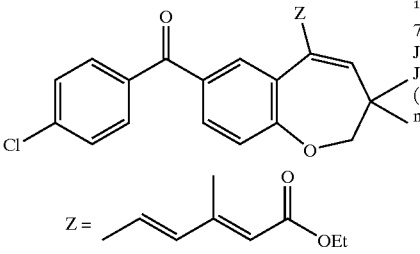 | ¹H NMR (CDCl₃, 300 MHz) δ (ppm):<br>7.70–7.54 (4H, m), 7.39–7.34 (2H, m), 7.02 (1H, d,<br>J = 7.9 Hz), 6.67 (1H, d, J = 15.4 Hz), 6.36 (1H, d,<br>J = 15.4 Hz), 6.09 (1H, s), 5.76 (1H, s), 4.15–4.03<br>(2H, m), 3.29 (2H, s), 1.96 (3H, s), 1.24–1.20 (3H,<br>m), 1.16 (6H, s) |
| 23b | 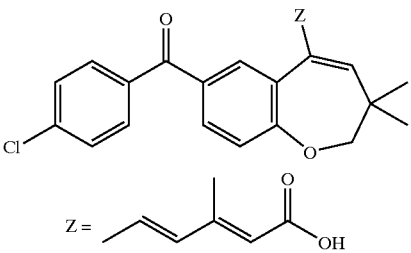 | M.p. = 206–208° C. |
| 24a | 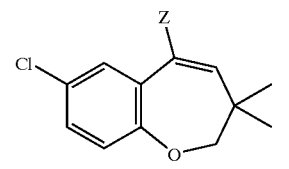 | ¹H NMR (CDCl₃, 300 MHz) δ (ppm):<br>7.18–7.03 (2H, m), 6.89 (1H, d, J = 8.5 Hz), 6.64<br>(1H, d, J = 15.4 Hz), 6.35 (1H, d, J = 15.4 Hz), 5.93<br>(1H, s), 5.78 (1H, s), 4.16–4.08 (2H, m), 3.80 (2H,<br>s), 2.31 (3H, s), 1.25–1.18 (3H, m), 1.08 (6H, s) |

TABLE 2-continued
| | | |
|---|---|---|
| 24b | 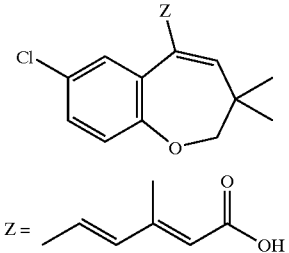 | M.p. = 177–179° C. |
| 25 | 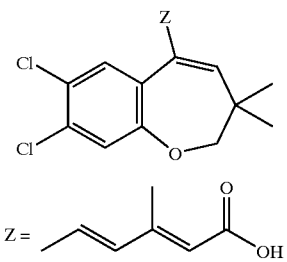 | M.p. = 180° C.<br>¹H NMR (CDCl₃, 300 MHz) of the corresponding ethyl ester δ (ppm): 7.25 (1H, s), 7 (1H, s), 6.6 (1H, d), 6.3 (1H, d), 5.9 (1H, s), 5.8 (1H, s), 4.15 (2H, m), 3.8 (2H, s), 2.3 (3H, s), 1.2 (3H, t), 1.1 (6H, s). |
| 26a | 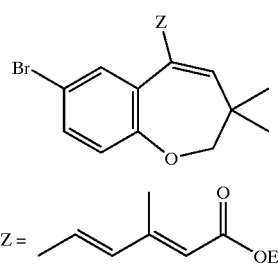 | ¹H NMR (CDCl₃, 300 MHz) δ (ppm): 7.29–6.81 (3H, m), 6.7 (1H, d, J = 15.4 Hz), 6.35 (1H, d, J = 15.4 Hz), 5.92 (1H, s), 5.79 (1H, s), 4.10 (2H, m), 3.8 (2H, s), 2.31 (3H, s), 1.21 (3H, m), 1.16 (6H, s) |
| 26b | 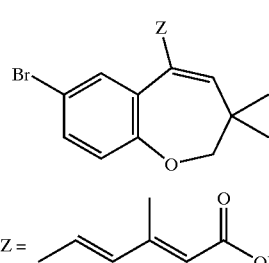 | M.p. = 164–165° C. |
| 27 | 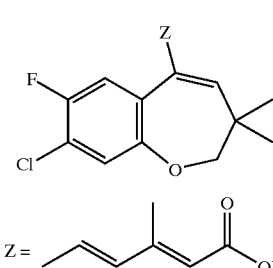 | M.p. = 200° C.<br>¹H NMR (CDCl₃, 300 MHz) δ (ppm) of the corresponding ethyl ester [sic]: 7 (2H, m), 6.6 (1H, d, J = 15.45 Hz), 6.3 (1H, d, J = 15.42 Hz), 6 (1H, s), 5.8 (1H, s), 4.1 (2H, m), 3.8 (2H, s), 2.3 (3H, s), 1.1 (6H, s) |
| 28a | 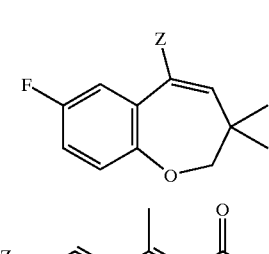 | ¹H NMR (CDCl₃, 300 MHz) δ (ppm): 7.19–6.78 (3H, m), 6.64 (1H, d, J = 15.4 Hz), 6.34 (1H, d, J = 15.4 Hz), 5.93 (1H, s), 5.78 (1H, s), 4.15–4.03 (2H, m), 3.80 (2H, s), 2.30 (3H, s), 1.25–1.20 (3H, m), 1.09 (6H, s) |

TABLE 2-continued
| | | |
|---|---|---|
| 28b | 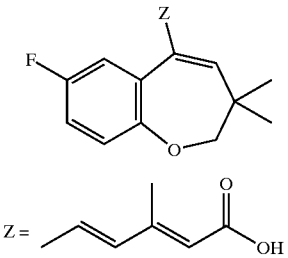 | M.p. = 193–195° C. |
| 29a | 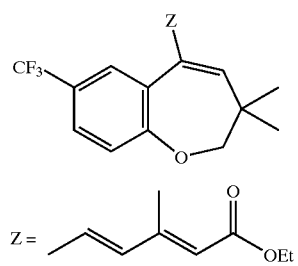 | ¹H NMR (CDCl₃, 300 MHz) δ (ppm): 7.45–7.34 (2H, m), 7.02 (1H, d, J = 8.1 Hz), 6.66 (1H, d, J = 15.4 Hz), 6.37 (1H, d, J = 15.4 Hz), 5.98 (1H, s), 5.78 (1H, s), 4.16–4.09 (2H, m), 3.85 (2H, s), 2.30 (3H, s), 1.25–1.16 (3H, m), 1.11 (6H, s) |
| 29b | 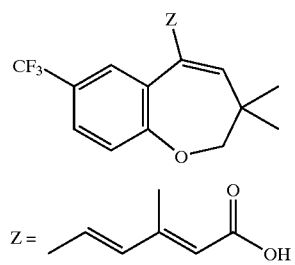 | M.p. = 163–165° C. |
| 30a | 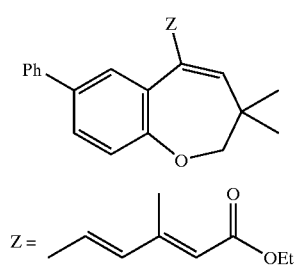 | ¹H NMR (CDCl₃, 300 MHz) δ (ppm): 7–7.6 (8H, m), 6.9 (1H, d, J = 15.47 Hz), 6.5 (1H, d, J = 15.43 Hz), 6 (1H, s), 5.9 (1H, s), 4 (2H, m), 3.8 (2H, s), 2.24 (3H, s), 1.1 (3H, t), 1.01 (6H, s) |
| 30b | 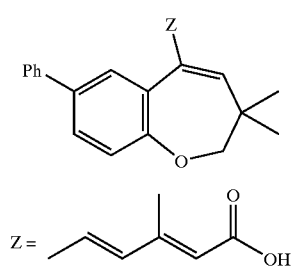 | M.p. = 206–208° C. |
| 31 | 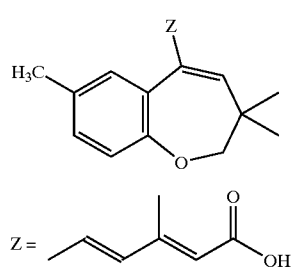 | ¹H NMR (CDCl₃, 300 MHz) δ (ppm): 12.2 (1H, s, exchangeable with CF₃COOD), 7.17–7.06 (2H, m), 6.86–6.97 (2H, m), 6.57 (1H, d, J = 15.4 Hz), 6.10 (1H, s), 5.94 (1H, s), 3.89 (2H, s), 2.37 (3H, s), 2.32 (3H, s), 1.17 (6H, s) |

TABLE 2-continued

| Ex | Chemical formula | Nomenclature | Characterization physicochemical data |
|---|---|---|---|
| 32a | (structure with OMe, Z substituent; Z = ethyl ester dienoate) | | M.p. = 94° C.<br>$^1$H NMR (CDCl$_3$, 300 MHz) δ (ppm):<br>6.88–6.68 (4H, m), 6.35 (1H, d, J = 15.44 Hz), 5.92 (1H, s), 5.76 (1H, s), 4.10 (2H, m), 3.9 (2H, s), 3.83 (3H, s), 2.3 (3H, s), 1.22 (3H, m), 1.1 (6H, s) |
| 32b | (structure with OMe, Z substituent; Z = carboxylic acid dienoate) | | M.p. = 180–184° C.<br>$^1$H NMR (CDCl$_3$, 300 MHz) δ (ppm):<br>7.15–6.94 (4H, m), 6.59 (1H, d, J = 15.35 Hz), 6.15 (1H, s), 6.0 (1H, s), 4.11 (2H, s), 4.0 (3H, s), 2.51 (3H, s), 1.3 (6H, s) |
| 33 | (structure with H$_3$C, Z substituent; Z = ethyl ester dienoate) | | $^1$H NMR (CDCl$_3$, 300 MHz) δ (ppm):<br>7.1–6.8 (3H, m), 6.72 (1H, d, J = 16 Hz), 6.35 (1H, d, J = 15.4 Hz), 5.87 (1H, s), 5.77 (1H, s), 4.15–4.08 (2H, m), 3.80 (2H, s), 2.30 (3H, s), 2.20 (3H, s), 1.25–1.18 (3H, m), 1.08 (6H, s) |
| 34A | (spiro cyclohexane benzoxepine with ethyl ester dienoate) | (2E, 4E)-5-(Spiro[(7-methoxy-2,3-dihydrobenzo[b]-oxepine)-3,1'-cyclohexane]-5-yl)-3-methyl-penta-2,4-dienoic acid ethyl ester [sic] | NMR 300 MHz (CDCl$_3$) ppm:<br>1.19 (3H, t), 1.35–1.60 (10H, m), 2.3 (3H, s), 3.70 (3H, s), 3.92 (2H, s), 4.1 (2H, q), 5.75 (1H, s), 6.06 (1H, s), 6.36 (1H, D, J = 15 Hz), 6.74 (1H, d, J = 15 Hz), 6.64–6.89 (3H, Ar, m). |
| 34B | (spiro cyclohexane benzoxepine with carboxylic acid dienoate) | (2E, 4E)-5-(Spiro[(7-methoxy-2,3-dihydrobenzo[b]-oxepine)-3,1'-cyclohexane]-5-yl)-3-methyl-penta-2,4-dienoic acid. [sic] | M.p. = 173–174° C.<br>NMR 300 MHz (CDCl$_3$) ppm:<br>1.50–1.70 (10H, m), 2.50 (3H, s), 3.88 (3H, s), 4.12 (2H, s), 5.97 (1H, s), 6.27 (1H, s), 6.58 (1H, d, J = 15 Hz), 6.85 (1H Ar, dd, J = 3 Hz, J = 8 Hz), 6.90 (1H Ar, d, J = 3 Hz), 6.98 (1H, d, J = 15 Hz), 7.07 (1H Ar, d, J = 8 Hz). |

TABLE 2-continued

| | | | |
|---|---|---|---|
| 35A | 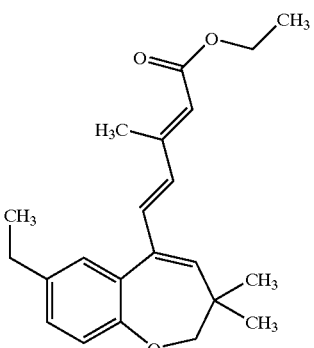 | (2E, 4E)-5-(7-Ethyl-3,3-dimethyl-2,3-dihydrobenzo[b]-oxepine-5-yl)-3-methylpenta-2,4-dienoic acid ethyl ester [sic] | NMR 300 MHz (CDCl$_3$): 3H 7–6.85 ppm (m); 1H 6.7–6.75 ppm (d) J = 15.4 Hz; 1H 6.35–6.40 ppm (d) J = 15.4 Hz; 1H 5.9 ppm (s); 1H 5.75 ppm (s); 2H 4.1 ppm (q); 2H 3.8 ppm (s); 2H 2.5 ppm (q); 3H 2.3 ppm (s); 3H 1.25 ppm (t); 3H 1.2 ppm (t); 6H 1.1 ppm (s). |
| 35B | 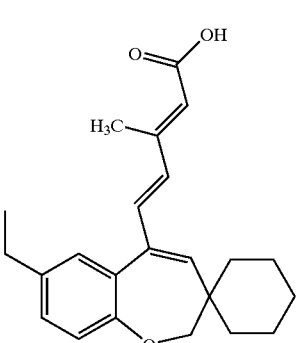 | (2E, 4E)-5-(7-Ethyl-3,3-dimethyl-2,3-dihydrobenzo[b]-oxepin-5-yl)-3-methylpenta-2,4-dienoic acid [sic] | M.p. = 142–144° C. NMR 300 MHz (CDCl$_3$): 1H 7.45 ppm (s); 4H 7.25–7.05 ppm (m); 1H 6.6–6.7 ppm (d) J = 15.38 Hz; 1H 6.15 ppm (s); 1H 6.05 ppm (s); 2H 4.05 ppm (s); 2H 2.8 ppm (q); 3H 2.6 ppm (s); 3H 1.4 ppm (t); 6H 1.3 ppm (s). |
| 36A | 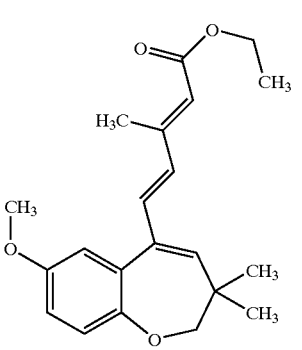 | (2E, 4E)-5-(7-(4-Methoxyphenyl)-3,3-dimethyl-2,3-dihydrobenzo[b]-oxepin-5-yl]-3-methylpenta-2,4-dienoic acid ethyl ester [sic] | NMR 300 MHz (CDCl$_3$): 4H 7.39–7.27 ppm (m); 1H 6.99 ppm (d) J = 8.2 Hz; 2H 6.89–6.86 ppm (m); 1H 6.77 ppm (d) J = 15.5 Hz; 1H 6.40 ppm (d) J = 15.5 1H 6.40 ppm (d) J = 15.5 Hz; 1H 5.93 ppm (s); 1H 5.78 ppm (s); 2H 4.10 ppm (q) J = 6.5 Hz; 2H 3.85 ppm (s); 3H 3.76 ppm (s); 3H 2.19 ppm (s); 3H 1.21 ppm (t) J = 6.5 Hz; 6H 1.1 ppm (s). |
| 36B | 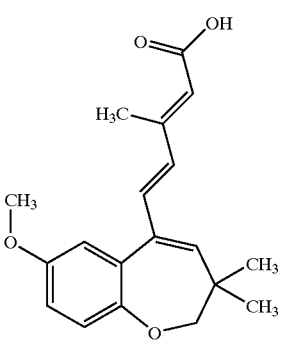 | (2E, 4E)-5-[7-(4-Methoxyphenyl)-3,3-dimethyl-2,3-dihydrobenzo[b]-oxepin-5-yl]-3-methylpenta-2,4-dienoic acid [sic] | M.p. = 217–219° C. NMR 300 MHz (DMSO [sic]): 1H 12.2 ppm (s); 4H 7.64–7.52 ppm (m): 4H 7.19–7.01 ppm (m); 1H 6.66 ppm (d) J = 15.4 Hz; 1H 6.20 ppm (s); 1H 5.99 ppm (s); 2H 4.00 ppm (s); 3H 3.89 ppm (s); 3H 2.41 ppm (s); 6H 1.25 ppm (s). |

TABLE 2-continued

| | | | |
|---|---|---|---|
| 37A | 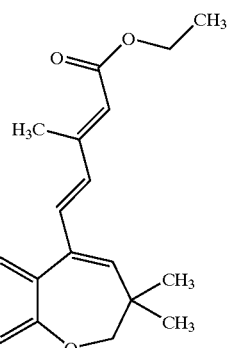 | (2E, 4E)-3-Methyl-5-(3,3,7,8-tetramethyl-2,3-dihydrobenzo[b]-oxepin-5-yl)penta-2,4-dienoic acid ethyl ester [sic] | NMR 300 MHz (CDCl$_3$): 1H 6.91 ppm (s); 2H 6.76–6.69 ppm (m); 1H 6.35 ppm (d) J = 15.4 Hz; 1H 5.82 ppm (s); 1H 5.77 ppm (s); 2H 4.12 ppm (q) J = 7 Hz; 2H 3.79 ppm (s); 3H 2.31 ppm (d) J = 0.8 Hz; 3H 2.15 ppm (s); 3H 2.12 ppm (s); 3H 1.22 ppm (s); 6H 1.07 ppm (s). |
| 37B | 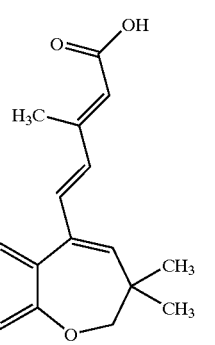 | 3-Methyl-5-(3,3,7,8-tetramethyl-2,3-dihydrobenzo[b]-oxepin-5-yl)penta-2,4-dienoic acid [sic] | M.p. 171–173° C. NMR 300 MHz (DMSO [sic]): 1H 6.99 ppm (s); 2H 6.81–6.76 ppm (m); 1H 6.45 ppm (d) J = 15.4 Hz; 1H 5.93 ppm (s); 1H 5.83 ppm (s); 2H 3.76 ppm (s); 3H 2.27 ppm (d) J = 0.4 Hz; 6H 2.13 ppm (s); 6H 1.06 ppm (s). |
| 38A | 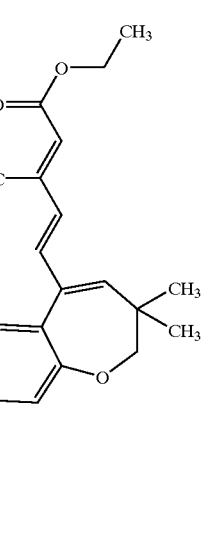 | (2E, 4E)-5-[8-(4-Fluorophenyl)-3,3-dimethyl-2,3-dihydrobenzo[b]-oxepin-5-yl]-3-methylpenta-2,4-dienoic acid ethyl ester [sic] | M.p. = 113–115° C. NMR 300 MHz (CDCl$_3$): 2H 7.66–7.61 ppm (m); 1H 7.4 ppm (d) J = 8.7 Hz; 2H 7.34–7.30 ppm (m); 2H 7.23 ppm (t) J = 8.7 Hz; 1H 6.91 ppm (d) J = 15.4 Hz; 1H 6.54 ppm (d) J = 15.4 Hz; 1H 5.94 ppm (s); 2H 4.27 ppm (q) J = 7.1 Hz; 2H 4.02 ppm (s); 3H 2.4 ppm (d) J = 0.8 Hz; 3H 1.38 ppm (t) J = 7.1 Hz; 6H 1.27 ppm (s). |

TABLE 2-continued

| | | | |
|---|---|---|---|
| 38B | 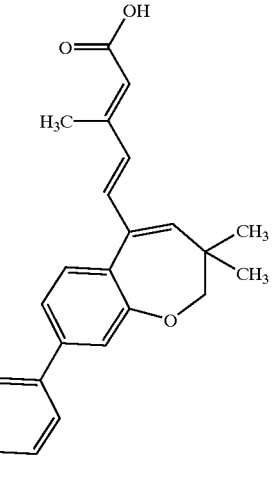 | (2E, 4E)-5-[8-(4-Fluorophenyl)-3,3-dimethyl-2,3-dihydrobenzo[b]-oxepin-5-yl]-3-methylpenta-2,4-dienoic acid [sic] | M.p. = 207–209° C. NMR 300 MHz (DMSO [sic]): 1H 12.24 ppm (s); 2H 7.88–7.83 ppm (m); 5H 7.53–7.36 ppm (m); 1H 6.99 ppm (d) J = 15.4 Hz; 1H 6.66 ppm (d) J = 15.4 Hz; 1H 6.20 ppm (s); 1H 6.00 ppm (s); 2H 4.03 ppm (s); 3H 2.43 ppm (d) J = 0.5 Hz; 6H 1.26 ppm (s). |
| 39A | 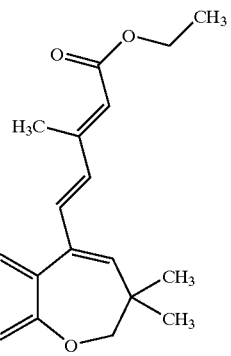 | (2E, 4E)-5-(8-Methoxy-3,3-dimethyl-2,3-dihydrobenzo[b]-oxepin-5yl)-3-methylpenta-2,4-dienoic acid ethyl ester [sic] | NMR 300 MHz (CDCl$_3$): 1.05 ppm (6H, s) - 1.18–1.24 ppm (3H, s) - 2.27 ppm (3H, s) - 3.7 ppm (3H, s) - 3.8 ppm (2H, s), - 4.05–4.14 ppm (2H, m) - 5.87 ppm (1H, s) - 6.3 ppm (1H, s) - 6.37 ppm (1H, s); 6.5–6.55 ppm (2H, Ar, m) - 6.7–6.37 (1H, d, J = 15.5 Hz) - 7.08–7.12 ppm (1H, d, J = 11 Hz). |
| 39B | 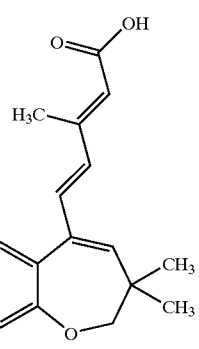 | (2E, 4E)-5-(8-Methoxy-3,3-dimethyl-2,3-dihydrobenzo[b]-oxepin-5-yl)-3-methylpenta-2,4-dienoic acid [sic] | M.p. = 178–180° C. NMR 300 MHz (CDCl$_3$): 1.2 ppm (6H, s), - 2.6 ppm (3H, s) - 3.83 ppm (3H, s) - 3.96 ppm (2H, s) - 5.92 ppm (2H, s) - 6.49–6.54 ppm (1H, d, J = 15.4 Hz) - 6.65–6.68 ppm (2H, Ar, t) - 6.87–6.92 ppm (1H, d, J = 15.4) - 7.2–7.24 ppm (1H, d, J = 8.2 Hz). |
| 40A | 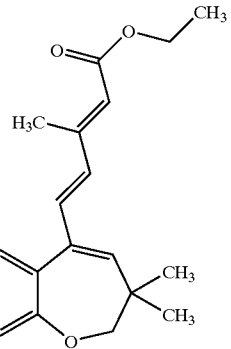 | (2E, 4E)-5-(7-Isopropyl-3,3-dimethyl-2,3-dihydrobenzo[b]-oxepin-5-yl)-3-methylpenta-2,4-dienoic acid ethyl ester. [sic] | NMR 300 MHz (CDCl$_3$): 4H 7.05–6.7 ppm (m); 1H 6.8 ppm (d); 1H 5.9 ppm (s); 1H 5.75 ppm (s); 2H 4.1 ppm (q); 2H 3.8 ppm (s); 1H 2.8 ppm (m); 3H 2.3 ppm (s); 15H 1.3–105 [sic] ppm (m). |

TABLE 2-continued

| | | | |
|---|---|---|---|
| 40B | 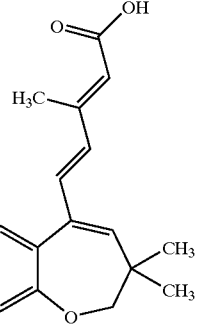 | (2E, 4E)-5-(7-Isopropyl-3,3-dimethyl-2,3-dihydrobenzo[b]-oxepin-5-yl)-3-methylpenta-2,4-dienoic acid. [sic] | M.p. = 145° C. NMR 300 MHz (CDCl3 [sic]): 4H 7.25–7 ppm (m); 1H 6.7 ppm (d); 1H 6.2 ppm (s); 1H 6.05 ppm (s); 2H 4.1 ppm (s); 1H 3 ppm (m); 3H 2.6 ppm (s); 6H 1.4 ppm (d); 6H 1.3 ppm (s). |
| 41 | 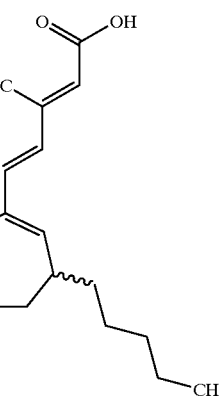 | (2E, 4E)-5-(7-Methoxy-3-pentyl-2,3-dihydrobenzo[b]-oxepin-5-yl)-3-methylpenta-2,4-dienoic acid. [sic] | M.p. = 154–156° C. NMR 300 MHz (CDCl$_3$) ppm: 0.80 (3H, t), 1.17–1.35 (8H, m), 2.29 (3H, s), 2.36–2.40 (1H, m), 3.72 (3H, s), 4.00 (1H CH2 [sic], m), 4.24 (1H CH2 [sic], m), 5.69 (1H, s), 6.12 (1H, Ar, d, J = 6 Hz), 6.33 (1H, d, J = 16 Hz), 6.75 (3H, m), 6.99 (1H Ar, d, J = 10 Hz). |
| 42A | 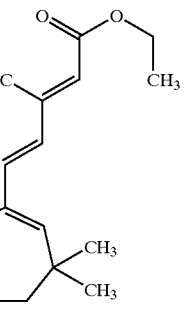 | (2E, 4E)-5-(3,3-Dimethyl-7-trifluoromethoxy-2,3-dihydrobenzo[b]-oxepin-5-yl)-3-methylpenta-2,4-dienoic acid ethyl ester [sic] | NMR 300 MHz (CDCl$_3$): 1.17 ppm (6H, s) - 1.23–1.27 ppm (3H, m) - 2.36 ppm (3H, s) - 3.9 ppm (2H, s), - 4.13–4.22 ppm (2H, m) 6 ppm (1H, s) - 6.14 ppm (1H, s) - 6.39–6.44 ppm (1H, d, J = 15.4 Hz) - 6.67–6.72 ppm (1H, d, J = 15.4 Hz) - 6.98–7.10 ppm (3H, m). |
| 42B | 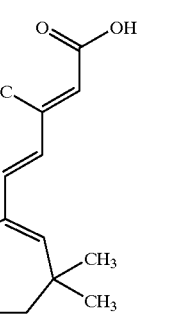 | (2E, 4E)-5-(3,3-Dimethyl-7-trifluoromethoxy-2,3-dihydrobenzo[b]-oxepin-5-yl)-3-methylpenta-2,4-dienoic acid [sic] | M.p. = 148–150° C. NMR 300 MHz (CDCl$_3$): 1.22 ppm (6H, s) - 2.43 ppm (3H, s) - 3.95 ppm (2H, s) - 5.9 ppm (1H, s), - 6.1 ppm (1H, s) - 6.49–6.54 ppm (1H, d, J = 15.4 Hz) - 6.78–6.84 ppm (1H, d, J = 15.4 Hz) - 7.05–7.15 ppm (3H, m). |

TABLE 2-continued

| | | | |
|---|---|---|---|
| 43A | (structure) | (2E, 4E)-3-Ethyl-5-(7-methoxy-3,3-dimethyl-2,3-dihydrobenzo[b]-oxepin-5-yl)penta-2,4-dienoic acid ethyl ester [sic] | NMR 300 MHz (CDCl$_3$): 1H 7.79 ppm (d) J = 15.8 Hz; 4H 6.91–6.64 ppm (m); 1H 6.03 ppm (s); 1H 5.64 ppm (s); 2H 4.12 ppm (q) J = 7 Hz; 2h [sic] 3.80 ppm (s); 3H 3.69 ppm (s); 2H 2.39 ppm (s); 12H 1.25–1.07 ppm (m). |
| 43B | (structure) | (2E, 4E)-3-Ethyl-5-(7-methoxy-3,3-dimethyl-2,3-dihydrobenzo[b]-oxepin-5-yl)penta-2,4-dienoic acid [sic] | M.p. = 166–168° C. NMR 300 MHz (CDCl$_3$): 1H 11.4 ppm (s); 1H 7.03 ppm (d) J = 8.5 Hz; 1H 6.93 ppm (d) J = 15.5 Hz; 2H 6.86–6.80 ppm (m); 1H 6.40 ppm (d) J = 15.5 Hz; 1H 6.09 ppm (s); 1H 5.90 ppm (s); 2H 3.95 ppm (s); 3H 3.84 ppm (s); 2H 2.99 ppm (q) J = 7.5 Hz; 9H 1.33–1.24 ppm (m). |
| 44A | (structure) | (2E, 4E)-5-(7-Hydroxy-3,3-dimethyl-2,3-dihydrobenzo[b]-oxepin-5-yl)-3-methylpenta-2,4-dienoic acid ethyl ester [sic] | NMR 300 MHz (CDCl$_3$): 4H 6.9–6.58 ppm (m); 1H 6.37 ppm (d) J = 15.42 Hz; 1H 5.9 ppm (s); 1H 5.75 ppm (s); 2H 4.15 ppm (m); 2H 3.8 ppm (s); 3H 2.3 ppm (s); 3H 1.25 ppm (m); 6H 1.18 ppm (s). |
| 44B | (structure) | (2E, 4E)-5-(7-Hydroxy-3,3-dimethyl-2,3-dihydrobenzo[b]-oxepin-3-yl)-3-methylpenta-2,4-dienoic acid. [sic] | M.p. = 206° C. NMR 300 MHz (DMSO[sic]): 1H 9.1 ppm; 5H 6.9–6.5 ppm (m); 1H 6.0 ppm (s); 1H 5.85 ppm (s); 2H 3.8 ppm (s); 3H 2.5 ppm (s); 6H 1.08 ppm (s). |

TABLE 2-continued

| | | | |
|---|---|---|---|
| 45A | (structure) | (2E, 4E)-5-[3,3-Dimethyl-7-(4-(trifluoromethyl)phenyl)-2,3-dihydrobenzo[b]-oxepin-5-yl]-3-methylpenta-2,4-dienoic acid ethyl ester [sic] | NMR 300 MHz (CDCl$_3$): 2H 7.62–7.52 ppm (m); 4H 7.43–7.33 ppm (m); 1H 7.05 (d) J = 8.2 Hz; 1H 6.75 (d) J = 15.4 Hz; 1H 6.40 (d) J = 15.4 Hz; 1H 5.97 ppm (s); 1H 5.79 ppm (s); 2H 4.12 ppm (q) J = 7.1 Hz; 2H 3.88 ppm (s); 3H 2.30 ppm (s); 3H 1.22 ppm (t) J = 7.1 Hz; 5H 1.12 ppm (s). |
| 45B | (structure) | (2E, 4E)-5-[3,3-Dimethyl-7-(4-(trifluoromethyl)phenyl)-2,3-dihydrobenzo[b]-oxepin-5-yl]-3-methylpenta-2,4-dienoic acid [sic] | M.p. = 194–196° C. NMR 300 MHz (CDCl$_3$): 1H 11.8 ppm (s); 4H 7.90–7.80 ppm (m); 2H 7.67–7.61 ppm (m); 1H 7.33 ppm (d) J = 8.2 Hz; 1H 7.09 ppm (d) J = 15.4 Hz; 1H 6.73 ppm (d) J = 15.4 Hz; 1H 6.27 ppm (s); 1H 6.10 ppm (s); 2H 4.16 ppm (s); 3H 2.60 ppm (s); 6H 1.41 ppm (s). |
| 46A | (structure) | (2E, 4E)-5-(5-Methoxy-2,2-dimethyl-2H-chromen-4-yl)-3-methylpenta-2,4-dienoic acid ethyl ester | NMR 300 MHz (CDCl$_3$): 1.18–1.25 ppm (3H, t) - 1.34 ppm (6H, s) - 2.29 ppm (3H, s) - 4.08–4.15 ppm (2H, m) - 5.66 ppm (1H, s) - 5.75 ppm (1H, s) - 6.33–6.48 ppm (3H, m) - 7–7.1 ppm (2H, m). |
| 46B | (structure) | (2E, 4E)-5-(5-Methoxy-2,2-dimethyl-2H-chromen-4-yl)-3-methylpenta-2,4-dienoic acid | M.p. = 160–162° C. NMR 300 MHz (CDCl$_3$): 1.36 ppm (6H, s) - 2.28 ppm (3H, s) - 3.77 ppm (3H, s) - 5.85 ppm (1H, s) - 5.92 ppm (1H, s) - 6.49–6.63 ppm (3H, m) - 708[sic]–7.17 ppm (2H, m) - 12.1 ppm (1H, s). |

TABLE 2-continued

| | | | |
|---|---|---|---|
| 47A | 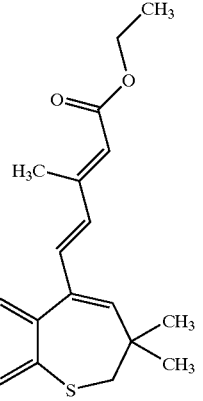 | (2E, 4E)-5-(7-Methoxy-3,3-dimethyl-2,3-dihydrobenzo[b]-thiepin-5-yl)-3-methylpenta-2,4-dienoic acid ethyl ester | NMR 300 MHz (CDCl$_3$) ppm: 1.06 (6H, s), 1.15 (3H, t), 1.96 (3H, s), 2.25 (2H, s), 3.70 (3H, s), 4.05(2H, q), 5.64 (1H, s), 6.07(1H, s), 6.17 (1H, d, J = 16 Hz), 6.63 (1H, d, J = 16 Hz), 6.65 (1H Ar, dd, J = 3 Hz, J = 8 Hz), 6.85 (1H, Ar, d, J = 3 Hz), 7.42 (1H Ar, d, J = 8 Hz). |
| 47B | 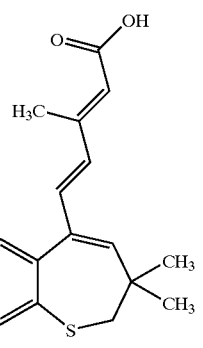 | (2E, 4E)-5-(7-Methoxy-3,3-dimethyl-2,3-dihydrobenzo[b]-thiepin-5-yl)-3-methylpenta-2,4-dienoic acid | M.p. = 159–161° C. NMR 300 MHz (CDCl$_3$) ppm: 1.29 (6H, s), 2.50 (3H, s), 2.97 (2H, s), 3.95 (3H, s), 5.90 (1H, s), 6.33 ((([sic]1H, s) 6.43 (1H, d, J = 16 Hz), 6.89 (1H Ar, dd, J = 3Hz, J = 8 Hz), 6.91 (1H, d, J = 16 Hz), 7.01 (1H Ar, d, J = 3 Hz), 7.61 (1H Ar, d, J = 8Hz). |
| 48A | 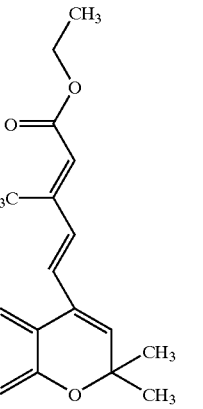 | (2E, 4E)-5-(7-Methoxy-2,2-dimethyl-2H-chromen-4-yl)-3-methylpenta-2,4-dienoic acid ethyl ester | NMR 300 MHz (CDCl$_3$) ppm: 1.18–1.25 ppm (3H, m) - 1.37 ppm (6H, s) - 2.3 ppm (3H, s) - 3.7 ppm (3H, s) - 4.08–4.15 ppm (2H, m) - 5.6 ppm (1H, s) - 5.78 ppm (1H, s) - 6.37–6.74 ppm (4H, m) - 7.1–7.13 ppm (1H, d, J = 8.4 Hz). |
| 48B | 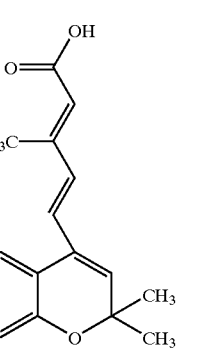 | (2E, 4E)-5-(7-Methoxy-2,2-dimethyl-2H-chromen-4-yl)-3-methylpenta-2,4-dienoic acid | M.p. = 162–163° C. NMR 300 MHz (CDCl$_3$): 1.37 ppm (6H, s) - 2.33 ppm (3H, s) - 3.72 ppm (3H, s) - 5.65 ppm (1H, s) - 5.83 ppm (1H, s) - 6.38–7.10 ppm (5H, m). |

TABLE 2-continued

| | | | |
|---|---|---|---|
| 49A | 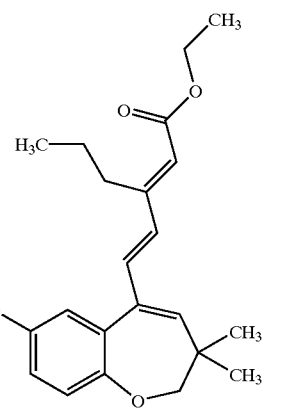 | (2E, 4E)-5-(7-Methoxy-3,3-dimethyl-2,3-dihydrobenzo[b]-oxepin-5-yl)-3-propylpenta-2,4-dienoic acid ethyl ester [sic] | NMR 300 MHz (CDCl$_3$): 1H 6.96 ppm (d) J = 8.6 Hz; 3H 6.82–6.73 ppm (m); 1H 6.37 ppm (d) J = 15.4 Hz; 1H 5.99 ppm (s); 1H 5.83 ppm (s); 2H 4.20 ppm (q) J = 7.1 Hz; 2H 3.88 ppm (s); 3H 3.78 ppm (s); 2H 2.86 ppm (t) J = 7.5 Hz; 2H 1.68–1.61 ppm (m); 3H 1.3 ppm (t) J = 7.1 Hz; 6H 1.18 ppm (s); 3H 1.06 ppm (t) J = 7.5 Hz. |
| 49B | 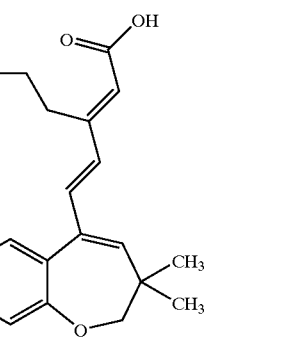 | (2E, 4E)-5-(7-Methoxy-3,3-dimethyl-2,3-dihydrobenzo[b]-oxepin-5-yl)-3-propylpenta-2,4-dienoic acid [sic] | M.p. = 174–176° C.<br>NMR 300 MHz (CDCl$_3$): 1H 11.2 ppm (s); 1H 6.86 ppm (d) J = 8.35 Hz; 1H 6.74 ppm (d) J = 15.5 Hz; 2H 6.67 ppm (m); 1H 6.29 ppm (d) J = 15.5 Hz; 1H 5.91 ppm (s): 1H 5.75 ppm (s); 2H 3.77 ppm (s); 3H 3.67 ppm (s); 2H 2.78 ppm (t) J = 7.5 Hz; 2H 1.50 (q) J = 7.5 Hz; 6H 1.06 ppm (s); 3H 0.92 ppm (t) J = 7.4 Hz. |
| 50A | 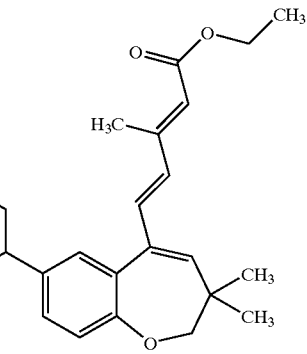 | (2E, 4E)-5-(7-Cyclohexyl-3,3-dimethyl-2,3-dihydrobenzo[b]-oxepin-5-yl)-3-methylpenta-2,4-dienoic acid ethyl ester [sic] | NMR 300 MHz (CDCl$_3$): 3H 7.10–6.84 ppm (m); 1H 6.47 ppm (d) J = 15.4 Hz; 1H 6.36 ppm (d) J = 15.4 Hz; 1H 5.87 ppm (s); 1H 5.78 ppm (s); 2H 4.15–4.07 ppm (m); 2H 3.81 ppm (s); 4H 2.37–2.32 ppm (m); 5H 1.78–1.68 ppm (m); 8H 1.35–1.18 ppm (m); 6H 1.08 ppm (s). |
| 50B | 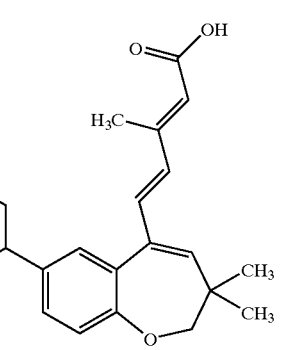 | (2E, 4E)-5-(7-Cyclohexyl-3,3-dimethyl-2,3-dihydrobenzo[b]-oxepin-5-yl)-3-methylpenta-2,4-dienoic acid [sic] | M.p. 195–196° C.<br>NMR 300 MHz (CDCl$_3$): 2H 7.18–7.14 ppm (m); 1H 7.07 ppm (d) J = 8.0 Hz; 1H 6.99 ppm (d) J = 15.4 Hz; 1H 6.60 ppm (d) J = 15.4 Hz; 1H 6.10 ppm (s); 1H 6.01 ppm (s); 2H 4.01 ppm (s); 4H 2.56–2.53 ppm (m); 5H 1.98–1.84 ppm (m); 11H 1.50–1.28 ppm (m). |

TABLE 2-continued

| | | | |
|---|---|---|---|
| 51A | | (2Z, 4E)-3-Ethyl-5-(7-methoxy-3,3-dimethyl-2,3-dihydrobenzo[b]-oxepin-5-yl)penta-2,4-dienoic acid ethyl ester [sic] | NMR 300 MHz (CDCl$_3$): 1H 7.79 ppm (d) J = 15.8 Hz; 4H 6.91–6.94 ppm (m); 1H 6.03 ppm (s); 1H 5.64 ppm (s); 2H 4.12 ppm (q) J = 7 Hz; 2h [sic] 3.80 ppm (s); 3H 3.69 ppm (s); 2H 2.39 ppm (s); 12H 1.25–1.07 ppm (m) |
| 51B | | (2Z, 4E)-3-Ethyl-5-(7-methoxy-3,3-dimethyl-2,3-dihydrobenzo[b]-oxepin-5-yl)-penta2,4-dienoic acid [sic] | NMR 300 MHz (CDCl$_3$): 1H 7.76 ppm (d) J = 15.8 Hz; 4H 6.89–6.64 ppm (m); 1H 6.01 ppm (s); 1H 5.68 ppm (s); 2H 3.80 ppm (s); 3H 3.69 ppm (s); 2H 2.43 ppm (t) J = 7.4 Hz; 9H 1.15 ppm (m). |
| 52A | | (2E, 4E)-5-(7-Methoxy-3,3-dimethyl-2,3-dihydrobenzo[b]-oxepin-5-yl)-3-pentylpenta-2,4-dienoic acid ethyl ester [sic] | NMR 300 MHz (CDCl$_3$): 1H 6.88 ppm (d) J = 8.6 Hz; 3H 6.73–6.65 ppm (m); 1H 6.28 ppm (d) J = 15.4 Hz; 1H 5.90 ppm (s); 1H 5.73 ppm (s); 2H 4.11 ppm (q) J = 7.2 Hz; 2H 3.79 ppm (s); 3H 3.68 ppm (s); 2H 2.78 ppm (t) J = 7.5 Hz; 2H 1.49–1.36 ppm (m); 7H 1.32–1.18 ppm (m); 6H 1.08 ppm (s); 3H 0.83 ppm (t) J = 7 Hz. |
| 52B | | (2E, 4E)-5-(7-Methoxy-3,3-dimethyl-2,3-dihydrobenzo[b]-oxepin-5-yl)-3-pentylpenta-2,4-dienoic acid [sic] | M.p. 147–149° C. NMR 300 MHz (CDCl$_3$): 1H 10.8 ppm (s); 1H 6.98 ppm (d) J = 8.6 Hz; 1H 6.85 ppm (d) J = 15.4 Hz; 2H 6.79–6.74 ppm (m); 1H 6.40 ppm (d) J = 15.4 Hz; 1H 6.02 ppm (s); 1H 5.84 ppm (s); 2H 3.89 ppm (s); 3H 3.78 ppm (s); 2H 2.89 ppm (t) J = 7.4 Hz; H 1.59–1.55 ppm (m); 4H 1.44–1.30 ppm (m); 6H 1.18 ppm (s); 3H 0.93 ppm (t) J = 7 Hz. |

TABLE 2-continued

| | | | |
|---|---|---|---|
| 53A | 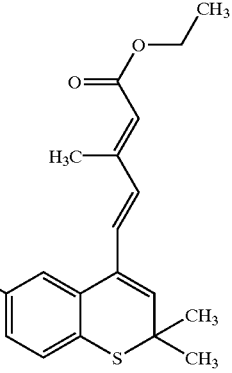 | (2E, 4E)-5-(2,2-Dimethyl-thiochromen-4-yl)-3-methyl-penta-2,4-dienoic acid ethyl ester | NMR 300 MHz (CDCl$_3$): 1.17–1.35 (9H, m), 2.30 (3H, s), 4.10 (2H, q), 5.78 (1H, s), 5.97 (1H, s), 6.48 (1H, d, J = 16 Hz), 6.73 (1H, d, J = 16 Hz), 7.04–7.30 (4H Ar, m). |
| 53B | 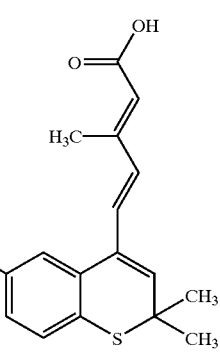 | (2E, 4E)-5-(2,2-Dimethylthio-chromene-4-yl)-3-methylpenta-2,4-dienoic acid [sic] | M.p. = 160–165° C. NMR 300 MHz (CDCl$_3$): 1.36 (6H, s), 2.32 (3H, s), 5.82 (1H, s), 6.00 (1H, s), 6.53 (1H, d, J = 16 Hz), 6.80 (1H, d, J = 16 Hz), 7.07–7.13 (2H, Ar, m), 7.26–7.31 (2H Ar, m). |
| 54A | 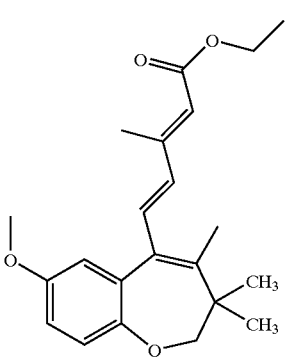 | (2E, 4E)-5-(7-Methoxy-3,3,4-trimethyl-2,3-dihydrobenzo[b]-oxepin-5-yl)-3-methylpenta-2,4-dienoic acid ethyl ester [sic] | NMR 300 MHz (CDCl$_3$) ppm: 1.02 (6H, s), 1.23 (3H, t, J = 7 Hz), 1.88 (3H, s), 2.33 (3H, s), 3.65 (3H, s), 3.88 (2H, s), 4.08(2H, q, J = 7Hz), 5.66 (1H, s), 6.06 (1H, d, J = 16 Hz), 6.67 (1H Ar, d, d, J = 3 Hz, J = 8 Hz), 6.77 (1H Ar, d, J = 3 Hz), 6.83 (1H, d, J = 16 Hz), 6.90 (1H, d, J = 8 Hz). |
| 54B | 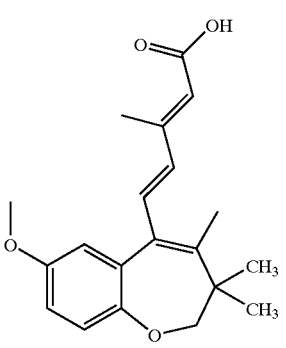 | (2E, 4E)-5-(7-Methoxy-3,3,4-trimethyl-2,3-dihydrobenzo[b]-oxepin-5-yl)-3-methylpenta-2,4-dienoic acid [sic] | M.p. = 129–130° C. NMR 300 MHz (CDCl$_3$) ppm: 1.12 (6H, s), 1.99 (3H, s), 2.44 (3H, s), 3.74 (3H, s), 3.98 (2H, s), 5.79 (1H, s), 6.13 (1H, d, J = 16 Hz), 6.72 (1H Ar, d, d, J = 3 Hz, J = 8 Hz), 6.80 (1H Ar, d, J = 3 Hz), 6.93 (1H, d, J = 16 Hz), 6.95 (1H Ar, d, J = 8 Hz) |

TABLE 2-continued

| | | | |
|---|---|---|---|
| 55A | 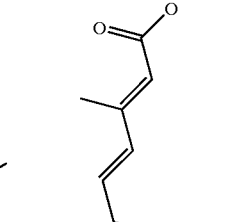 | (2E, 4E)-5-(7-Ethoxy-3,3-dimethyl-2,3-dihydrobenzo[b]- | NMR 300 MHz (CDCl$_3$) ppm: 6.92 (1H, d, d, J = 8.5 Hz) 6.79–6.70 (3H, m), 6.42 (1H, d, J = 15.4 Hz), 5.96 (1H, s), 5.83 (1H, s), 4.18 (2H, q, J = 6 Hz) 3.96 (2H, q, J = 6 Hz), 3.85 (2H, s), 2.36 (3H, s), 1.38 (3H, t, J = 6 Hz), 1.29 (3H, t, J = 6 Hz), 1.13 (6H, s). |
| 55B | 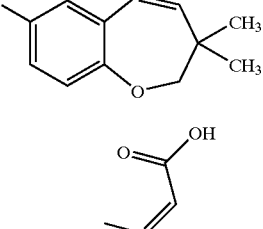 | (2E, 4E)-5-(7-Ethoxy-3,3-dimethyl-2,3-dihydrobenzo[b]-oxepin-5-yl)-3-methylpenta-2,4-dienoic acid [sic] | NMR 300 MHz (CDCl$_3$) ppm: 6.87 (1H, d, d, J = 2.5 Hz, J = 8.5 Hz), 6.79–6.44 (3H, m), 6.40 (1H, d, J = 15.4 Hz), 5.92 (1H, s), 5.81 (1H, s), 3.91 (2H, q), J = 7 Hz), 3.30 (2H, s), 2.3 (3H, s), 1.32 (3H, t, J = 7 Hz), 1.08 (6H, s). |

In addition, the following preparations illustrate the synthesis of intermediate compounds of use in the preparation of the compounds of Examples 1 to 31 above.

Preparation 1

3,3-Dimethyl-7-phenyl-3,4-dihydro-2H-benzoxepin-5-one 8.5 g of 7-bromo-3,3-dimethyl-3,4-dihydro-2H-benzoxepin-5-one (0.0316 mol), 95 ml of toluene, 34.7 ml of a 2M sodium carbonate solution, 46 ml of ethanol, 4.19 g of phenyboric [sic] acid (0.0344 mol, 1.09 equivalents) and 0.677 g of tetrakis(triphenyl-phosphine)palladium are changed to a 250 ml reactor. The reaction mixture is brought to reflux for 8 h and is then allowed to return to room temperature. The reaction mass is poured into a mixture of 70 ml of water, 56.8 ml of a 30% aqueous ammonium hydroxide solution and 78 ml of a 2M aqueous sodium carbonate solution. The catalyst is filtered off through silica. Extraction is then carried out 3 times with 100 ml of ethyl acetate and the organic phases are washed with 3 times 100 ml of water and dried over anhydrous sodium sulphate before being concentrated under reduced pressure. 14 g of an oil are isolated, which oil is purified by column chromatography using a 4/1 hexane/ethyl acetate mixture. 8.5 g of the title compound are thus obtained in the form of a liquid.

$^1$H NMR (CDCl$_3$, 300 MHz) δ (ppm): 7.88–7.25 (8H, m), 3.98 (2H, s), 2.74 (2H, s), 1.15 (6H, s).

Preparation 2

(4-para-Chlorophenyl) (3,3,5-trimethyl-2,3-dihydrobenzoxepin-7-yl) ketone [sic]

0.627 g of magnesium turning [sic] (0.0258 mol), 20 ml of anhydrous tetrahydrofuran and an iodine crystal are introduced into a 250 ml reactor. A mixture of 8.3 g of 7-bromo-3,3,5-trimethyl-2,3-dihydrobenzoxepine in 30 ml of anhydrous tetrahydrofuran is slowly added to this solution. The combined mixture is brought to reflux for 1.5 h and then the reaction mixture is allowed to return to room temperature (solution A).

5 g of para-chlorobenzoyl chloride and 20 ml of anhydrous tetrahydrofuran are introduced into a second 250 ml reactor. This solution is cooled to 0° C. and then the solution A prepared above is slowly added thereto, so as to maintain the temperature of the reaction mixture below 5° C. The combined mixture is allowed to return to room temperature and then the reaction mixture is kept stirring for 20 h. After cooling to 5° C., hydrolysis is carried out by slow addition of 3.2 ml of a 1N aqueous hydrochloric acid solution and then the mixture is diluted with water and extracted with 3 times 100 ml of diethyl ether. The organic phase is washed with a 1N aqueous sodium hydroxide solution and then with 2 times 100 ml of water and dried over anhydrous sodium sulphate before being concentrated under reduced pressure. 10.5 g of an oil are thus obtained, which oil is purified by column chromatography using a 10/1 hexane/ethyl acetate mixture as eluant. After purification, 3.6 g of the title compound are isolated in the form of a liquid. Yield 38.7%.

$^1$H NMR (DMSO [sic], 300 MHz) δ (ppm): 8.04–6.96 (7H, m), 5.73 (1H, s), 3.83 (2H, s), 2.06 (3H, s), 1.05 (6H, s).

Preparation 3

4-Methyl-3-formyl-2H-1-benzopyran 6.3 g (40.63 mmol) of POCl$_3$ are run, at 0° C., into a 50 ml three-necked flask, maintained under an inert atmosphere, containing 3.0 g (40.63 mmol) of dimethylformamide. The reaction mixture is maintained at 5° C. for 15 minutes and then a solution of 4.8 g (32.5 mmol) of 4-methyl-2H-1-benzopyran in 25 ml of methylene chloride is run in at this temperature.

The reaction mixture is allowed to return to room temperature and is kept stirring for 2 hours. The reaction mixture is then quickly poured into a mixture of water and ice and then extracted with ethyl acetate. The organic phase is washed with a 5% aqueous sodium bicarbonate solution and then with water. After drying over anhydrous sodium sulphate, the organic phase is concentrated under reduced pressure. An oil is obtained, which oil slowly crystallizes. It is recrystallized from 25 ml of isopropyl ether. 2.0 g of the title compound are thus obtained in the form of a solid, the melting point of which is between 68 and 70° C. (yield=35%).

$^1$H NMR (CDCl$_3$, 300 MHz) δ (ppm): 2.4 (3H, s), 4.8 (2H, s), 6.8–7.0 (2H, m), 7.2–7.4 (2H, m), 10.1 (1H, s).

M.p.=68–70° C.

Preparation 4

4-Phenyl-3-formyl-2H-1-benzopyran 71 ml (0.773 mol) of phosphorus oxychloride are added dropwise to 300 ml of dimethylformamide maintained at 0° C. The reaction mixture is left stirring for 20 minutes at a temperature of between 0 and 5° C. A solution of 16.1 g (77.3 mmol) of 4-phenyl-2H-1-benzopyran in 22.5 ml of dimethylformamide is then added to the reaction mixture. The reaction mixture is allowed to return to room temperature and is then brought to 60° C. for 7 hours. The reaction mixture is then poured into a mixture of ice and water which is neutralized with NaOH. The organic phase is extracted with ethyl acetate and then the organic phase is washed 3 times with water. After drying over anhydrous sodium sulphate, the organic phase is concentrated under reduced pressure. A pasty solid is thus obtained, which solid, after silica column chromatography using a 1/1 methylene chloride/cyclohexane mixture as eluant, results in 15.3 g of the title compound in the form of a yellow solid, the melting point of which is 82–83° C. (yield=83%).

$^1$H NMR (CDCl$_3$, 300 MHz) δ (ppm): 5 (2H, s), 6.79 to 6.89 (3H, m), 7.21 to 7.26 (3H, m), from 7.39 to 7.42 (3H, m), 9.38 (1H, s).

The characterization physiocochemical data of other intermediate carboxaldehydes are specified in Table 3.

The characterization physiochemical data of some intermediate products have been reported in the following Table 3.

TABLE 3

| Compound | $^1$H NMR (CDCl$_3$, 300 MHz) δ (ppm): |
|---|---|
| 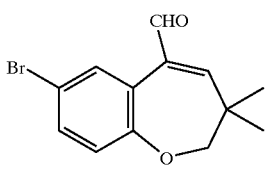 | 9.52(1H, s), 8.2(1H, s), 7.29–6.84(2H, m), 6.52(1H, s), 3.84(2H, s), 1.19(6H, s) |
| 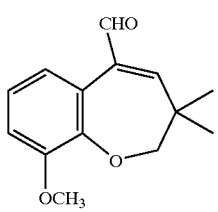 | 9.57(1H, s), 7.49(1H, m), 6.92(2H, m), 6.51(1H, s), 3.90(2H, s), 3.8(3H, s), 1.19(6H, s) |
| 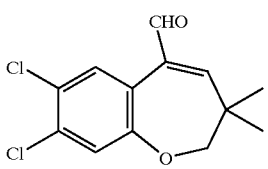 | 9.5(1H, s), 8.25(1H, s), 7.09(1H, s), 6.53(1H, s), 3.84(2H, s), 1.19(6H, s) |
| 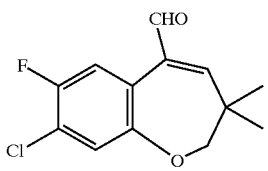<br>M.p. = 114° C. | 9.49(1H, s), 8.02(1H, d, J=11.55Hz), 7.02(1H, d, J=6.83Hz), 6.53(1H, s), 3.84(2H, s), 1.19(6H, s) |
| 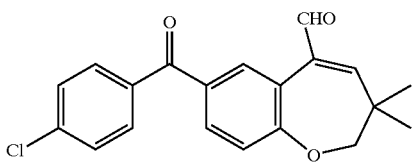 | 9.52(1H, s), 8.46(1H, d, J=2.1Hz), 7.78–7.69(3H, m), 7.44–7.40(2H, m), 7.08(2H, d, J=8.5Hz), 6.56(1H, s), 3.92(2H, s), 1.22(6H, s) |

TABLE 3-continued
| Compound | $^1$H NMR (CDCl$_3$, 300 MHz) δ (ppm): |
|---|---|
| 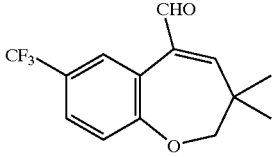 | 9.54(1H, s), 8.40(1H, s), 7.44–7.38(1H, m), 7.06(1H, d, J=9Hz), 6.57(1H, s), 3.97(2H, s), 1.20(6H, s) |
| 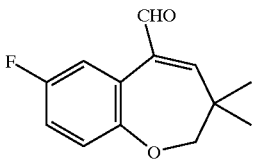 | 9.52(1H, s), 7.85–7.80(1H, m), 6.94–6.83(2H, m), 6.52(1H, s), 3.83(2H, s), 1.19(6H, s) |
| 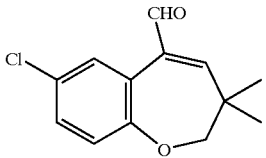 | 9.52(1H, s), 8.06(1H, d), 7.15–7.11(1H, m), 6.90(1H, d, J=8.6Hz), 6.52(1H, s), 3.84(2H, s), 1.19(6H, s) |
| 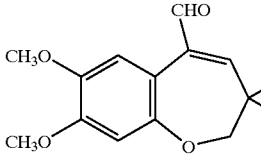 | 9.5(1H, s), 7.74(1H, s), 6.53(1H, s), 6.37(1H, s), 3.83(2H, s), 3.79(3H, s), 3.74(3H, s), 1.17(6H, s) |
| 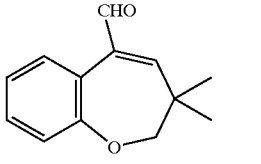 | 9.56(1H, s), 7.99–7.95(1H, m), 7.20–6.95(3H, m), 6.47(1H, s), 3.85(2H, s), 1.18(6H, s) |
| 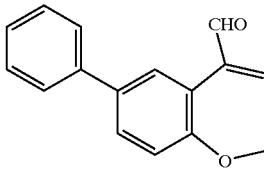 | 9.61(1H, s), 8.26(1H, s), 7.54–7.03(7H, m), 6.52(1H, s), 3.90(2H, s), 1.2(6H, s) |
| 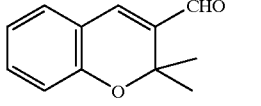<br>B.p. (0.6 mm Hg) = 105–115° C. | 1.42(6H, s), 6.6 to 6.62(1H, m), 6.7 to 6.73(1H, m), 6.89(1H, s), 6.95 to 6.98(1H, m), 7.05 to 7.09(1H, m), 9.25(1H, s) |
| 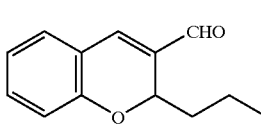<br>B.p. (0.4 mm Hg) = 160–165° C. | 0.8(3H, t, J=7Hz), 1.2–1.3(6H, m), 1.5(1H, m), 1.7(1H, m), 1.9(2H, m), 2.1–2.2(2H, m), 5.2–5.4(3H, m), 6.8–6.9(2H, m), 7.1–7.2(3H, m), 9.5(1H, s) |
| 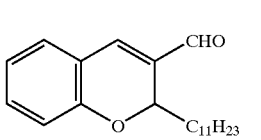<br>B.p. (0.3 mm Hg) = 177–180° C. | 0.8(3H, t, J=7Hz), 1.2–1.7(20H, m), 5.2(1H, d, J=9Hz), 6.8–6.9(2H, m), 7.1–7.2(3H, m), 9.5(1H, s) |

TABLE 3-continued

| Compound | $^1$H NMR (CDCl$_3$, 300 MHz) δ (ppm): |
|---|---|
| 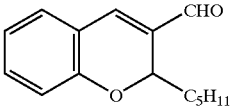<br>B.p. (0.3 mm Hg) = 126–131° C. | 0.8–1.7(11H, m), 5.2(1H, d, J=9Hz),<br>6.8–6.9(m, 2H), 7.1–7.2(3H, m), 9.5(1H, s) |
| 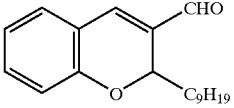<br>B.p. (0.4 mm Hg) = 165–172° C. | 0.8(3H, t, J=7Hz), 1.2–1.7(16H, m),<br>5.2(1H, d, J=9Hz), 6.8–6.9(2H, m),<br>7.1–7.2(3H, m), 9.5(1H, s) |

The characterization physiocochemical data of a few intermediates of 5-methyl-2,3-dihydrobenzoxepine type are specified in Table 4.

TABLE 4

| Compound | $^1$H NMR (CDCl$_3$, 300 MHz) δ (ppm): |
|---|---|
| 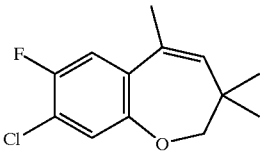 | 7.08(1H, d, J=11.5Hz), 6.95(1H, d, J=6.95Hz),<br>5.68(1H, s), 3.74(2H, s), 2.01(3H, s), 1.02(6H, s) |
| 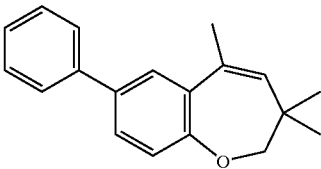 | 6.95–7.5(8H, m), 5.75(1H, s), 3.77(2H, s),<br>2.11(3H, s), 1.05(6H, s) |
| 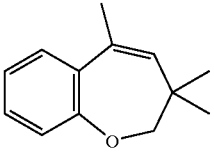 | 7.34–6.89(4H, m), 5.63(1H, s), 3.77(2H, s),<br>2.07(3H, s), 1.03(6H, s) |
| 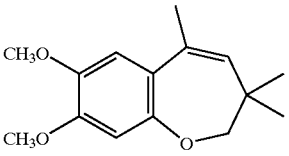 | 6.81(1H, s), 6.50(1H, s), 5.53(1H, s), 3.78(3H, s),<br>3.77(3H, s), 3.76(2H, s), 2.06(3H, s), 1.02(6H, s) |
| 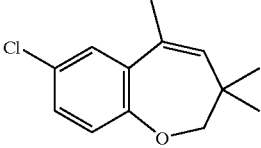 | 7.26(1H, d, J=2.5Hz), 7.03–6.98(1H, m),<br>6.83(1H, d, J=8.5Hz), 5.67(1H, s), 3.74(2H, s),<br>1.68(3H, s), 1.02(6H, s) |
| 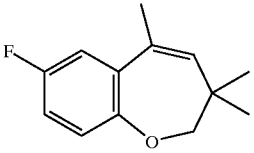 | 7.01–6.74(3H, m), 5.67(1H, s), 3.74(2H, s),<br>2.03(3H, s), 1.02(6H, s) |

TABLE 4-continued
| Compound | $^1$H NMR (CDCl$_3$, 300 MHz) δ (ppm): |
|---|---|
| 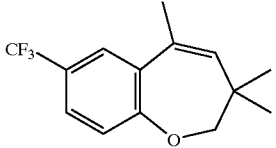 | 7.56–7.49(1H, m), 7.33–7.28(1H, m), 7.00–6.86(1H, m), 5.73(1H, s), 3.79(2H, m), 2.09(3H, s), 1.05(6H, s) |
| 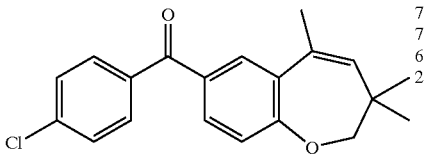 | 7.85(1H, d, J=1.9Hz), 7.66–7.63(2H, m), 7.52–7.48(1H, m), 7.39–7.36(2H, m), 6.97(1H, d, J=8.3Hz), 5.70(1H, s), 3.83(2H, s), 2.06(3H, s), 1.05(6H, s) |
| 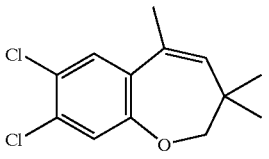 | 7.34(1H, s), 7(1H, s), 5.68(1H, s), 3.74(2H, s), 2.02(3H, s), 1.02(6H, s) |
| 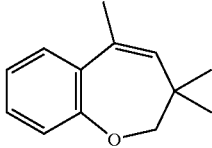 | 7.34–6.89(4H, m), 5.63(1H, s), 3.77(2H, s), 2.07(3H, s), 1.03(6H, s) |
| 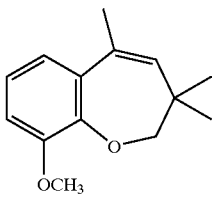 | 7.19–6.73(3H, m), 5.65(1H, s), 3.90(2H, s), 3.85(3H, s), 2.06(3H, s), 1.43(6H, s) |
| 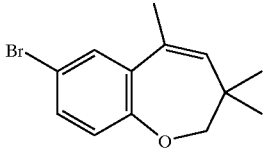 | 7.4–6.68(3H, m), 5.67(1H, s), 3.75(2H, s), 2.04(3H, s), 1.03(3H, s) |
The characterization physicochemical data of a few 5-bromomethyl-2,3-dihydrobenzoxepine derivatives are specified in Table 5.
TABLE 5
| Compound | $^1$H NMR (CDCl$_3$, 300 MHz) δ (ppm): |
|---|---|
| 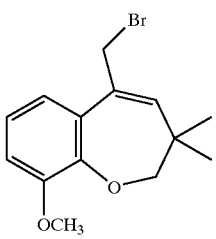 | 7.26–6.77(3H, m), 6.03(1H, s), 4.3(2H, s), 3.84(2H, s), 3.78(3H, s), 1.07(6H, s) |

TABLE 5-continued
| Compound | $^1$H NMR (CDCl$_3$, 300 MHz) δ (ppm): |
|---|---|
| 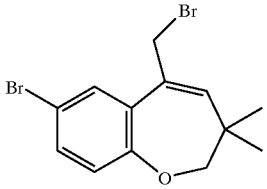 | 7.76–6.75(3H, m), 6.06(1H, s), 4.26(2H, s), 3.78(3H, s), 1.06(3H, s) |
| 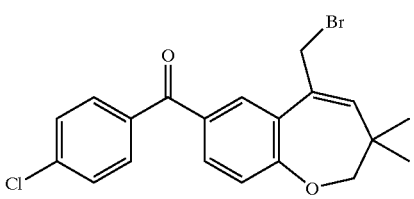 | 7.96(1H, d, J=9Hz), 7.74–7.61(3H, m), 7.39(2H, d, J=8.5Hz), 7.04(1H, d, J=8.4Hz), 6.11(1H, s), 4.27(2H, s), 3.84(2H, s), 1.18(6H, s) |
| 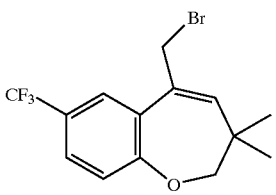 | 7.56–6.99(3H, m), 5.73(1H, s), 4.29(2H, s), 3.80(2H, s), 1.04(6H, s) |
|  | 7.25–7.18(1H, m), 6.89–6.80(2H, m), 6.06(1H, s), 4.24(2H, s), 3.75(2H, s), 1.06(6H, s) |
| 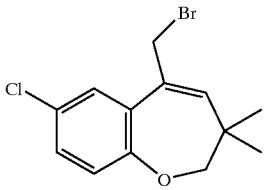 | 7.48(1H, d, J=2.5Hz), 7.09–7.05(1H, m), 6.87(1H, d, J=8.6Hz), 6.60(1H, s), 4.25(2H, s), 3.75(2H, s), 1.06(6H, s) |
| 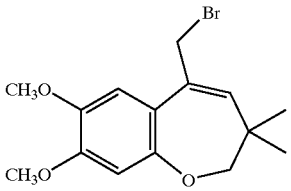 | 7.06(1H, s), 6.49(1H, s), 5.9(1H, s), 4.2(2H, s), 3.87(3H, s), 3.83(3H, s), 3.79(2H, s), 1.05(6H, s) |
| 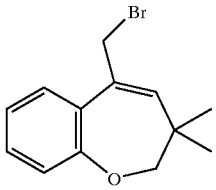 | 7.55–7.52(1H, m), 7.18–6.93(3H, m), 6.02(1H, s), 4.31(2H, s), 3.78(2H, s), 1.05(6H, s) |

TABLE 5-continued

| Compound | $^1$H NMR (CDCl$_3$, 300 MHz) δ (ppm): |
|---|---|
| (structure: 7-chloro-8-fluoro-5-(bromomethyl)-3,3-dimethyl-2,3-dihydro-1-benzoxepine) | 7.3(1H, d), 7(1H, d), 6.06(1H, s), 4.21(2H, s), 3.74(2H, s), 1.05(6H, s) |
| (structure: 7-phenyl-5-(bromomethyl)-3,3-dimethyl-2,3-dihydro-1-benzoxepine) | 7.78–6.94(8H, m), 6.07(1H, s), 4.36(2H, s), 3.75(2H, s), 1.1(6H, s) |
| (structure: 7,8-dichloro-5-(bromomethyl)-3,3-dimethyl-2,3-dihydro-1-benzoxepine) | 7.6(1H, s), 7(1H, s), 6.06(1H, s), 4.23(2H, s), 3.75(2H, s), 1.04(6H, s) |

What is claimed is:
1. A compound of formula:

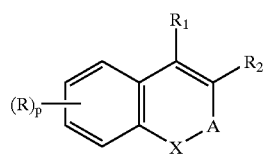

(I)

wherein

X is O or S;

A is —(CH$_2$)$_x$—CO—(CH$_2$)$_t$— or
—(CH$_2$)$_x$—CR$_3$R$_4$—(CH$_2$)$_t$—
in which s and t are 0 or one of s and t is 0 and the other is 1;

R$_4$ is a hydrogen atom or a (C$_1$–C$_{15}$) alkyl group;

R$_1$ and R$_2$ are, independently, Z; a hydrogen atom; a (C$_1$–C$_{18}$) alkyl group; a (C$_2$–C$_{18}$) alkenyl group; a (C$_2$–C$_{18}$) alkynyl group; a (C$_6$–C$_{10}$) aryl group optionally substituted by a halogen atom, by an optionally halogenated (C$_1$–C$_5$) alkyl group or by an optionally halogenated (C$_1$–C$_5$) alkoxy group; or a mono- or bicyclic (C$_4$–C$_{12}$) heteroaryl group having one or more heteroatoms selected from the group consisting of O, N and S, which is optionally substituted by a halogen atom, by an optionally halogenated (C$_1$–C$_5$) alkyl group or by an optionally halogenated (C$_1$–C$_5$) alkoxy group;

R$_3$ has any one of the meanings of R$_1$ and R$_2$, with the exception of Z; or R$_3$ and R$_4$ together, form a (C$_2$–C$_6$) alkylene chain optionally substituted by a halogen atom or by optionally halogenated (C$_1$–C$_5$) alkoxy;

R is a halogen atom; a cyano group; a nitro group; a carboxy group; an optionally halogenated (C$_1$–C$_{18}$) alkoxycarbonyl group; an R$_a$—CO—NH— or R$_a$R$_b$N—CO— group, an optionally halogenated (C$_1$–C$_{18}$) alkyl group; optionally halogenated (C$_1$–C$_{18}$) alkoxy; (C$_6$–C$_{10}$) aryl, (C$_6$–C$_{10}$) aryl (C$_1$–C$_5$) alkyl; (C$_6$–C$_{10}$) aryloxy, (C$_3$–C$_{12}$) cycloalkyl, (C$_3$–C$_{12}$) cycloalkenyl, (C$_3$–C$_{12}$) cycloalkyloxy or (C$_3$–C$_{12}$) cycloalkenyloxy in which any aryl, cycloalkyl and cycloalkenyl are optionally substituted by a halogen atom, by optionally halogenated (C$_1$–C$_5$) alkyl or by optionally halogenated (C$_1$–C$_5$) alkoxy;

R$_a$ and R$_b$ are, independently, optionally halogenated (C$_1$–C$_{18}$) alkyl; a hydrogen atom; (C$_6$–C$_{10}$) aryl or (C$_6$–C$_{10}$) aryl (C$_1$–C$_5$) alkyl, wherein, any aryl is optionally substituted by a halogen atom, by an optionally halogenated (C$_1$–C$_5$) alkyl group or by an optionally halogenated (C$_1$–C$_5$) alkoxy group); (C$_3$–C$_{12}$) cycloalkyl optionally substituted by a halogen atom, by an optionally halogenated C$_1$–C$_5$ alkyl group or by an optionally halogenated (C$_1$–C$_5$) alkoxy group;

p is 0, 1, 2, 3 or 4;

Z is

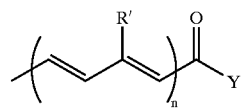

n is 1 or 2;

R' are, each independently, a hydrogen atom; a (C$_1$–C$_5$) alkyl group; a (C$_6$–C$_{10}$) aryl group optionally substituted by a halogen atom, by an optionally halogenated (C$_1$–C$_5$) alkyl group or by optionally halogenated (C$_1$–C$_5$) alkoxy; or a mono- or bicyclic (C$_4$–C$_{12}$) heteroaryl group having one or more heteroatoms selected from the group consisting of O, N and S, which is optionally substituted by a halogen atom, by an optionally halogenated ($C_1$–$C_5$) alkyl group or by an optionally halogenated ($C_1$–$C_5$) alkoxy group;

Y is —OH; ($C_1$–$C_5$) alkoxy; or —$NR_cR_d$ $R_c$ and $R_d$ are, independently, a hydrogen atom; ($C_1$–$C_5$) alkyl; ($C_3$–$C_5$) alkyl; ($C_3$–$C_8$) cycloalkyl optionally substituted by a halogen atom, by optionally halogenated ($C_1$–$C_5$) alkyl or by optionally halogenated ($C_1$–$C_5$) alkoxy; ($C_6$–$C_{10}$) aryl optionally substituted by a halogen atom, by optionally halogenated ($C_1$–$C_5$) alkyl or by optionally halogenated ($C_1$–$C_5$) alkoxy;

wherein $R_1$ and $R_2$ are not both Z;

or a pharmaceutically acceptable salt thereof.

2. A compound of formula I according to claim 1, wherein A is —$(CH_2)_s$—$CR_3R_4$—$(CH_2)_t$— in which s, t, $R_3$ and $R_4$ are as defined in claim 1.

3. A compound of formula I according to claim 1, wherein

X is O;

A is —$CR_3R_4$— or —$CH_2$—$CR_3R_4$— in which the unsubstituted methylene group is bonded to X;

$R_1$ and $R_2$ are, independently, Z; H; ($C_1$–$C_{15}$) alkyl; ($C_2$–$C_{15}$) alkenyl; or phenyl optionally substituted by ($C_1$–$C_5$) alkyl, ($C_1$–$C_5$) alkoxy, a halogen atom or —$CF_3$;

$R_3$ has any one of the meanings of $R_1$ and $R_2$, with the exception of Z;

R is ($C_1$–$C_9$) alkyl; ($C_1$–$C_5$) alkoxy; phenyl or phenylcarbonyl optionally substituted by a halogen atom, ($C_1$–$C_5$) alkyl, ($C_1$–$C_5$) alkoxy, —$CF_3$ or —$OFC_3$; a halogen atom; —$CF_3$ or —$OCF_3$;

Z is

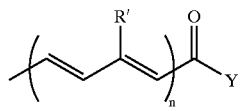

n is 1; and

R' is ($C_1$–$C_5$) alkyl.

4. A compound according to claim 1, wherein

X is O;

A is —$CR_3R_4$—; and

Z is

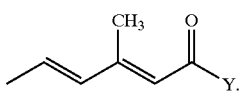

5. A compound according to claim 1, wherein

X is O;

A is —$CH_2$—$CR_3R_4$— in which the unsubstituted methylene group is bonded to X;

$R_1$ and $R_2$ are, independently, Z, a hydrogen atom or ($C_1$–$C_5$) alkyl;

$R_3$ has any one of the meanings of $R_1$ and $R_2$, with the exception of Z;

Z is

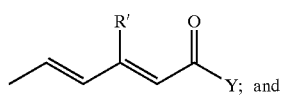

R' is methyl or phenyl.

6. A compound according to claim 1, wherein Y is —OH; ($C_1$–$C_5$) alkoxy; or —$NR_cR_d$ in which $R_c$ and $R_d$ are as defined in claim 1.

7. A compound according to claim 1, wherein p is 0, 1 or 2.

8. A compound according to claim 1, which is (2E, 4E)-5-(2-pentyl-2H-1-benzopyran-3-yl)-3-methylpenta-2,4-dienoic acid;

(2Z, 4E)-5-(2-pentyl-2H-1-benzopyran-3-yl)-3-methylpenta-2,4-dienoic acid;

(2E, 4E)-5-(2,2-dimethyl-6-methoxy-2H-1-benzopyran-3-yl)-3-methylpenta-2,4-dienoic acid;

(2E, 4E)-5-(2H-1-benzopyran-3-yl)-3-methylpenta-2,4-dienoic acid;

(2E, 4E)-5-(2,2-dimethyl-2H-1-benzopyran-3-yl)-3-methylpenta-2,4-dienoic acid;

(2Z, 4E)-5-(2,2-dimethyl-2H-1-benzopyran-3-yl)-3-methylpenta-2,4-dienoic acid;

(2E, 4E)-5-[2-(non-6-enyl)-2H-1-benzopyran-3-yl]-3-methylpenta-2,4-dienoic acid;

(2E, 4E)-5-(4-phenyl-2H-1-benzopyran-3-yl)-3-methylpenta-2,4-dienoic acid;

(2E, 4E)-5-(6-nonyl-2H-1-benzopyran-3-yl)-3-methylpenta-2,4-dienoic acid;

(2E, 4E)-5-(6-phenyl-2H-1-benzopyran-3-yl)-3-methylpenta-2,4-dienoic acid;

(2E, 4E)-5-(2-nonyl-2H-1-benzopyran-3-yl)-3-methylpenta-2,4-dienoic acid;

(2E, 4E)-5-(4-methyl-2H-1-benzopyran-3-yl)-3-methylpenta-2,4-dienoic acid;

(2Z, 4E)-5-(2H-1-benzopyran-3-yl)-3-methylpenta-2,4-dienoic acid;

(2E, 4E)-5-(2-undecanyl-2H-1-benzopyran-3-yl)-3-methylpenta-2,4-dienoic acid;

(2E, 4E)-5-(2--henyl-2H-1-benzopyran-3-yl)-3-methylpenta-2,4-dienoic acid;

(2E, 4E)-5-(5-methyl-2,3-dihydrobenzoxepin-4-yl)-3-methylpenta-2,4-dienoic acid;

(2E, 4E)-5-(3,3-dimethyl-7-methoxy-2,3-dihydrobenzoxepin-5-yl)-3-methylpenta-2,4-dienoic acid;

(2E, 4E)-5-(2,3-dihydrobenzoxepin-4-yl)-3-methylpena-2,4-dienoic acid;

(2E, 4E)-5-(3,3-dimethyl-7-methoxy-2,3-dihydrobenzoxepin-5-yl)-3-phenylpenta-2,4-dienoic acid;

(2Z, 4E)-5-(3,3-dimethyl-7-methoxy-2,3-dihydrobenzoxepin-5-yl)-3-phenylpenta-2,4-dienoic acid;

(2Z, 4E)-5-(3,3-dimethyl-7-methoxy-2,3-dihydrobenzoxepin-5-yl)-3-methylpenta-2,4-dienoic acid;

(2E, 4E)-5-(3,3-dimethyl-7,8-dimethoxy-2,3-dihydrobenzoxepin-5-yl)-3-methylpenta-2,4-dienoic acid;

(2E, 4E)-5-(3,3-dimethyl-2,3-dihydrobenzoxepin-5-yl)-3-methylpenta-2,4-dienoic acid;

(2E, 4E)-5-(3,3-dimethyl-2,3-dihydro-7-(para-chlorobenzoyl) benzoxepin-5-yl)-3-methylpenta-2,4-dienoic acid;

(2E, 4E)-5-(3,3-dimethyl-7-chloro-2,3-dihydrobenzoxepin-5-yl)-3-methylpenta-2,4-dienoic acid;

(2E, 4E)-5-(3,3-dimethyl-7,8-dichloro-2,3-dihydrobenzoxepin-5-yl)-3-methylpenta-2,4-dienoic acid;

(2E, 4E)-5-(3,3-dimethyl-7-bromo-2,3-dihydrobenzoxepin-5-yl)-3-methylpenta-2,4-dienoic acid;

(2E, 4E)-5-(3,3-dimethyl-7-fluoro-8-chloro-2,3-dihydrobenzoxepin-5-yl)-3-methylpenta-2,4-dienoic acid;

(2E, 4E)-5-(3,3-dimethyl-7-fluoro-2,3-dihydrobenzoxepin-5-yl)-3-methylpenta-2,4-dienoic acid;

(2E, 4E)-5-(3,3-dimethyl-7-trifluoromethyl-2,3-dihydrobenzoxepin-5-yl)-3-methylpenta-2,4-dienoic acid;

(2E, 4E)-5-(3,3-dimethyl-7-phenyl-2,3-dihydrobenzoxepin-5-yl)-3-methylpenta-2,4-dienoic acid;

(2E, 4E)-5-(3,3,7-trimethyl-2,3-dihydrobenzoxepin-5-yl)-3-methylpenta-2,4-dienoic acid;

(2E, 4E)-5-(3,3-dimethyl-2,3-dihydrobenzoxepin-5-yl)-3-methylpenta-2,4-dienoic acid; or (2E, 4E)-5-(9-methoxy-3,3-dimethyl-2,3-dihydrobenzoxepin-5-yl)-3-methylpenta-2,4-dienoic acid;

or a pharmaceutically acceptable ester thereof.

9. A process for preparing a compound of formula (I) according to claim 1 in which n is 1, comprising a) preparing an ylide by reacting a base with a phosphonate of formula (IIa)

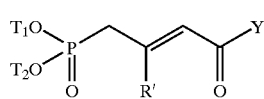
(IIa)

in which R' is as defined in claim 1;

$T_1$ and $T_2$ are, independently, $(C_1-C_5)$ alkyl; and

Y is $(C_1-C_5)$ alkoxy, or by reacting a base with a phosphonium salt of formula (IIb)

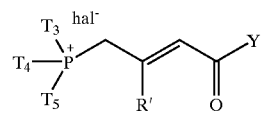
(IIb)

in which R' is as defined in claim 1;

$T_3$, $T_4$ and $T_5$ are, independently, $(C_1-C_5)$ alkyl or $(C_6-C_{10})$ aryl optionally substituted by $(C_1-C_5)$ alkyl;

Y is $(C_1-C_5)$ alkoxy; and hal is a halogen atom;

b) reacting the ylide with an aldehyde of formula (III)

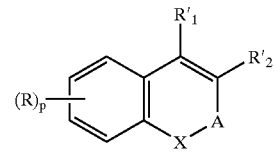
(III)

in which

R, p, X and A are as defined in claim 1;

one of $R'_1$ and $R'_2$ is —CHO and the other has one of the meanings of $R_1$ and $R_2$ in claim 1 with the exception of Z, to obtain a compound of formula (I) in which n is 1 and Y is $(C_1-C_5)$ alkoxy;

c) optionally, converting the resultant compound of formula (I) in an acidic or basic medium into a carboxylic acid of formula (I) in which Y is OH;

d) optionally, reacting the resultant carboxylic acid group of the compound of formula (I) with an amine of formula $HNR_cR_d$, in which $R_c$ and $R_d$ are as defined in claim 1, to obtain a compound of formula (I) in which Y is —$NR_cR_d$.

10. A process for preparing a compound of formula (I) according to claim 1 in which n is 2, comprising a) preparing an ylide by reacting a base with a phosphonate of formula (IVa)

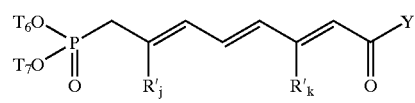
(IVa)

in which $R'_j$ and $R'_k$ are, independently, an R' group as defined in claim 1;

$T_6$ and $T_7$ are, independently, $(C_1-C_5)$ alkyl; and

Y is $(C_1-C_5)$ alkoxy;

or by reacting a base with a phosphonium salt of formula (IVb)

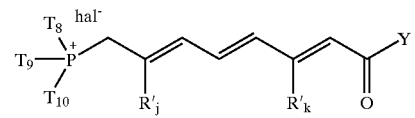
(IVb)

in which $R'_j$ and $R'_k$ are, independently an R' group as defined in claim 1;

$T_8$, $T_9$ and $T_{10}$ are, independently, $(C_1-C_5)$ alkyl or $(C_6-C_{10})$ aryl optionally substituted by $(C_1-C_5)$ alkyl;

Y is $(C_1-C_5)$ alkoxy; and hal is a halogen;

b) reacting the ylide with an aldehyde of formula (III)

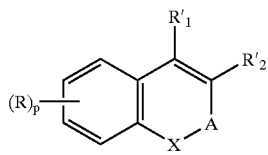

(III)

in which

R, p, X and A are as defined in claim 1;

one of $R'_1$ and $R'_2$ is —CHO and the other has one of the meanings of $R_1$ and $R_2$ in claim 1 with the exception of Z, to obtain a compound of formula I in which n is 2 and Y is $(C_1-C_5)$ alkoxy;

c) optionally, converting the resultant compound of formula I in an acidic or basic medium into a carboxylic acid of formula (I) in which Y is OH;

d) optionally, reacting the resultant carboxylic acid group of the compound of formula (I) with an amine of formula $HNR_cR_d$, in which $R_c$ and $R_d$ are as defined in claim 1, to obtain a compound of formula (I) in which Y is —$NR_cR_d$.

11. A process according to claim 9, wherein the ylide is prepared by reacting a base with a phosphonate.

12. A process according to claim 9, wherein the base is an alkali metal hydride, an alkali metal carbonate, an alkali metal amide, a $(C_1-C_{10})$ alkyllithium or an alkali metal alkoxide.

13. A process according to claim 9, wherein step a) is carried out in the presence of an aprotic solvent which is selected from the group consisting of an aromatic hydrocarbon, an ester, or a mixture thereof.

14. A process according to claim 9, wherein the aldehyde of formula (III) is added to the resultant reaction mixture of step a).

15. A process according to claim 9, wherein the ylide is prepared by reacting a metal hydride with a phosphonate at a temperature of –10° C. to 50° C.

16. A process according to claim 9, wherein the ylide is prepared by reacting an alkali metal alkoxide with a phosphonate at a temperature of 10° C. to 100° C.

17. A process according to claim 9, wherein the reaction of the ylide with the aldehyde of formula (III) is carried out in an aprotic solvent at a temperature of –10° C. to 50° C.

18. A compound of formula (IIIa)

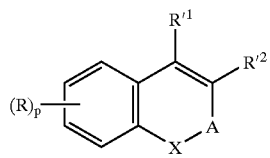

(IIIa)

wherein

A is —$(CH_2)_s$—$CR_3R_4$—$(CH_2)_t$— wherein one of s and t is 0 and the other is 1;

$R_4$ is a hydrogen atom or a $(C_1-C_{15})$ alkyl group;

$R_3$ is a hydrogen atom; a $C_1-C_{18}$ alkyl group; a $(C_2-C_{18})$ alkenyl group; a $(C_2-C_{18})$ alkynyl group; a $(C_6-C_{10})$ aryl group optionally substituted by a halogen atom, by an optionally halogenated $(C_1-C_5)$ alkyl group or by an optionally halogenated $(C_1-C_5)$ alkoxy group; or a mono- or bicyclic $(C_4-C_{12})$ heteroaryl group having one or more heteroatoms selected from the group consisting of O, N and S, which is optionally substituted by a halogen atom, by an optionally halogenated $(C_1-C_5)$ alkyl group or by an optionally halogenated $(C_1-C_5)$ alkoxy group; or $R_3$ and $R_4$ together, form a $(C_2-C_6)$ alkylene chain optionally substituted by a halogen atom or by optionally halogenated $(C_1-C_5)$ alkoxy;

R is a halogen atom; a cyano group; a nitro group; a carboxy group; an optionally halogenated $(C_1-C_{18})$ alkoxycarbonyl group; an $R_a$—CO—NH— or $R_aR_bN$—CO— group, an optionally halogenated $(C_1-C_{18})$ alkyl group; optionally halogenated $(C_1-C_{18})$ alkoxy; $(C_6-C_{10})$ aryl, $(C_6-C_{10})$ aryl $(C_1-C_5)$ alkyl, $(C_6-C_{10})$ aryloxy, $(C_3-C_{12})$ cycloalkyl, $(C_3-C_{12})$ cycloalkenyl, $(C_3-C_{12})$ cycloalkyloxy or $(C_3-C_{12})$ cycloalkenyloxy in which any aryl, cycloalkyl and cycloalkenyl are optionally substituted by a halogen atom, by optionally halogenated $(C_1-C_5)$ alkyl or by optionally halogenated $(C_1-C_5)$ alkoxy;

X is O or S;

p is, 0, 1, 2, 3 or 4;

one of $R'_1$ and $R'_2$ is —CHO and the other is a hydrogen atom; a $(C_1-C_{18})$ alkyl group; a $(C_2-C_{18})$ alkenyl group; a $(C_2-C_{18})$ alkynyl group; a $(C_6-C_{10})$ aryl group optionally substituted by a halogen atom, by an optionally halogenated $(C_1-C_5)$ alkyl group or by an optionally halogenated $(C_1-C_5)$ alkoxy group; or a mono- or bicyclic $(C_4-C_{12})$ heteroaryl group having one or more heteroatoms selected from the group consisting of O, N and S, which is optionally substituted by a halogen atom, by an optionally halogenated $(C_1-C_5)$ alkyl group or by an optionally halogenated $(C_1-C_5)$ alkoxy group.

19. A compound of formula

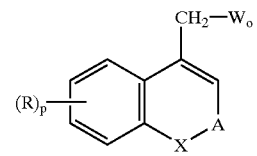

wherein

A is —$(CH_2)_s$—$CR_3R_4$—$(CH_2)_t$— wherein one of s and t is 0 and the other is 1;

$R_4$ is a hydrogen atom or a $(C_1-C_{15})$ alkyl group;

$R_3$ is a hydrogen atom; a $(C_1-C_{18})$ alkyl group; a $(C_2-C_{18})$ alkenyl group; a $(C_2-C_{18})$ alkynyl group; a $(C_6-C_{10})$ aryl group optionally substituted by a halogen atom, by an optionally halogenated $(C_1-C_5)$ alkyl group or by an optionally halogenated $(C_1-C_5)$ alkoxy group; or a mono- or bicyclic $(C_4-C_{12})$ heteroaryl group having one or more heteroatoms selected from the group consisting of O, N and S, which is optionally substituted by a halogen atom, by an optionally halogenated $(C_1-C_5)$ alyl group or by an optionally halogenated $(C_1-C_5)$ alkoxy group; or $R_3$ and $R_4$ together, form a $(C_2-C_6)$ alkylene chain optionally substituted by a halogen atom or by optionally halogenated $(C_1-C_5)$ alkoxy;

R is a halogen atom; a cyano group; a nitro group; a carboxy group; an optionally halogenated $(C_1-C_{18})$ alkoxycarbonyl group; an $R_a$—CO—NH— or $R_aR_bN$—CO— group, an optionally halogenated $(C_1-C_{18})$ alkyl group; optionally halogenated $(C_1-C_{18})$ alkoxy; $(C_6-C_{10})$ aryl, $(C_6-C_{10})$ aryl $(C_1-C_5)$ alkyl, $(C_6-C_{10})$ aryloxy, $(C_3-C_{12})$ cycloalkyl, $(C_3-C_{12})$ cycloalkenyl, $(C_3-C_{12})$ cycloalkyloxy or $(C_3-C_{12})$ cycloalkenyloxy in which any aryl, cycloalkyl and cycloalkenyl are optionally substituted by a halogen atom, by optionally halogenated $(C_1-C_5)$ alkyl or by optionally halogenated $(C_1-C_5)$ alkoxy;

X is O or S;

p is, 0, 1, 2, 3 or 4; and $W_0$ is methyl or bromomethyl, with the proviso that 5-ethyl-2,3-dihydro-benzooxepine is excluded.

20. A compound of formula

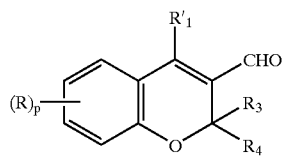

wherein $R'_1$ is a hydrogen atom, a $(C_1-C_5)$ alkyl group or a phenyl group;

$R_3$ and $R_4$ are, independently, a hydrogen atom, a $(C_1-C_{18})$ alkyl group or a $(C_2-C_{18})$ alkenyl group, with the proviso that 2H-chromene-3-carbaldehyde and 3-methyl-2H-chromene-3-carbaldehyde are excluded.

21. A pharmaceutical composition comprising an effective amount of at least one compound of formula (I) according to claim 1 and at least one pharmaceutically acceptable vehicle.

22. A process according to claim 9, wherein the ylide is prepared by reacting a metal hydride with a phosphonate at a temperature of –5° C. to 30° C.

23. A process according to claim 9, wherein the ylide is prepared by reacting an alkali metal alkoxide with a phosphonate at a temperature of 20° C. to 70° C.

24. A process according to claim 9, wherein the reaction of the ylide with the aldehyde of formula (III) is carried out in an aprotic solvent at a temperature of –5° C. to 30° C.

25. A process according to claim 10, wherein the ylide is prepared by reacting a base with a phosphonate.

26. A process according to claim 10, wherein the base is an alkali metal hydride, an alkali metal carbonate, an alkali metal amide, a $(C_1-C_{10})$ alkyllithium or an alkali metal alkoxide.

27. A process according to claim 10, wherein step a) is carried out in the presence of an aprotic solvent which is selected from the group consisting of an aromatic hydrocarbon, an ester, or a mixture thereof.

28. A process according to claim 10, wherein the aldehyde of formula (III) is added to the resultant reaction mixture of step a).

29. A process according to claim 10, wherein the ylide is prepared by reacting a metal hydride with a phosphonate at a temperature of –10° C. to 50° C.

30. A process according to claim 10, wherein the ylide is prepared by reacting an alkali metal alkoxide with a phosphonate at a temperature of 10° C. to 100° C.

31. A process according to claim 10, wherein the reaction of the ylide with the aldehyde of formula (III) is carried out in an aprotic solvent at a temperature of –10° C. to 50° C.

32. A process according to claim 10, wherein the ylide is prepared by reacting a metal hydride with a phosphonate at a temperature of –5° C. to 30° C.

33. A process according to claim 10, wherein the ylide is prepared by reacting an alkali metal alkoxide with a phosphonate at a temperature of 20° C. to 70° C.

34. A process according to claim 10, wherein the reaction of the ylide with the aldehyde of formula (III) is carried out in an aprotic solvent at a temperature of –5° C. to 30° C.

35. A method of preparing a pharmaceutical composition comprising bringing together a compound of formula (I) according to claim 1, and a pharmaceutically acceptable vehicle.

36. A method of treating or preventing dyslipidaemias, atherosclerosis or diabetes comprising administering an effective amount of a pharmaceutical composition of claim 21 to a host in need thereof.

* * * * *

UNITED STATES PATENT AND TRADEMARK OFFICE
CERTIFICATE OF CORRECTION

PATENT NO. : 6,596,758 B1
DATED : July 22, 2003
INVENTOR(S) : Brunet et al.

It is certified that error appears in the above-identified patent and that said Letters Patent is hereby corrected as shown below:

Column 81,
Lines 44 and 45, reads "$(CH_2)_x$," should read -- $(CH_2)_s$ --

Column 83,
Line 7, delete "$(C_3-C_5)$ alkyl;"

Column 84,
Line 46, reads "henyl" should read -- phenyl --

Column 87,
Line 63, reads "$(CH_2)_x$," should read -- $(CH_2)_s$ --

Column 89,
Line 20, has the formula 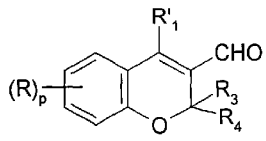

should have the formula 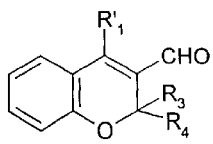

Signed and Sealed this

Fourteenth Day of September, 2004

JON W. DUDAS
Director of the United States Patent and Trademark Office